United States Patent
Kwon et al.

(10) Patent No.: US 10,927,183 B2
(45) Date of Patent: Feb. 23, 2021

(54) ANTI-HUMAN VSIG4 ANTIBODIES AND USES THEREOF

(71) Applicant: Eutilex Co., Ltd., Seoul (KR)

(72) Inventors: Byoung S. Kwon, Seoul (KR); Hye Jeong Kim, Seoul (KR); Sunhee Hwang, Seoul (KR); Joongwon Lee, Seoul (KR); Seung Hyun Lee, Seoul (KR); Sun Woo Im, Seoul (KR); Jin Kyung Choi, Seoul (KR); Hyun Tae Son, Seoul (KR); Hyeok-Jun Park, Seoul (KR)

(73) Assignee: Eutilex Co., Ltd., Seoul (KR)

( * ) Notice: Subject to any disclaimer, the term of this patent is extended or adjusted under 35 U.S.C. 154(b) by 0 days.

(21) Appl. No.: 16/838,887

(22) Filed: Apr. 2, 2020

(65) Prior Publication Data
US 2020/0291126 A1    Sep. 17, 2020

Related U.S. Application Data

(63) Continuation of application No. PCT/US2019/053824, filed on Sep. 30, 2019.

(60) Provisional application No. 62/776,523, filed on Dec. 7, 2018, provisional application No. 62/738,255, filed on Sep. 28, 2018.

(51) Int. Cl.
| | |
|---|---|
| *C07K 16/28* | (2006.01) |
| *A61K 39/395* | (2006.01) |
| *A61P 35/00* | (2006.01) |
| *C07K 16/30* | (2006.01) |
| *C12N 15/85* | (2006.01) |
| *A61K 45/06* | (2006.01) |
| *A61K 39/00* | (2006.01) |

(52) U.S. Cl.
CPC ............ *C07K 16/30* (2013.01); *A61P 35/00* (2018.01); *C07K 16/2803* (2013.01); *C12N 15/85* (2013.01); *A61K 45/06* (2013.01); *A61K 2039/505* (2013.01); *C07K 2317/24* (2013.01); *C07K 2317/51* (2013.01); *C07K 2317/515* (2013.01); *C07K 2317/56* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,445,643 B2 * | 5/2013 | Kwon ................... | A61P 37/04 530/387.1 |
| 2014/0056890 A1 * | 2/2014 | Gurney ................ | A61K 38/1774 424/134.1 |
| 2018/0371095 A1 * | 12/2018 | Aggeler ............... | A61K 31/573 |

FOREIGN PATENT DOCUMENTS

| | | |
|---|---|---|
| JP | 2016/222656 | 12/2016 |
| WO | WO 2008/112017 | 9/2008 |
| WO | WO 2008/130204 | 10/2008 |

OTHER PUBLICATIONS

Balducci L. 2016 Seminars in Oncology Nursing, vol. 32, No. 3: pp. 314-324.*
Chothia et al., "Conformations of immunoglobulin hypervariable regions", Nature 342: 877-883, 1989.
International Search Report and Written Opinion in International Application No. PCT/US19/53824, dated Feb. 28, 2020, 18 pages.
Jones et al., "Replacing the complementarity-determining regions in a human antibody with those from a mouse", Nature 321, 522-525, 1986.
Wu et al., "Humanization of a murine monoclonal antibody by simultaneous optimization of framework and CDR residues", J Mol. Biol. 294: 151-162, 1999.
Wu, "Simultaneous Humanization and Affinity Optimization of Monoclonal Antibodies", Methods in Mol. Biol. 207: 197-212, 2003.

* cited by examiner

*Primary Examiner* — Ilia I Ouspenski
(74) *Attorney, Agent, or Firm* — Fish & Richardson P.C.

(57) ABSTRACT

Provided are antibodies and antigen-binding fragment thereof that bind to VSIG4. Various in vitro and in vivo methods and compositions related to antibodies. Methods include prevention and/or therapeutic treatment of cancer using an antibody or an antigen-binding fragment that binds to VSIG4.

28 Claims, 59 Drawing Sheets
Specification includes a Sequence Listing.

FIG. 2A

```
                   301                                                                           400
EU103           (251) LKATSTVKQSWDWTTDM-DGYLGETSAGPGKSLPVFAILIISLCCMVVFTMAYIMLCRKTSQQEHVYEAARAHARE--ANDSGETMRVAIFASGCSSDE
human B7-1 (CD80)  (260) ICCLTYCFAPRCRERRRNERLRRESVRPV-
human B7-2 (CD86)  (269) RPRNSYKCGTNMRESEQTKKREKIHIPERSDEAQRVFKSSKTSSCDKSDTCF-
human B7-H4 (VTCN1)(157) LPLSPYIMLK-
human B7-DC (PDCD1LG2)(241) IALRKQLCRKLYSSKDTTKRPVTTKREVNSAI
human PDL1 (CD274) (261) LRKGRMMDVKKCGIQDTNSKKQSDTHLEET-
human B7-H3 (CD276)(287) LTDTKQLVHSFTEGRDQGSAYANRTALFPDLLAQGNASLRLQNVRVADEGSFTCFVSIRDFGSAAVSLQVAAPYSKPSMTLEPNKDLRPGDTVTITCSSY
human B7-H2 (ICOSL)(266) LVVVAVAIGWVCRDRCLQHSYAGAWAVSPETELTGHV-
                   401                                                      500
EU103           (349) PTSQNLGNNYSEPCIGQEYQIIAQINGNYARLLDTVPLDYEFLATEGKSVC-
human B7-1 (CD80)  (289) -
human B7-2 (CD86)  (324) -
human B7-H4 (VTCN1)(167) -
human B7-DC (PDCD1LG2)(274) -
human PDL1 (CD274) (291) -
human B7-H3 (CD276)(387) RGYPEAEVTWQDGQGVPLTGNVTTSQMANEQGLFDVHSVLRVVLGANGTYSCLVRNPVLQQDAHGSVTITGQPMTFPPEALWVTVGLSVCLIALLVALAF
human B7-H2 (ICOSL)(303) -
                   501            548
EU103           (400) -
human B7-1 (CD80)  (289) -
human B7-2 (CD86)  (324) -
human B7-H4 (VTCN1)(167) -
human B7-DC (PDCD1LG2)(274) -
human PDL1 (CD274) (291) -
human B7-H3 (CD276)(487) VCWRKIKQSCEEENAGAEDQDGEGEGSKTALQPLKHSDSKEDDGQEIA
human B7-H2 (ICOSL)(303) -
```

FIG. 2A (Cont.)

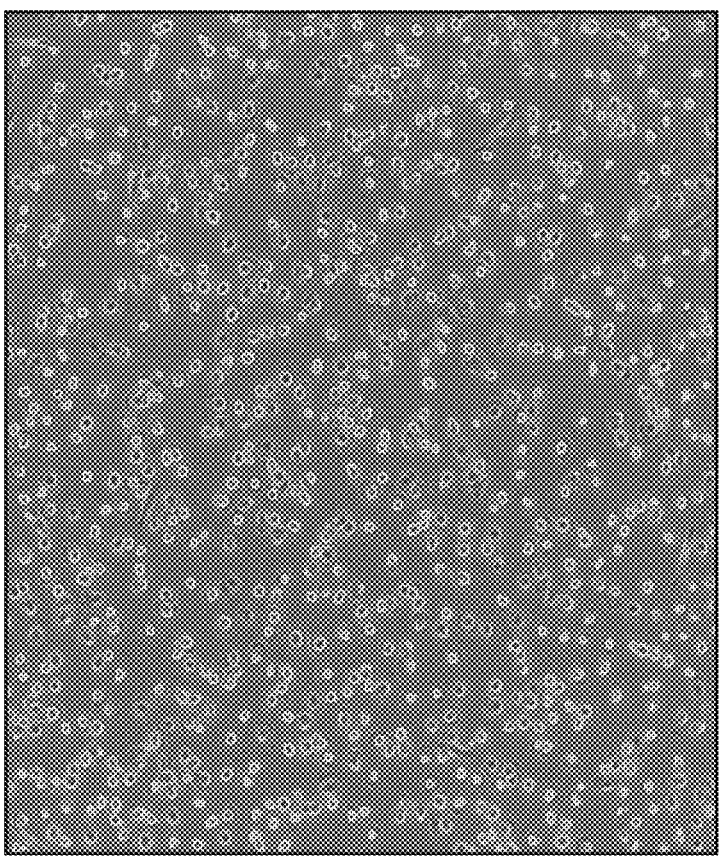
FIG. 5

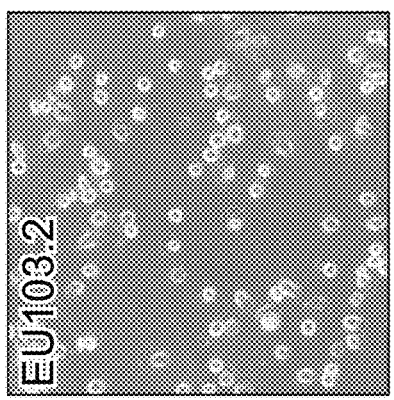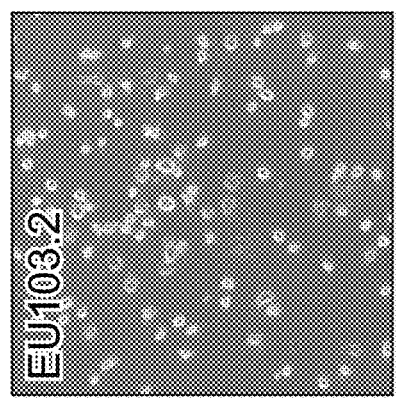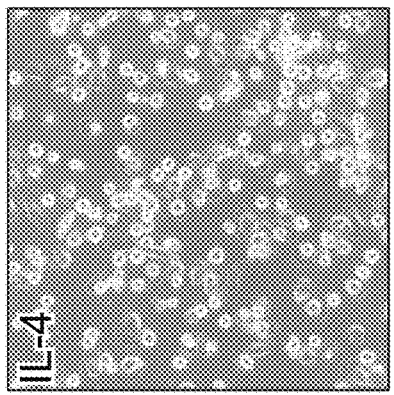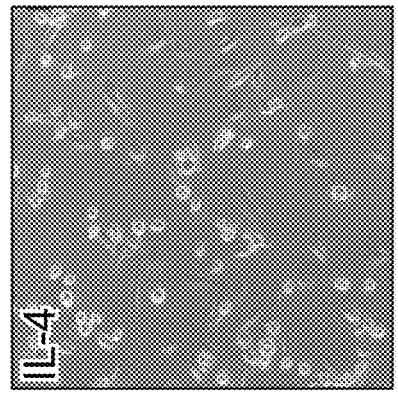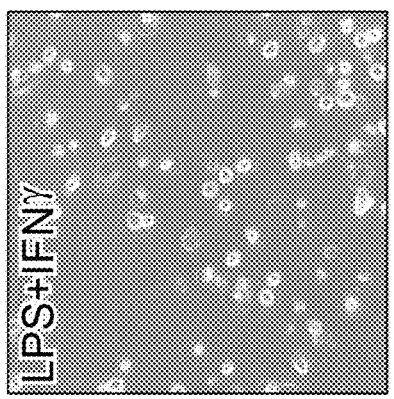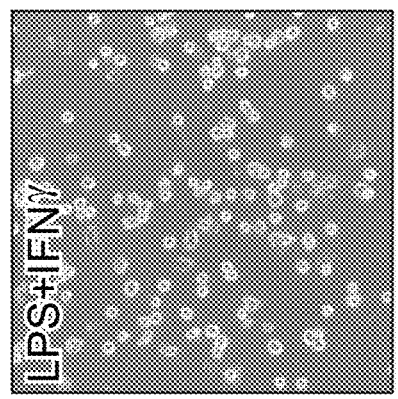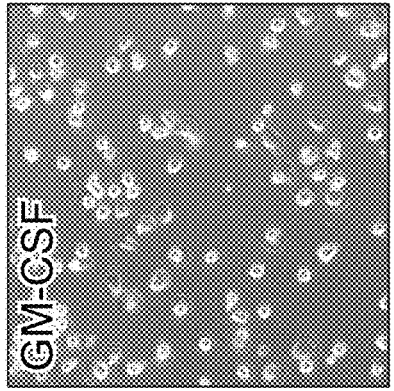
FIG. 12

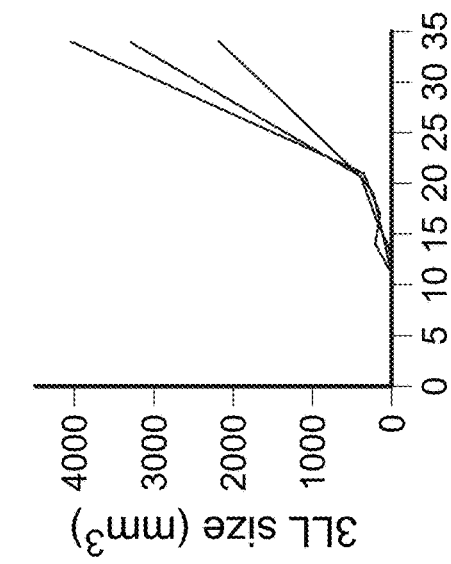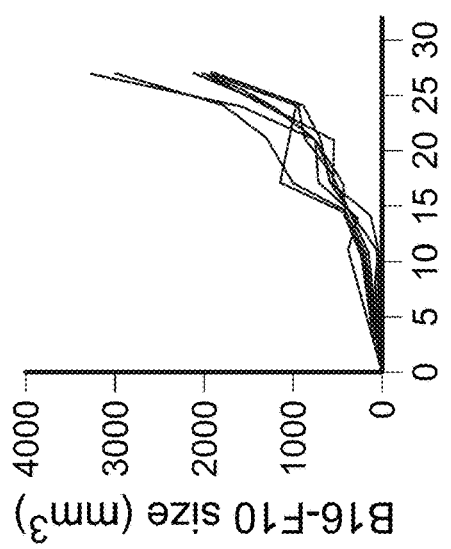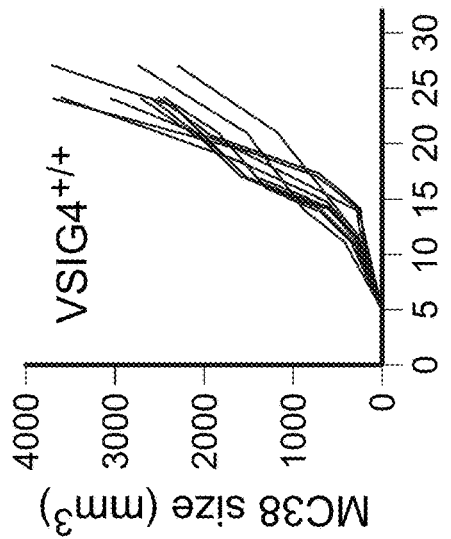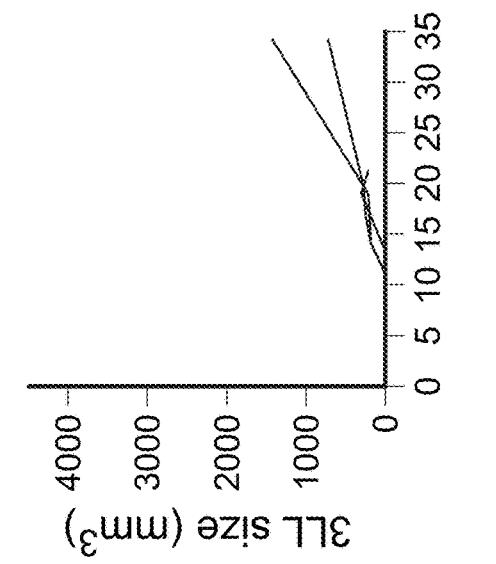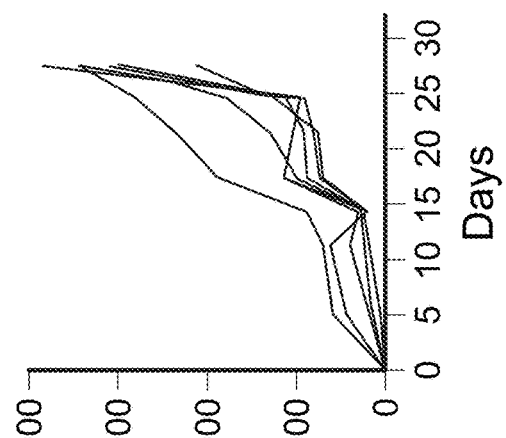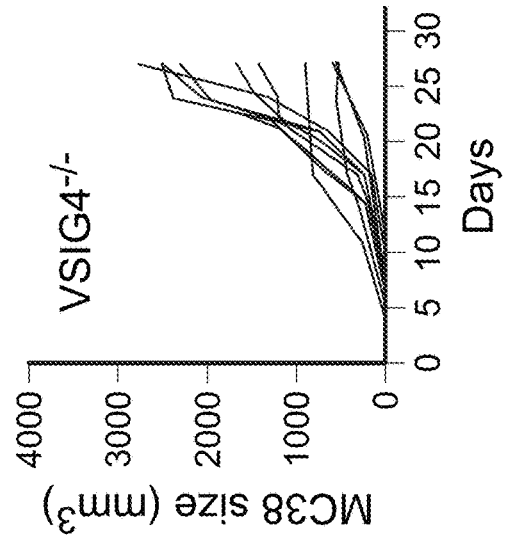
FIG. 15A   FIG. 15B   FIG. 15C

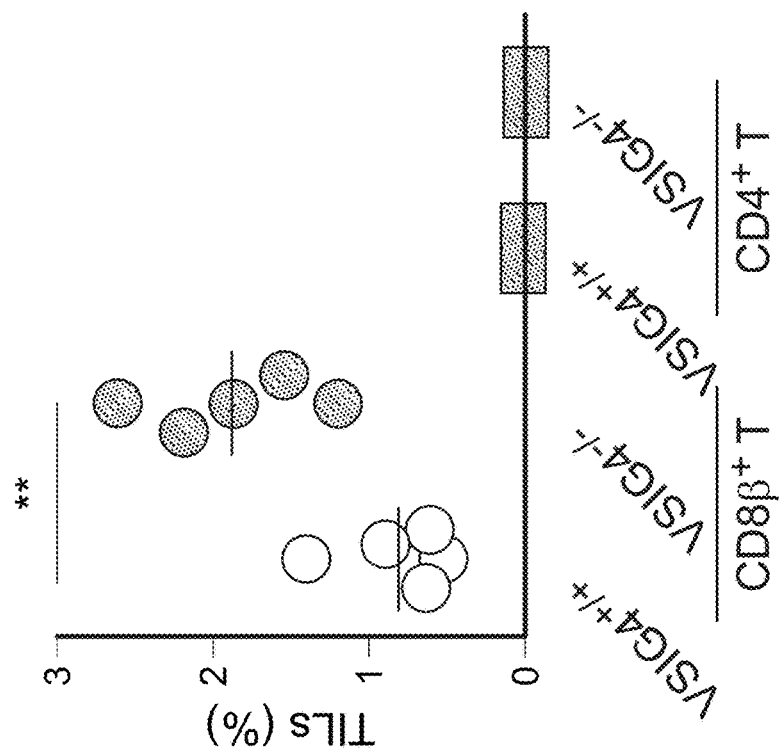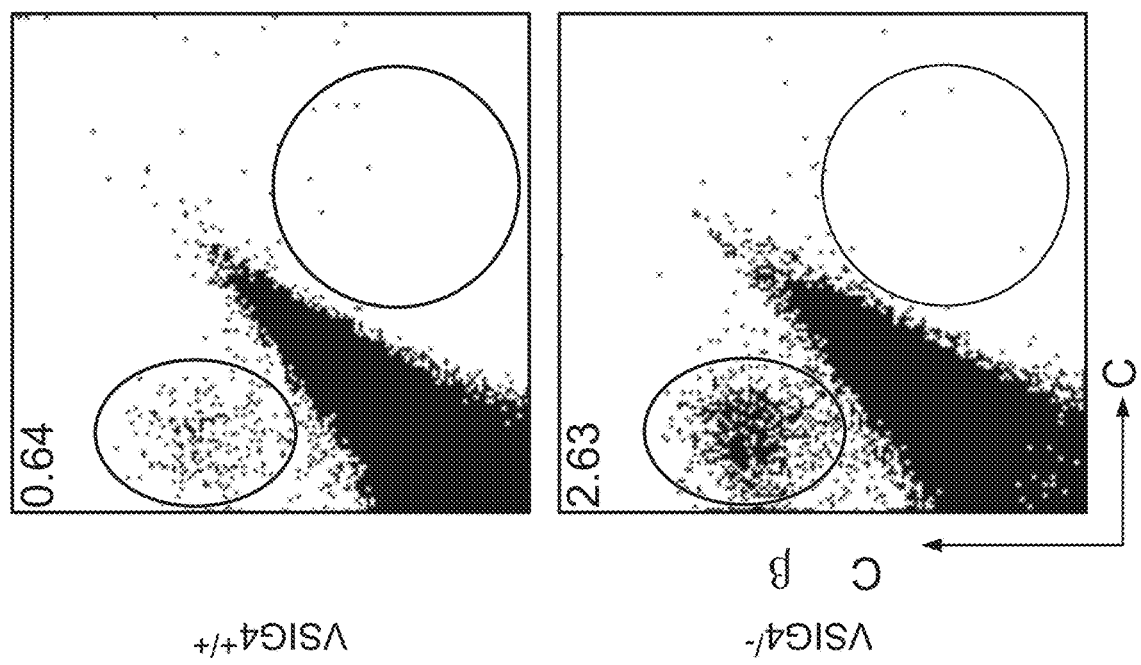
FIG. 17C

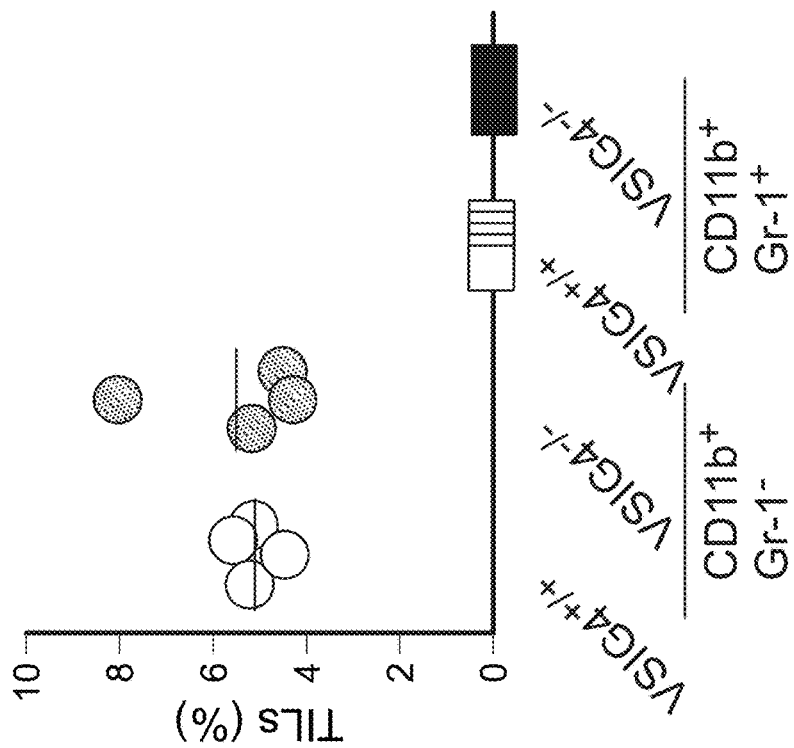
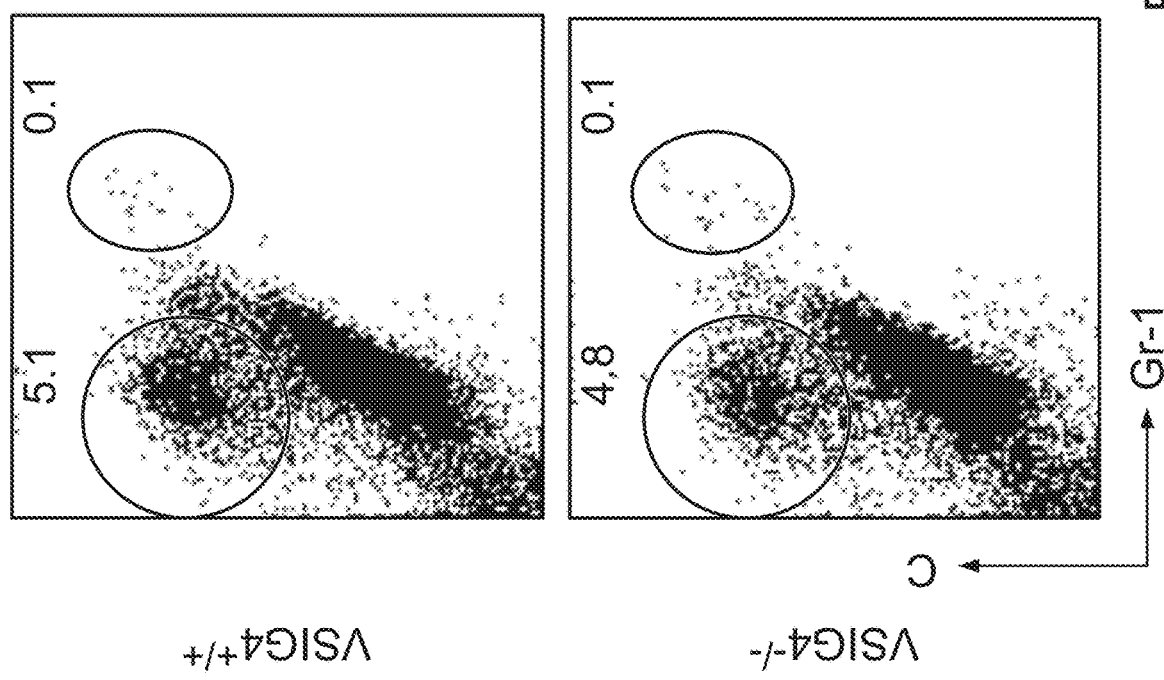
FIG. 17D

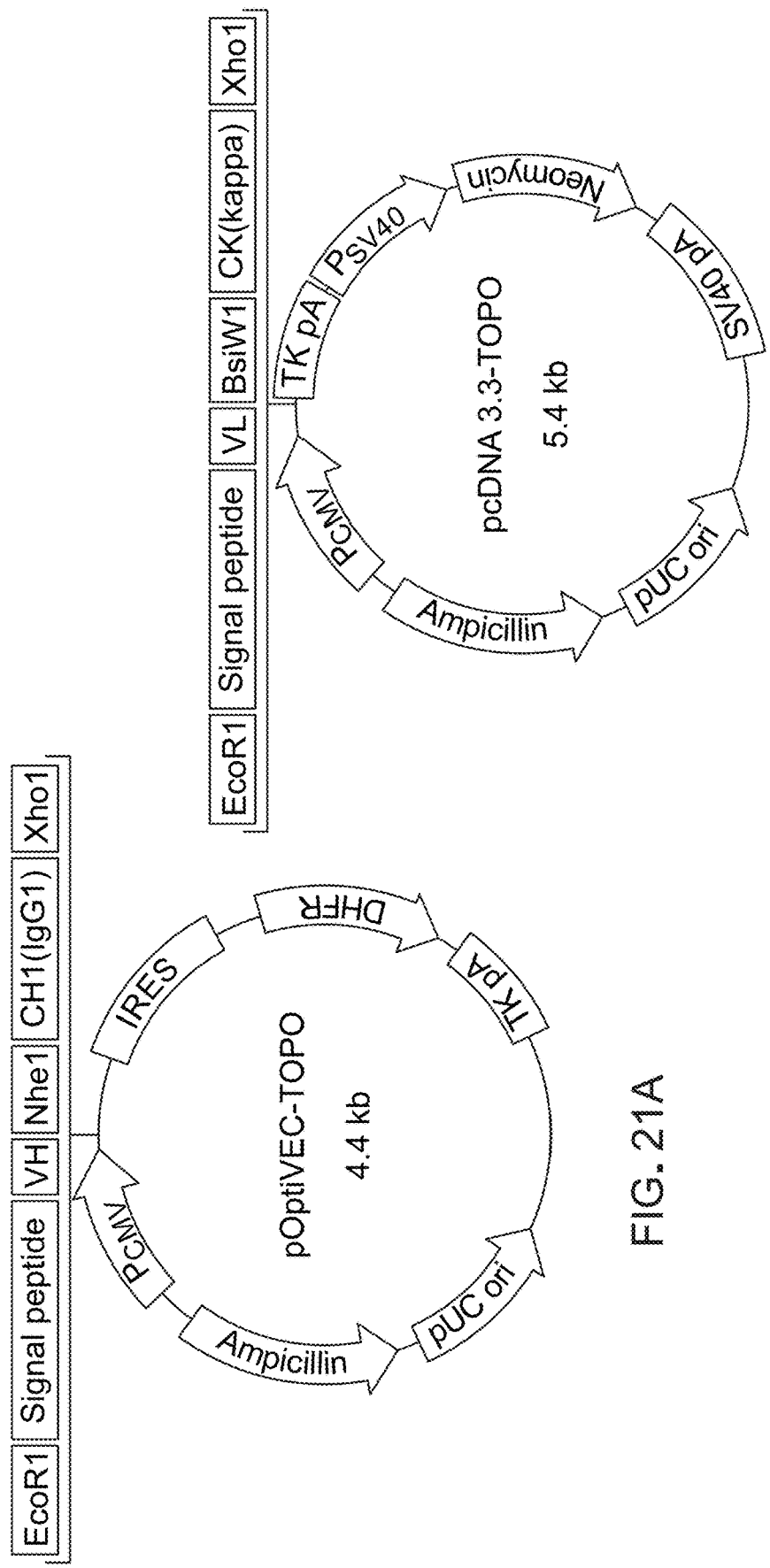

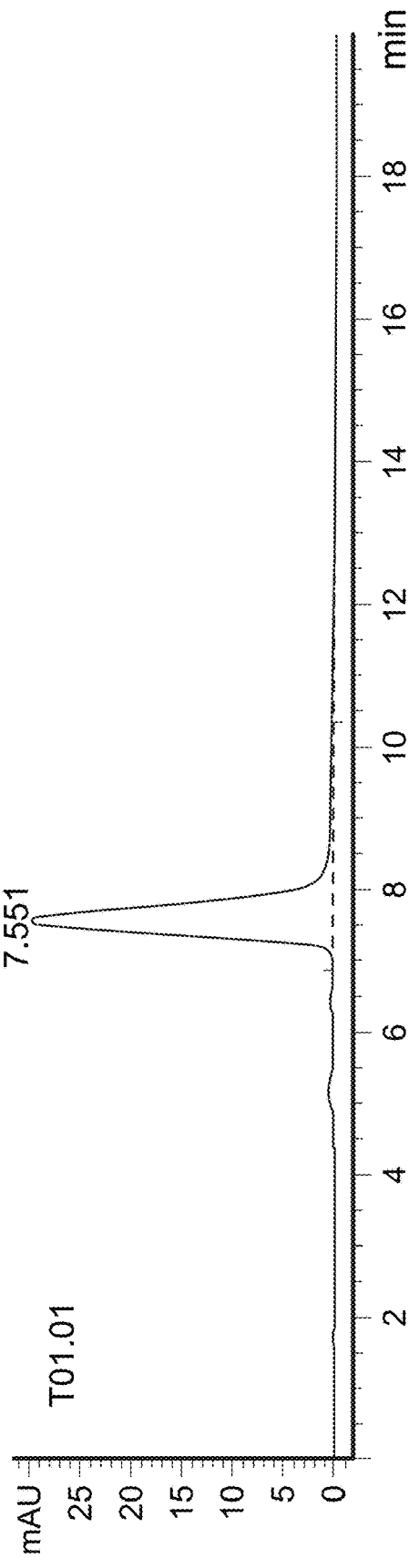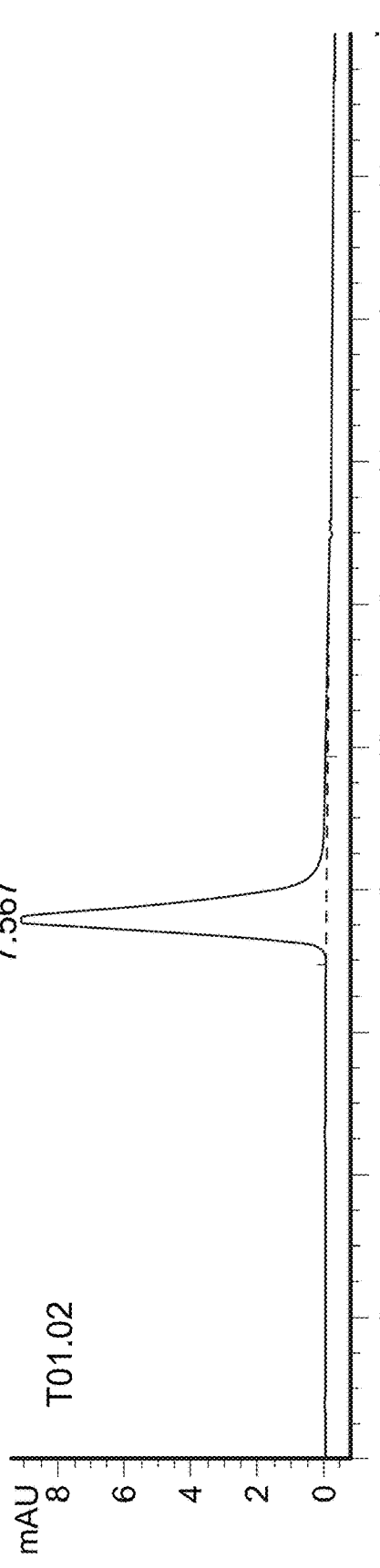

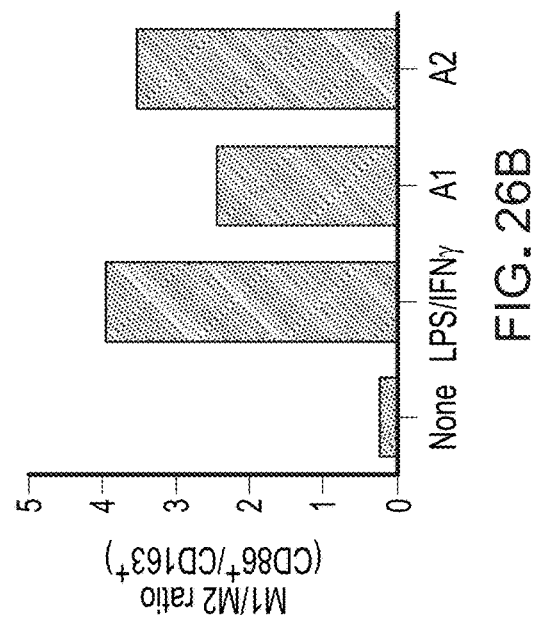
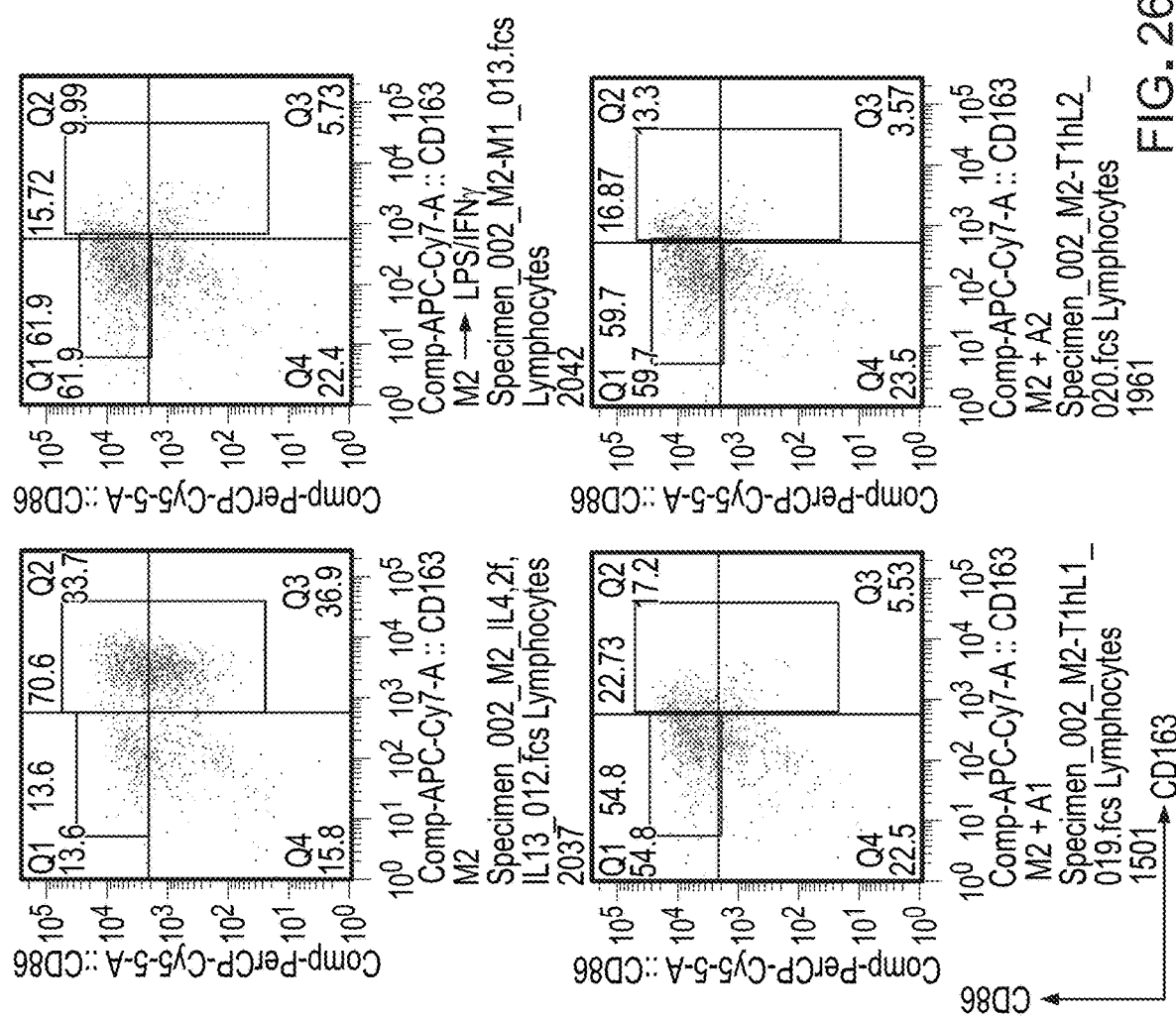
FIG. 26A
FIG. 26B

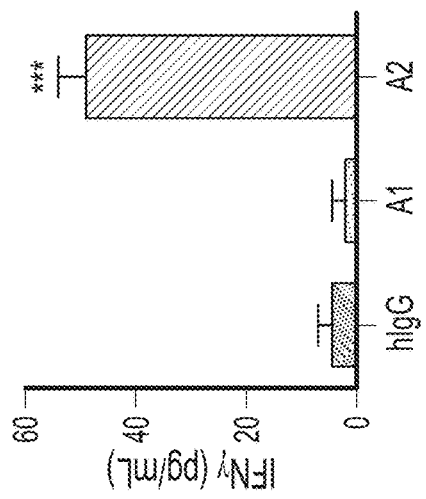
FIG. 31C
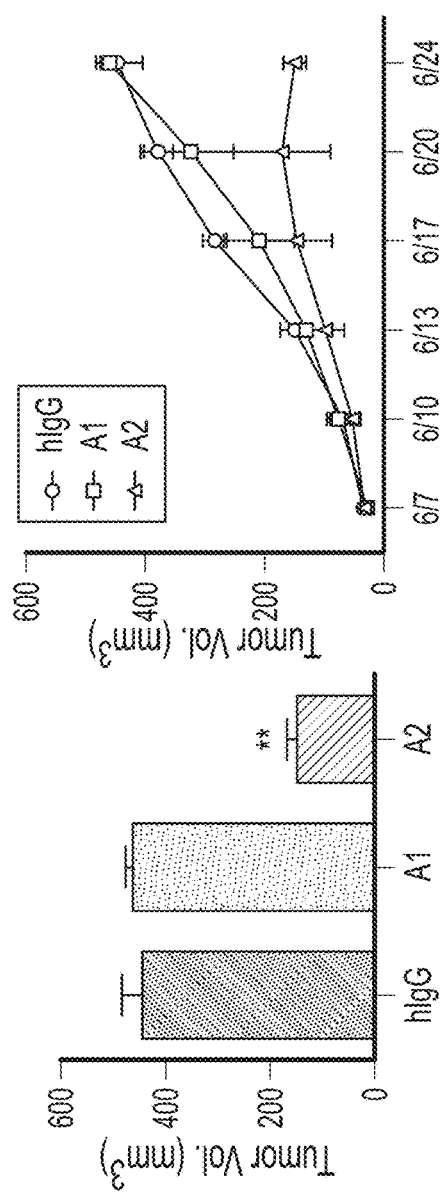
FIG. 31B
FIG. 31A
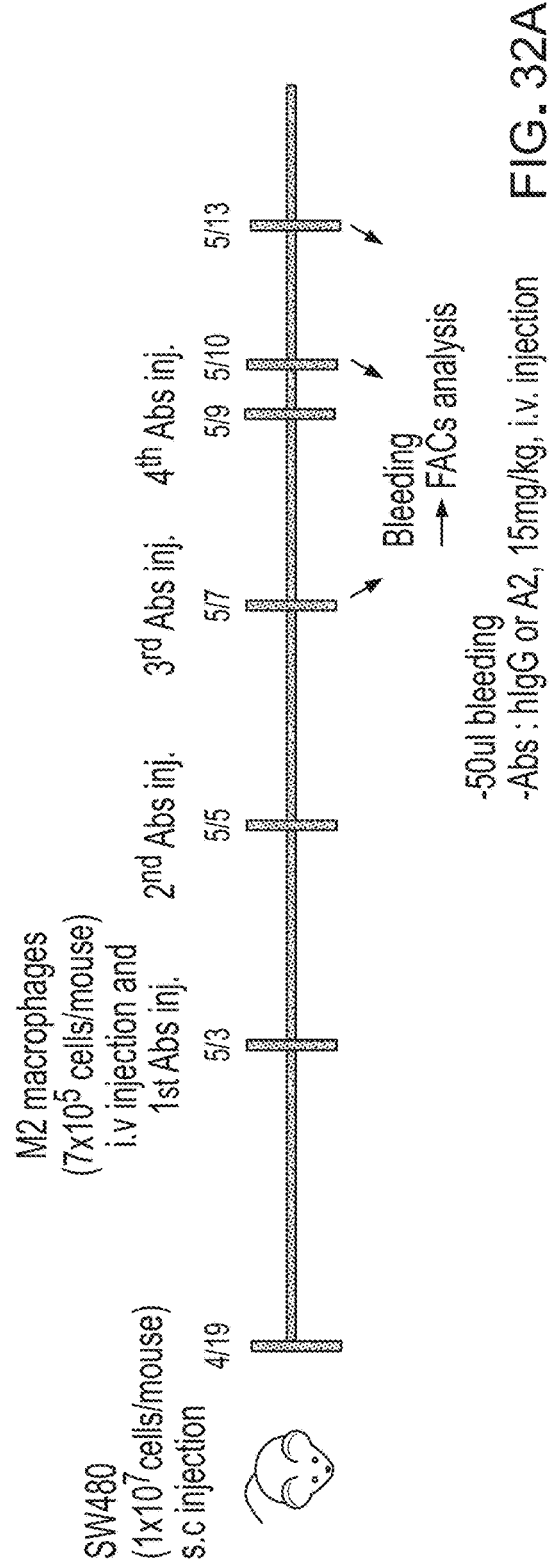
FIG. 32A

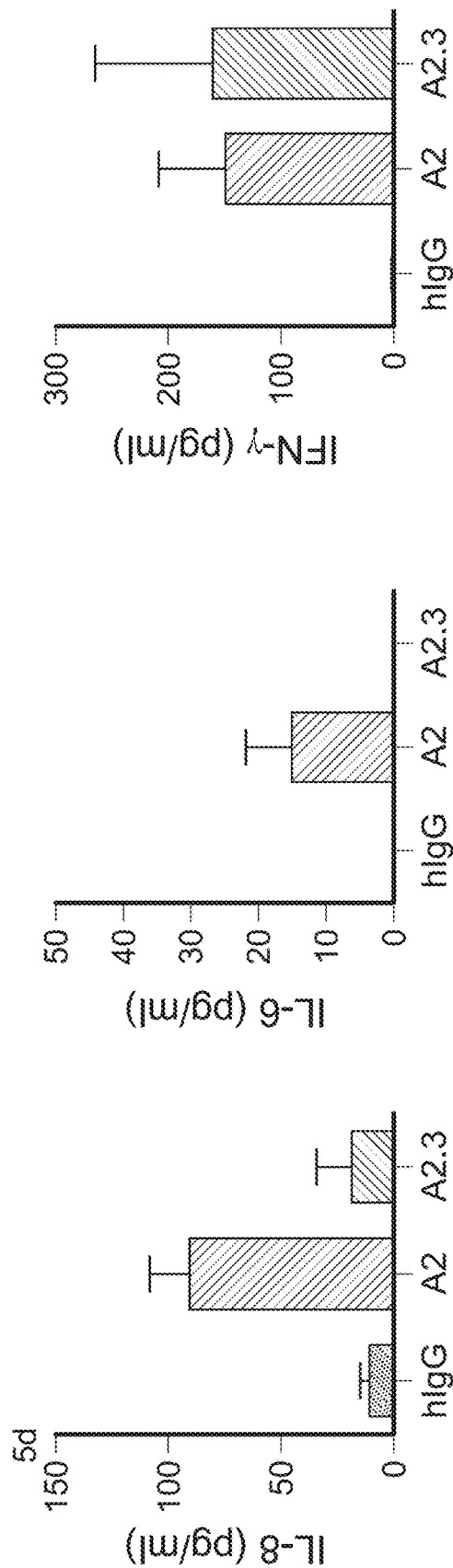
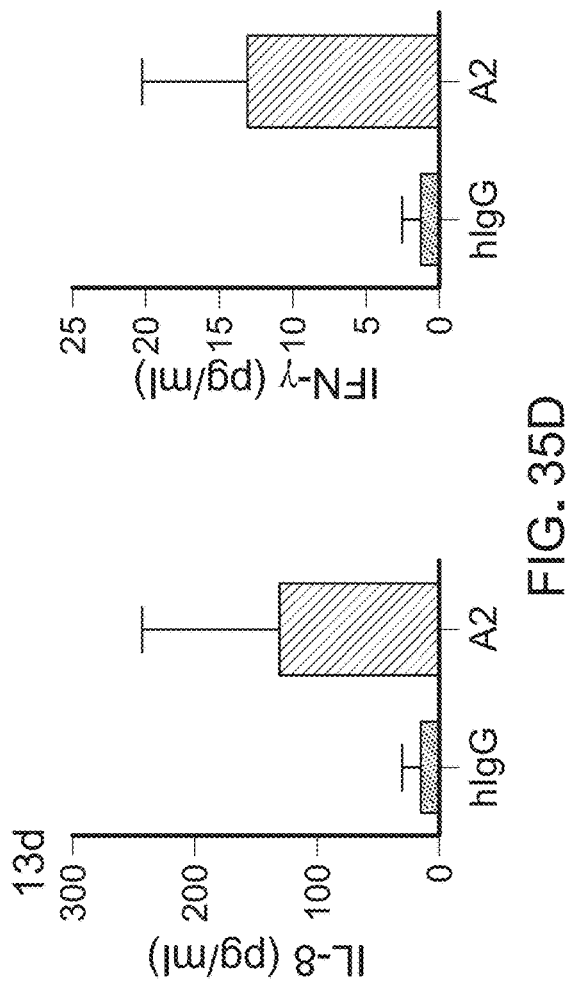
FIG. 35C
FIG. 35D

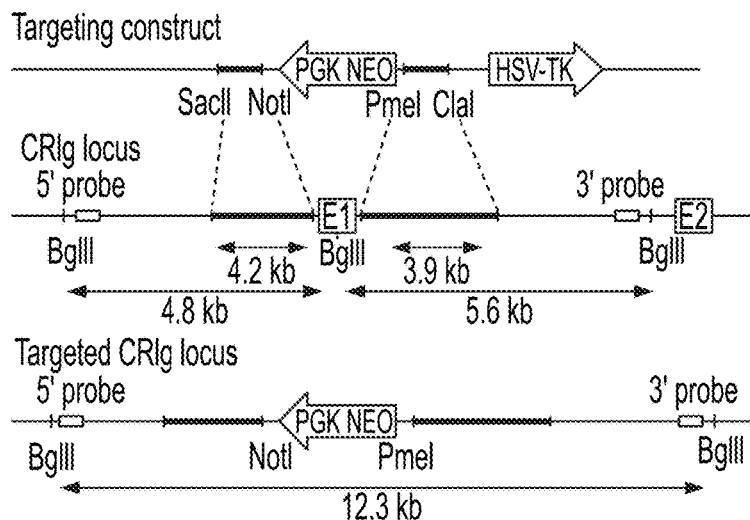
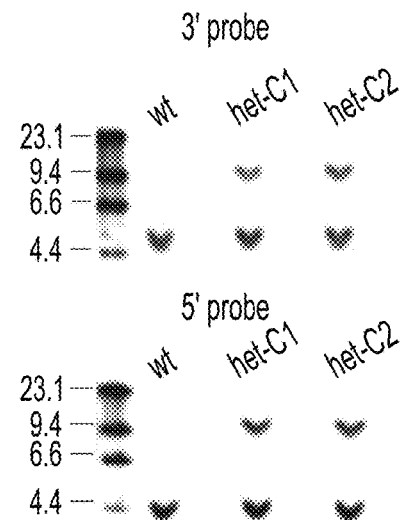
FIG. 41A
FIG. 41B
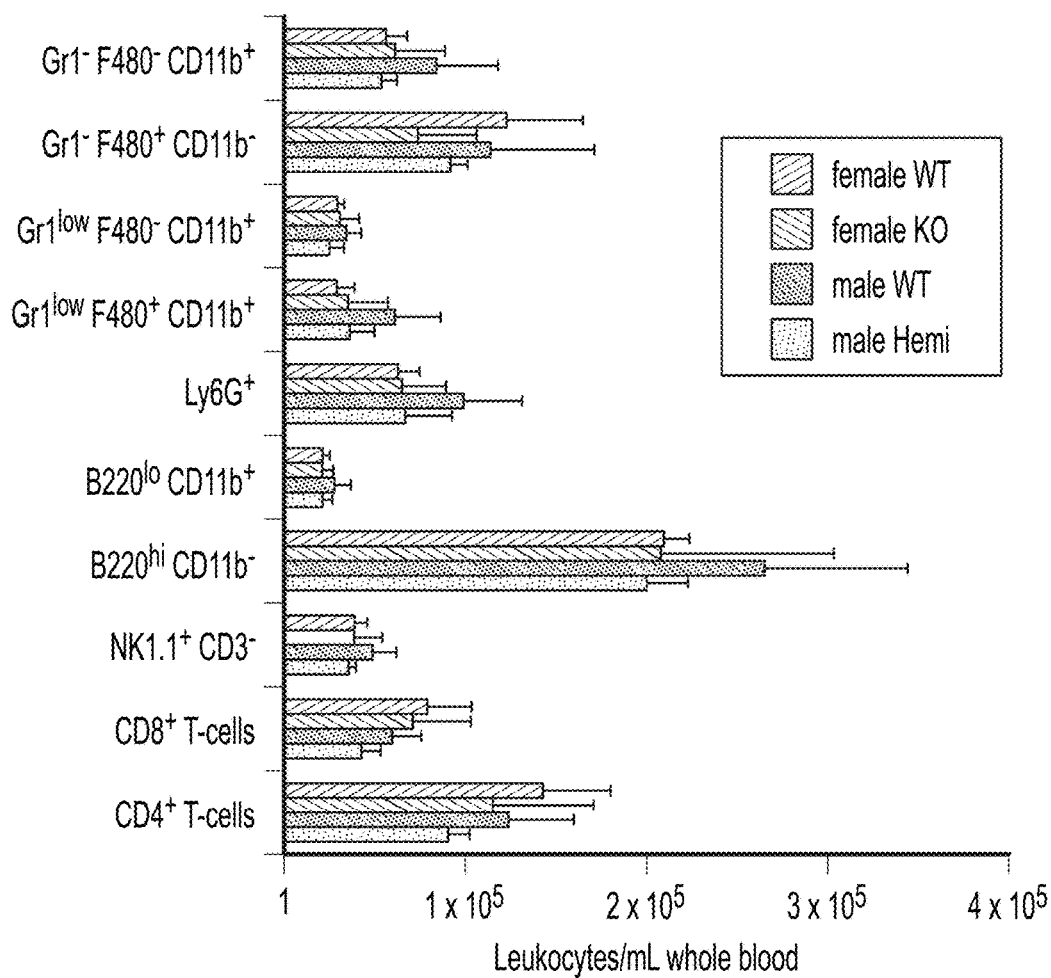
FIG. 41C

SEQUENCE LISTING

<160> NUMBER OF SEQ ID NOS: 31

<210> SEQ ID NO 1

<400> SEQUENCE: 1

000

<210> SEQ ID NO 2
<211> LENGTH: 121
<212> TYPE: PRT
<213> ORGANISM: Artificial
<220> FEATURE:
<223> OTHER INFORMATION: synthetic polypeptide

<400> SEQUENCE: 2

Gln Val Gln Leu Gln Glu Ser Gly Pro Gly Leu Val Lys Pro Ser Gln
1               5                   10                  15

Thr Leu Ser Leu Thr Cys Ser Phe Ser Gly Ile Ser Leu Thr Thr Ser
            20                  25                  30

Gly Met Gly Val Gly Trp Ile Arg Gln Pro Pro Gly Lys Gly Leu Glu
        35                  40                  45

Trp Leu Ala Asp Ile Phe Trp Asp Asp Asn Lys Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Val Arg Val Tyr Tyr Lys Asn Asp Gly Tyr Phe Asp Val Trp Gly
            100                 105                 110

Gln Gly Thr Leu Val Thr Val Ser Ser
        115                 120

<210> SEQ ID NO 3

<400> SEQUENCE: 3

000

<210> SEQ ID NO 4
<211> LENGTH: 111
<212> TYPE: PRT
<213> ORGANISM: Artificial
<220> FEATURE:
<223> OTHER INFORMATION: synthetic polypeptide

<400> SEQUENCE: 4

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Lys Ser Val Thr Thr Ser
            20                  25                  30

Gly Tyr Ser Phe Met His Trp Tyr Gln Gln Lys Pro Gly Gln Ala Pro
        35                  40                  45

Arg Leu Leu Ile Tyr Leu Ala Ser Asn Leu Glu Pro Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln His Ser Arg
                85                  90                  95

Glu Leu Pro Tyr Thr Phe Gly Gln Gly Thr Lys Leu Glu Ile Lys
            100                 105                 110
```

<210> SEQ ID NO 5

<400> SEQUENCE: 5

000

<210> SEQ ID NO 6
<211> LENGTH: 121
<212> TYPE: PRT
<213> ORGANISM: Artificial
<220> FEATURE:
<223> OTHER INFORMATION: synthetic polypeptide

<400> SEQUENCE: 6

```
Gln Val Thr Leu Lys Glu Ser Gly Pro Thr Leu Val Lys Pro Thr Gln
1               5                   10                  15

Thr Leu Thr Leu Thr Cys Thr Phe Ser Gly Ile Ser Leu Thr Thr Ser
            20                  25                  30

Gly Met Gly Val Gly Trp Ile Arg Gln Pro Pro Gly Lys Ala Leu Glu
        35                  40                  45

Trp Leu Ala Asp Ile Phe Trp Asp Asp Lys Tyr Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Val Arg Val Tyr Tyr Lys Asn Asp Gly Tyr Phe Asp Val Trp Gly
            100                 105                 110

Lys Gly Thr Thr Val Thr Val Ser Ser
        115                 120
```

<210> SEQ ID NO 7

<400> SEQUENCE: 7

000

<210> SEQ ID NO 8
<211> LENGTH: 111
<212> TYPE: PRT
<213> ORGANISM: Artificial
<220> FEATURE:
<223> OTHER INFORMATION: synthetic polypeptide

<400> SEQUENCE: 8

```
Asp Ile Val Leu Thr Gln Ser Pro Leu Ser Leu Pro Val Thr Leu Gly
1               5                   10                  15

Gln Pro Ala Ser Ile Ser Cys Arg Ala Ser Lys Ser Val Thr Thr Ser
            20                  25                  30

Gly Tyr Ser Phe Met His Trp Tyr Gln Gln Arg Pro Gly Gln Ser Pro
        35                  40                  45

Arg Leu Leu Ile Tyr Leu Ala Ser Asn Leu Glu Pro Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Glu Leu Pro Tyr Thr Phe Gly Gln Gly Thr Lys Leu Glu Ile Lys
            100                 105                 110
```

<210> SEQ ID NO 9

<400> SEQUENCE: 9

000

<210> SEQ ID NO 10
<211> LENGTH: 111
<212> TYPE: PRT
<213> ORGANISM: Artificial
<220> FEATURE:
<223> OTHER INFORMATION: synthetic polypeptide

<400> SEQUENCE: 10

```
Asp Ile Val Leu Thr Gln Ser Pro Leu Ser Leu Pro Val Thr Leu Gly
1               5                   10                  15

Gln Pro Ala Ser Ile Ser Cys Arg Ala Ser Lys Ser Val Thr Thr Ser
            20                  25                  30

Gly Tyr Ser Phe Met His Trp Tyr Gln Gln Arg Pro Gly Gln Ser Pro
        35                  40                  45

Arg Leu Leu Ile Tyr Leu Ala Ser Asn Leu Glu Pro Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Gly
                85                  90                  95

Glu Leu Pro Tyr Thr Phe Gly Gln Gly Thr Lys Leu Glu Ile Lys
            100                 105                 110
```

<210> SEQ ID NO 11

<400> SEQUENCE: 11

000

<210> SEQ ID NO 12
<211> LENGTH: 111

```
<212> TYPE: PRT
<213> ORGANISM: Artificial
<220> FEATURE:
<223> OTHER INFORMATION: synthetic polypeptide

<400> SEQUENCE: 12

Asp Ile Val Leu Thr Gln Ser Pro Leu Ser Leu Pro Val Thr Leu Gly
1               5                   10                  15

Gln Pro Ala Ser Ile Ser Cys Arg Ala Ser Lys Ser Val Thr Thr Ser
            20                  25                  30

Gly Tyr Ser Phe Met His Trp Tyr Gln Gln Arg Pro Gly Gln Ser Pro
        35                  40                  45

Arg Leu Leu Ile Tyr Leu Ala Ser Asn Leu Glu Pro Gly Val Pro Asp
    50                  55                  60

Arg Phe Ser Gly Ser Gly Ser Gly Thr Asp Phe Thr Leu Lys Ile Phe
65                  70                  75                  80

Arg Val Glu Ala Glu Asp Val Gly Val Tyr Tyr Cys Gln Gln Ser Gly
                85                  90                  95

Glu Leu Pro Tyr Thr Phe Gly Gln Gly Thr Lys Leu Glu Ile Lys
            100                 105                 110

<210> SEQ ID NO 13

<400> SEQUENCE: 13

000

<210> SEQ ID NO 14
<211> LENGTH: 121
<212> TYPE: PRT
<213> ORGANISM: Artificial
<220> FEATURE:
<223> OTHER INFORMATION: synthetic polypeptide

<400> SEQUENCE: 14

Gln Val Thr Leu Val Glu Ser Gly Pro Thr Leu Val Lys Pro Gly Gln
1               5                   10                  15

Thr Leu Thr Leu Thr Cys Thr Phe Ser Gly Ile Ser Leu Thr Thr Ser
            20                  25                  30

Gly Met Gly Val Gly Trp Ile Arg Gln Pro Pro Gly Lys Ala Leu Glu
        35                  40                  45

Trp Leu Ala Asp Ile Phe Trp Asp Asp Asn Lys Tyr Tyr Asn Pro Ser
    50                  55                  60

Leu Lys Gly Arg Leu Thr Ile Thr Lys Asp Thr Ser Lys Asn Gln Val
65                  70                  75                  80

Tyr Leu Thr Met Thr Asn Met Asp Pro Val Asp Thr Ala Thr Tyr Tyr
                85                  90                  95

Cys Val Arg Val Tyr Tyr Lys Asn Asp Gly Tyr Phe Asp Val Trp Gly
            100                 105                 110

Lys Gly Thr Thr Val Thr Val Ser Ser
        115                 120

<210> SEQ ID NO 15

<400> SEQUENCE: 15

000

<210> SEQ ID NO 16
<211> LENGTH: 121
```

<212> TYPE: PRT
<213> ORGANISM: Artificial
<220> FEATURE:
<223> OTHER INFORMATION: synthetic polypeptide

<400> SEQUENCE: 16

```
Gln Val Thr Leu Val Glu Ser Gly Pro Thr Leu Val Lys Pro Gly Gln
1               5                   10                  15

Thr Leu Thr Leu Thr Cys Thr Phe Ser Gly Ile Ser Leu Thr Thr Ser
            20                  25                  30

Gly Met Gly Val Gly Trp Ile Arg Gln Pro Pro Gly Lys Ala Leu Glu
        35                  40                  45

Trp Leu Ala Asp Ile Phe Trp Asp Asp Asn Lys Tyr Tyr Asn Pro Ser
50                  55                  60

Leu Lys Gly Arg Leu Thr Ile Thr Lys Asp Thr Ser Lys Asn Gln Val
65                  70                  75                  80

Tyr Leu Thr Met Thr Asn Met Asp Pro Val Asp Thr Ala Thr Tyr Tyr
                85                  90                  95

Cys Val Arg Val Tyr Tyr Lys Asn Asp Gly Tyr Phe Asp Val Trp Gly
            100                 105                 110

Lys Gly Thr Thr Val Thr Val Ser Ser
        115                 120
```

<210> SEQ ID NO 17
<211> LENGTH: 6
<212> TYPE: PRT
<213> ORGANISM: Artificial
<220> FEATURE:
<223> OTHER INFORMATION: synthetic polypeptide

<400> SEQUENCE: 17

```
Gly Ile Ser Leu Thr Thr
1               5
```

<210> SEQ ID NO 18
<211> LENGTH: 7
<212> TYPE: PRT
<213> ORGANISM: Artificial
<220> FEATURE:
<223> OTHER INFORMATION: synthetic polypeptide

<400> SEQUENCE: 18

```
Ile Phe Trp Asp Asp Asn Lys
1               5
```

<210> SEQ ID NO 19
<211> LENGTH: 13
<212> TYPE: PRT
<213> ORGANISM: Artificial
<220> FEATURE:
<223> OTHER INFORMATION: synthetic polypeptide

<400> SEQUENCE: 19

```
Val Arg Val Tyr Tyr Lys Asn Asp Gly Tyr Phe Asp Val
1               5                   10
```

<210> SEQ ID NO 20
<211> LENGTH: 6
<212> TYPE: PRT
<213> ORGANISM: Artificial
<220> FEATURE:
<223> OTHER INFORMATION: synthetic polypeptide

<400> SEQUENCE: 20

```
Lys Ser Val Thr Thr Ser
1               5

<210> SEQ ID NO 21
<211> LENGTH: 3
<212> TYPE: PRT
<213> ORGANISM: Artificial
<220> FEATURE:
<223> OTHER INFORMATION: synthetic polypeptide

<400> SEQUENCE: 21

Leu Ala Ser
1

<210> SEQ ID NO 22
<211> LENGTH: 9
<212> TYPE: PRT
<213> ORGANISM: Artificial
<220> FEATURE:
<223> OTHER INFORMATION: synthetic polypeptide

<400> SEQUENCE: 22

Gln His Ser Arg Glu Leu Pro Tyr Thr
1               5

<210> SEQ ID NO 23
<211> LENGTH: 9
<212> TYPE: PRT
<213> ORGANISM: Artificial
<220> FEATURE:
<223> OTHER INFORMATION: synthetic polypeptide

<400> SEQUENCE: 23

Gln Gln Ser Gly Glu Leu Pro Tyr Thr
1               5

<210> SEQ ID NO 24
<211> LENGTH: 399
<212> TYPE: PRT
<213> ORGANISM: Artificial
<220> FEATURE:
<223> OTHER INFORMATION: synthetic polypeptide

<400> SEQUENCE: 24

Met Gly Ile Leu Leu Gly Leu Leu Leu Gly His Leu Thr Val Asp
1               5                   10                  15

Thr Tyr Gly Arg Pro Ile Leu Glu Val Pro Glu Ser Val Thr Gly Pro
            20                  25                  30

Trp Lys Gly Asp Val Asn Leu Pro Cys Thr Tyr Asp Pro Leu Gln Gly
        35                  40                  45

Tyr Thr Gln Val Leu Val Lys Trp Leu Val Gln Arg Gly Ser Asp Pro
    50                  55                  60

Val Thr Ile Phe Leu Arg Asp Ser Ser Gly Asp His Ile Gln Gln Ala
65                  70                  75                  80

Lys Tyr Gln Gly Arg Leu His Val Ser His Lys Val Pro Gly Asp Val
                85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys Leu Ser Val Ser Lys Pro Thr
    130                 135                 140
```

Val Thr Thr Gly Ser Gly Tyr Gly Phe Thr Val Pro Gln Gly Met Arg
145                 150                 155                 160

Ile Ser Leu Gln Cys Gln Ala Arg Gly Ser Pro Pro Ile Ser Tyr Ile
                165                 170                 175

Trp Tyr Lys Gln Gln Thr Asn Asn Gln Glu Pro Ile Lys Val Ala Thr
            180                 185                 190

Leu Ser Thr Leu Leu Phe Lys Pro Ala Val Ile Ala Asp Ser Gly Ser
        195                 200                 205

Tyr Phe Cys Thr Ala Lys Gly Gln Val Gly Ser Glu Gln His Ser Asp
    210                 215                 220

Ile Val Lys Phe Val Val Lys Asp Ser Ser Lys Leu Leu Lys Thr Lys
225                 230                 235                 240

Thr Glu Ala Pro Thr Thr Met Thr Tyr Pro Leu Lys Ala Thr Ser Thr
                245                 250                 255

Val Lys Gln Ser Trp Asp Trp Thr Thr Asp Met Asp Gly Tyr Leu Gly
                260                 265                 270

Glu Thr Ser Ala Gly Pro Gly Lys Ser Leu Pro Val Phe Ala Ile Ile
            275                 280                 285

Leu Ile Ile Ser Leu Cys Cys Met Val Val Phe Thr Met Ala Tyr Ile
        290                 295                 300

Met Leu Cys Arg Lys Thr Ser Gln Gln Glu His Val Tyr Glu Ala Ala
305                 310                 315                 320

Arg Ala His Ala Arg Glu Ala Asn Asp Ser Gly Glu Thr Met Arg Val
                325                 330                 335

Ala Ile Phe Ala Ser Gly Cys Ser Ser Asp Glu Pro Thr Ser Gln Asn
                340                 345                 350

Leu Gly Asn Asn Tyr Ser Asp Glu Pro Cys Ile Gly Gln Glu Tyr Gln
            355                 360                 365

Ile Ile Ala Gln Ile Asn Gly Asn Tyr Ala Arg Leu Leu Asp Thr Val
        370                 375                 380

Pro Leu Asp Tyr Glu Phe Leu Ala Thr Glu Gly Lys Ser Val Cys
385                 390                 395

<210> SEQ ID NO 25
<211> LENGTH: 287
<212> TYPE: PRT
<213> ORGANISM: Homo sapiens

<400> SEQUENCE: 25

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg

```
            115                 120                 125
Glu His Leu Ala Glu Val Thr Leu Ser Val Lys Ala Asp Phe Pro Thr
    130                 135                 140
Pro Ser Ile Ser Asp Phe Glu Ile Pro Thr Ser Asn Ile Arg Arg Ile
145                 150                 155                 160
Ile Cys Ser Thr Ser Gly Gly Phe Pro Glu Pro His Leu Ser Trp Leu
                165                 170                 175
Glu Asn Gly Glu Glu Leu Asn Ala Ile Asn Thr Thr Ser Gln Asp Pro
            180                 185                 190
Glu Thr Glu Leu Tyr Ala Val Ser Ser Lys Leu Asp Phe Asn Met Thr
        195                 200                 205
Thr Asn His Ser Phe Met Cys Leu Ile Lys Tyr Gly His Leu Arg Val
    210                 215                 220
Asn Gln Thr Phe Asn Trp Asn Thr Thr Lys Gln Glu His Phe Pro Asp
225                 230                 235                 240
Asn Leu Leu Pro Ser Trp Ala Ile Thr Leu Ile Ser Val Asn Gly Ile
                245                 250                 255
Phe Val Ile Cys Cys Leu Thr Tyr Cys Phe Ala Pro Arg Cys Arg Glu
            260                 265                 270
Arg Arg Arg Asn Glu Arg Leu Arg Arg Glu Ser Val Arg Pro Val
        275                 280                 285

<210> SEQ ID NO 26
<211> LENGTH: 323
<212> TYPE: PRT
<213> ORGANISM: Homo sapiens

<400> SEQUENCE: 26

Met Gly Leu Ser Asn Ile Leu Phe Val Met Ala Phe Leu Leu Ser Gly
1               5                   10                  15
Ala Ala Pro Leu Lys Ile Gln Ala Tyr Phe Asn Glu Thr Ala Asp Leu
            20                  25                  30
Pro Cys Gln Phe Ala Asn Ser Gln Asn Gln Ser Leu Ser Glu Leu Val
        35                  40                  45
Val Phe Trp Gln Asp Gln Glu Asn Leu Val Leu Asn Glu Val Tyr Leu
    50                  55                  60
Gly Lys Glu Lys Phe Asp Ser Val His Ser Lys Tyr Met Gly Arg Thr
65                  70                  75                  80
Ser Phe Asp Ser Asp Ser Trp Thr Leu Arg Leu His Asn Leu Gln Ile
                85                  90                  95
Lys Asp Lys Gly Leu Tyr Gln Cys Ile Ile His His Lys Lys Pro Thr
            100                 105                 110
Gly Met Ile Arg Ile His Gln Met Asn Ser Glu Leu Ser Val Leu Ala
        115                 120                 125
Asn Phe Ser Gln Pro Glu Ile Val Pro Ile Ser Asn Ile Thr Glu Asn
    130                 135                 140
Val Tyr Ile Asn Leu Thr Cys Ser Ser Ile His Gly Tyr Pro Glu Pro
145                 150                 155                 160
Lys Lys Met Ser Val Leu Leu Arg Thr Lys Asn Ser Thr Ile Glu Tyr
                165                 170                 175
Asp Gly Ile Met Gln Lys Ser Gln Asp Asn Val Thr Glu Leu Tyr Asp
            180                 185                 190
Val Ser Ile Ser Leu Ser Val Ser Phe Pro Asp Val Thr Ser Asn Met
        195                 200                 205
```

```
Thr Ile Phe Cys Ile Leu Glu Thr Asp Lys Thr Arg Leu Leu Ser Ser
            210                 215                 220

Pro Phe Ser Ile Glu Leu Glu Asp Pro Gln Pro Pro Asp His Ile
225                 230                 235                 240

Pro Trp Ile Thr Ala Val Leu Pro Thr Val Ile Cys Val Met Val
                245                 250                 255

Phe Cys Leu Ile Leu Trp Lys Trp Lys Lys Lys Arg Pro Arg Asn
                260                 265                 270

Ser Tyr Lys Cys Gly Thr Asn Thr Met Glu Arg Glu Glu Ser Glu Gln
            275                 280                 285

Thr Lys Lys Arg Glu Lys Ile His Ile Pro Glu Arg Ser Asp Glu Ala
290                 295                 300

Gln Arg Val Phe Lys Ser Ser Lys Thr Ser Ser Cys Asp Lys Ser Asp
305                 310                 315                 320

Thr Cys Phe

<210> SEQ ID NO 27
<211> LENGTH: 166
<212> TYPE: PRT
<213> ORGANISM: Homo sapiens

<400> SEQUENCE: 27

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Ala Phe Ser Met Pro Glu Val Asn Val Asp Tyr Asn Ala Ser Ser Glu
            35                  40                  45

Thr Leu Arg Cys Glu Ala Pro Arg Trp Phe Pro Gln Pro Thr Val Val
    50                  55                  60

Trp Ala Ser Gln Val Asp Gln Gly Ala Asn Phe Ser Glu Val Ser Asn
65                  70                  75                  80

Thr Ser Phe Glu Leu Asn Ser Glu Asn Val Thr Met Lys Val Val Ser
                85                  90                  95

Val Leu Tyr Asn Val Thr Ile Asn Asn Thr Tyr Ser Cys Met Ile Glu
                100                 105                 110

Asn Asp Ile Ala Lys Ala Thr Gly Asp Ile Lys Val Thr Glu Ser Glu
            115                 120                 125

Ile Lys Arg Arg Ser His Leu Gln Leu Leu Asn Ser Lys Ala Ser Leu
    130                 135                 140

Cys Val Ser Ser Phe Phe Ala Ile Ser Trp Ala Leu Leu Pro Leu Ser
145                 150                 155                 160

Pro Tyr Leu Met Leu Lys
                165

<210> SEQ ID NO 28
<211> LENGTH: 273
<212> TYPE: PRT
<213> ORGANISM: Homo sapiens

<400> SEQUENCE: 28

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
```

```
                35                  40                  45
His Val Asn Leu Gly Ala Ile Thr Ala Ser Leu Gln Lys Val Glu Asn
 50                  55                  60
Asp Thr Ser Pro His Arg Glu Arg Ala Thr Leu Leu Glu Glu Gln Leu
 65                  70                  75                  80
Pro Leu Gly Lys Ala Ser Phe His Ile Pro Gln Val Gln Val Arg Asp
                 85                  90                  95
Glu Gly Gln Tyr Gln Cys Ile Ile Ile Tyr Gly Val Ala Trp Asp Tyr
                100                 105                 110
Lys Tyr Leu Thr Leu Lys Val Lys Ala Ser Tyr Arg Lys Ile Asn Thr
                115                 120                 125
His Ile Leu Lys Val Pro Glu Thr Asp Glu Val Glu Leu Thr Cys Gln
130                 135                 140
Ala Thr Gly Tyr Pro Leu Ala Glu Val Ser Trp Pro Asn Val Ser Val
145                 150                 155                 160
Pro Ala Asn Thr Ser His Ser Arg Thr Pro Glu Gly Leu Tyr Gln Val
                165                 170                 175
Thr Ser Val Leu Arg Leu Lys Pro Pro Pro Gly Arg Asn Phe Ser Cys
                180                 185                 190
Val Phe Trp Asn Thr His Val Arg Glu Leu Thr Leu Ala Ser Ile Asp
                195                 200                 205
Leu Gln Ser Gln Met Glu Pro Arg Thr His Pro Thr Trp Leu Leu His
210                 215                 220
Ile Phe Ile Pro Ser Cys Ile Ile Ala Phe Ile Phe Ile Ala Thr Val
225                 230                 235                 240
Ile Ala Leu Arg Lys Gln Leu Cys Gln Lys Leu Tyr Ser Ser Lys Asp
                245                 250                 255
Thr Thr Lys Arg Pro Val Thr Thr Thr Lys Arg Glu Val Asn Ser Ala
                260                 265                 270
Ile

<210> SEQ ID NO 29
<211> LENGTH: 290
<212> TYPE: PRT
<213> ORGANISM: Homo sapiens

<400> SEQUENCE: 29

Met Arg Ile Phe Ala Val Phe Ile Phe Met Thr Tyr Trp His Leu Leu
 1               5                  10                  15
Asn Ala Phe Thr Val Thr Val Pro Lys Asp Leu Tyr Val Val Glu Tyr
                 20                  25                  30
Gly Ser Asn Met Thr Ile Glu Cys Lys Phe Pro Val Glu Lys Gln Leu
                 35                  40                  45
Asp Leu Ala Ala Leu Ile Val Tyr Trp Glu Met Glu Asp Lys Asn Ile
 50                  55                  60
Ile Gln Phe Val His Gly Glu Glu Asp Leu Lys Val Gln His Ser Ser
 65                  70                  75                  80
Tyr Arg Gln Arg Ala Arg Leu Leu Lys Asp Gln Leu Ser Leu Gly Asn
                 85                  90                  95
Ala Ala Leu Gln Ile Thr Asp Val Lys Leu Gln Asp Ala Gly Val Tyr
                100                 105                 110
Arg Cys Met Ile Ser Tyr Gly Gly Ala Asp Tyr Lys Arg Ile Thr Val
                115                 120                 125
Lys Val Asn Ala Pro Tyr Asn Lys Ile Asn Gln Arg Ile Leu Val Val
```

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
                195                 200                 205

Cys Thr Phe Arg Arg Leu Asp Pro Glu Glu Asn His Thr Ala Glu Leu
        210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290

<210> SEQ ID NO 30
<211> LENGTH: 534
<212> TYPE: PRT
<213> ORGANISM: Homo sapiens

<400> SEQUENCE: 30

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
                35                  40                  45

Cys Cys Ser Phe Ser Pro Glu Pro Gly Phe Ser Leu Ala Gln Leu Asn
        50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
                100                 105                 110

Arg Val Ala Asp Glu Gly Ser Phe Thr Cys Phe Val Ser Ile Arg Asp
                115                 120                 125

Phe Gly Ser Ala Ala Val Ser Leu Gln Val Ala Ala Pro Tyr Ser Lys
        130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
                180                 185                 190

Ser Gln Met Ala Asn Glu Gln Gly Leu Phe Asp Val His Ser Ile Leu
                195                 200                 205

```
Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
                260                 265                 270

Glu Pro Gly Phe Ser Leu Ala Gln Leu Asn Leu Ile Trp Gln Leu Thr
                275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
                340                 345                 350

Ser Leu Gln Val Ala Ala Pro Tyr Ser Lys Pro Ser Met Thr Leu Glu
    355                 360                 365

Pro Asn Lys Asp Leu Arg Pro Gly Asp Thr Val Thr Ile Thr Cys Ser
370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
                420                 425                 430

Asn Gly Thr Tyr Ser Cys Leu Val Arg Asn Pro Val Leu Gln Gln Asp
    435                 440                 445

Ala His Gly Ser Val Thr Ile Thr Gly Gln Pro Met Thr Phe Pro Pro
450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
                500                 505                 510

Ser Lys Thr Ala Leu Gln Pro Leu Lys His Ser Asp Ser Lys Glu Asp
    515                 520                 525

Asp Gly Gln Glu Ile Ala
    530

<210> SEQ ID NO 31
<211> LENGTH: 302
<212> TYPE: PRT
<213> ORGANISM: Homo sapiens

<400> SEQUENCE: 31

Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
                20                  25                  30

Val Glu Leu Ser Cys Ala Cys Pro Glu Gly Ser Arg Phe Asp Leu Asn
                35                  40                  45
```

```
Asp Val Tyr Val Tyr Trp Gln Thr Ser Glu Ser Lys Thr Val Val Thr
 50                      55                  60

Tyr His Ile Pro Gln Asn Ser Ser Leu Glu Asn Val Asp Ser Arg Tyr
 65                      70                  75                  80

Arg Asn Arg Ala Leu Met Ser Pro Ala Gly Met Leu Arg Gly Asp Phe
                 85                      90                  95

Ser Leu Arg Leu Phe Asn Val Thr Pro Gln Asp Glu Gln Lys Phe His
                100                     105                 110

Cys Leu Val Leu Ser Gln Ser Leu Gly Phe Gln Glu Val Leu Ser Val
                115                     120                 125

Glu Val Thr Leu His Val Ala Ala Asn Phe Ser Val Pro Val Val Ser
                130                     135                 140

Ala Pro His Ser Pro Ser Gln Asp Glu Leu Thr Phe Thr Cys Thr Ser
145                     150                     155                 160

Ile Asn Gly Tyr Pro Arg Pro Asn Val Tyr Trp Ile Asn Lys Thr Asp
                    165                     170                 175

Asn Ser Leu Leu Asp Gln Ala Leu Gln Asn Asp Thr Val Phe Leu Asn
                180                     185                 190

Met Arg Gly Leu Tyr Asp Val Val Ser Val Leu Arg Ile Ala Arg Thr
                195                     200                 205

Pro Ser Val Asn Ile Gly Cys Cys Ile Glu Asn Val Leu Leu Gln Gln
210                     215                     220

Asn Leu Thr Val Gly Ser Gln Thr Gly Asn Asp Ile Gly Glu Arg Asp
225                     230                     235                 240

Lys Ile Thr Glu Asn Pro Val Ser Thr Gly Glu Lys Asn Ala Ala Thr
                    245                     250                 255

Trp Ser Ile Leu Ala Val Leu Cys Leu Leu Val Val Val Ala Val Ala
                260                     265                 270

Ile Gly Trp Val Cys Arg Asp Arg Cys Leu Gln His Ser Tyr Ala Gly
                275                     280                 285

Ala Trp Ala Val Ser Pro Glu Thr Glu Leu Thr Gly His Val
290                     295                     300
```

ANTI-HUMAN VSIG4 ANTIBODIES AND USES THEREOF

CROSS-REFERENCE TO RELATED APPLICATIONS

This application is a continuation of International Application No. PCT/US2019/053824, filed on Sep. 30, 2019, which claims priority to and the benefit of U.S. Provisional Patent Application No. 62/738,255, filed on Sep. 28, 2018, and U.S. Provisional Patent Application No. 62/776,523, filed on Dec. 7, 2018. The disclosures of the foregoing applications are incorporated herein by reference in their entirety.

FIELD OF THE INVENTION

The present disclosure relates to antibodies and antigen-binding fragments that binds to V-Set And Immunoglobulin Domain Containing 4 (VSIG4).

BACKGROUND

Cancer remains one of the leading causes of death in the world. Recent statistics report that 13% of the world population dies from cancer. According to estimates from the International Agency for Research on Cancer (IARC), in 2012 there were 14.1 million new cancer cases and 8.2 million cancer deaths worldwide. By 2030, the global burden is expected to grow to 21.7 million new cancer cases and 13 million cancer deaths due to population growth and aging and exposure to risk factors such as smoking, unhealthy diet and physical inactivity. Further, pain and medical expenses for cancer treatment cause reduced quality of life for both cancer patients and their families. It is apparent that, above all, cancer is a disease for which it is necessary to urgently find improved treatment methods.

Macrophages are multifunctional antigen presenting cells that play a central role for our immune system and is relevant to cancer biology. In the context of cancer, tumor-associated macrophages (TAMs) infiltrate malignant tumor tissues and are known to be relevant for cancer biology, and influence of tumor progression. TAMs can be described as falling into two categories: M1 and M2. M1 macrophages are seen to have a pro-inflammatory and cytotoxic (anti-tumoral) function, while M2 macrophages are anti-inflammatory (pro-tumoral) and promote wound healing. Consistent with these functions, the TAMs, especially macrophages with the M2 phenotype, is closely associated with worse clinical prognosis in many kinds of malignant tumors. Infiltrating TAMs themselves or polarization pathway of TAMs are considered as new therapeutic targets for the therapy of malignant tumors.

SUMMARY

The present disclosure relates, at least in part, to antibodies and fragments thereof that binds to VSIG4 (V-Set And Immunoglobulin Domain Containing 4; also referred to as CRIg or Z39Ig), and methods of using such antibodies and antigen-binding fragments for treating cancer, inducing cytokine and/or chemokine secretion in macrophages, and conversion of M2 macrophages to M1 macrophages.

In one aspect, the present invention relates to an isolated humanized antibody or antigen-binding fragment includes: (a) a heavy chain CDR1 comprising the amino acid sequence of SEQ ID NO: 17, a heavy chain CDR2 comprising the amino acid sequence of SEQ ID NO: 18, a heavy chain CDR3 sequence comprising the amino acid sequence of SEQ ID NO: 19; and (b) a light chain CDR1 comprising the amino acid sequence of SEQ ID NO: 20, a light chain CDR2 comprising the amino acid sequence of SEQ ID NO: 21, and a light chain CDR3 comprising the amino acid sequence of SEQ ID NO: 22 or SEQ ID NO: 23.

In some embodiments, the antibody or antigen-binding fragment described herein may include any one of: (a) a heavy chain variable domain comprising an amino acid sequence at least 80%, 90%, 95%, 96%, 97%, 98%, or 99% identical to the amino acid sequence of SEQ ID NO: 2, SEQ ID NO: 6, SEQ ID NO: 14, or SEQ ID NO: 16; (b) a light chain variable domain comprising an amino acid sequence at least 80%, 90%, 95%, 96%, 97%, 98%, or 99% identical to the amino acid sequence of SEQ ID NO: 4, SEQ ID NO: 8, SEQ ID NO: 10, or SEQ ID NO: 12; or (c) a heavy chain variable domain comprising an amino acid sequence at least 80%, 90%, 95%, 96%, 97%, 98%, or 99% identical to the amino acid sequence of SEQ ID NO: 2, SEQ ID NO: 6, SEQ ID NO: 14, or SEQ ID NO: 16, and a light chain variable domain comprising an amino acid sequence at least 80%, 90%, 95%, 96%, 97%, 98%, or 99% identical to the amino acid sequence of SEQ ID NO: 4, SEQ ID NO: 8, SEQ ID NO: 10, or SEQ ID NO: 12.

In some embodiments, the antibody or antigen-binding fragment described herein may include any one of, a heavy chain variable domain comprising the amino acid sequence of SEQ ID NO: 2, SEQ ID NO: 6, SEQ ID NO: 14, or SEQ ID NO: 16, a light chain variable domain comprising the amino acid sequence of SEQ ID NO: 4, SEQ ID NO: 8, SEQ ID NO: 10, or SEQ ID NO: 12, or a heavy chain variable domain comprising the amino acid sequence of SEQ ID NO: 2, SEQ ID NO: 6, SEQ ID NO: 14, or SEQ ID NO: 16, and a light chain variable domain comprising the amino acid sequence of SEQ ID NO: 4, SEQ ID NO: 8, SEQ ID NO: 10, or SEQ ID NO: 12. In some embodiments, the antibody or antigen-binding fragment described herein may include a light chain CDR3 comprising the amino acid sequence of SEQ ID NO: 23.

In some embodiments, the antibody or antigen-binding fragment described herein may include a heavy chain variable domain comprising the amino acid sequence of SEQ ID NO: 2 and a light chain variable domain comprising the amino acid sequence of SEQ ID NO: 4. In some embodiments, the antibody or antigen-binding fragment described herein may include a heavy chain variable domain comprising the amino acid sequence of SEQ ID NO: 6 and a light chain variable domain comprising the amino acid sequence of SEQ ID NO: 8. In some embodiments, the antibody or antigen-binding fragment may include a heavy chain variable domain comprising the amino acid sequence of SEQ ID NO: 6 and a light chain variable domain comprising the amino acid sequence of SEQ ID NO: 10. In some embodiments, the antibody or antigen-binding fragment may include a heavy chain variable domain comprising the amino acid sequence of SEQ ID NO: 6 and a light chain variable domain comprising the amino acid sequence of SEQ ID NO: 12. In some embodiments, the antibody or antigen-binding fragment described herein may include a heavy chain variable domain comprising the amino acid sequence of SEQ ID NO: 14 and a light chain variable domain comprising the amino acid sequence of SEQ ID NO: 10. In some embodiments, the antibody or antigen-binding fragment described herein may include a heavy chain variable domain comprising the amino acid sequence of SEQ ID NO: 16 and a light chain variable domain comprising the amino acid sequence of SEQ ID NO: 12.

In some embodiments, the antibody or antigen-binding fragment described herein has a binding affinity ($K_D$) for a human V-Set And Immunoglobulin Domain Containing 4 (VSIG4) molecule of $1 \times 10^{-7}$ to $1 \times 10^{-9}$. In some embodiments, the antibody or antigen-binding fragment described herein has a binding affinity ($K_D$) for a VSIG4 molecule of about $7.156 \times 10^{-8}$ to about $7.636 \times 10^{-9}$. In some embodiments, the antibody or antigen-binding fragment described herein has a binding affinity ($K_D$) for a VSIG4 molecule of about $7.156 \times 10^{-8}$, about $7.636 \times 10^{-9}$, about $7.952 \times 10^{-9}$, about $8.226 \times 10^{-9}$, or about $8.688 \times 10^{-9}$.

In another aspect, the present invention relates to a nucleic acid molecule encoding any one of the antibody or antigen-binding fragments described herein.

In another aspect, the present invention relates to a recombinant vector including any one of the nucleic acid molecules described herein. In some embodiments, the recombinant vector described herein contains the nucleic acid molecule described herein that is operatively linked to a promoter. In some embodiments, the recombinant vector includes two separate vectors, each comprising the nucleic acid sequence corresponding to the heavy chain and the light chain of the antibody or antigen-binding fragment provided herein.

In another aspect, the present invention provides a host cell including the nucleic acid molecule or the recombinant vector described herein. In some embodiments, the host cell is a mammalian cell, a yeast cell, or a bacterial cell. In some embodiments, the host cell is a cell selected from the group consisting of E. coli, P. pastoris, Sf9, COS, HEK293, Expi293, CHO-S, CHO-DG44, CHO-K1, and a mammalian lymphocyte. In some embodiments, the host cell is the Expi293 cell. In another aspect, the present invention relates to a pharmaceutical composition including: any one of the antibody or antigen-binding fragments described herein, any one of the nucleic acid molecules described herein, any one of the recombinant vectors described herein, or any one of the host cells described herein; and a pharmaceutically acceptable carrier.

By way of further example, in another aspect, the present invention relates to a method of treating a subject in need thereof, the method comprising the steps of: (a) administering to the subject a composition that comprises or delivers any one of the antibody or antigen-binding fragments described herein, any one of the nucleic acid molecules described herein, any one of the recombinant vectors described herein, or any one of the host cells described herein, thereby treating a disease or a condition. In some embodiments, the subject has, or is at risk for developing, cancer. In some embodiments, the cancer is selected from a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, and prostate cancer.

In some embodiments, the subject has been administered or will be administered one or more additional anticancer therapies selected from ionizing radiation, a chemotherapeutic agent, an antibody agent, and a cell-based therapy, such that the subject receives treatment with both. For example, in some embodiments, the one or more additional anticancer therapies can include an immune checkpoint inhibitor, IL-12, GM-CSF, an anti-CD4 agent, cisplatin, fluorouracil, doxorubicin, irinotecan, paclitaxel, indoleamine 2,3-di oxygenase-1 (IDO1) inhibitor, or cyclophosphamide.

In yet another aspect, the present invention also relates to a method of increasing secretion of cytokines or chemokines in M2 macrophages, the method including contacting the M2 macrophages with any one of the antibody or antigen-binding fragments described herein.

In yet another aspect, the present invention relates to a method of inducing CD8$^+$ T cell proliferation, the method including: (a) contacting an M2 macrophage with any one of the antibody or antigen-binding fragments described herein; and (b) co-incubating the M2 macrophage with CD8$^+$ T cells.

In yet another aspect, the present invention also relates to a method of converting an M2 macrophage into an M1 macrophage, the method including contacting the M2 macrophage with any one of the antibody or antigen-binding fragments described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 2A shows sequence alignment of VSIG4 with various human B7 family of proteins.

FIG. 12 is a set of microscope images of M1 and M2 macrophages showing morphological differences after conversion of M2 macrophages into M1 macrophages by EU103.2 antibody.

FIGS. 15A-15C are sets of graphs showing the anti-tumor activities of anti-VSIG4 antibody in three different mouse tumor models.

FIG. 17C is a set of graphs showing activation status of T cells and MDSCs in TDLNs in the absence of VSIG4 signaling.

FIG. 17D is a set of graphs showing activation status of T cells and MDSCs in TDLNs in the absence of VSIG4 signaling.

FIGS. 21A and 21B are schematic diagrams showing expression vectors used to clone and express humanized anti-VSIG4 antibodies.

FIG. 22 is a HPLC plot showing protein profile of A1 antibody (EU103_T01.01).

FIG. 23 is a HPLC plot showing protein profile of A2 antibody (EU103_T01.02).

FIG. 26A is a set of FACS data showing decreased expression of CD163 in M2 macrophages treated with A1 or A2 antibodies.

FIG. 26B is a graph showing decreased expression of CD163 in M2 macrophages treated with A1 or A2 antibodies.

FIGS. 31A-31C show the anti-tumor effect of A1 and A2 antibodies in a humanized mouse model.

FIGS. 32A-32C show macrophage conversion with A2 antibodies in vivo.

FIGS. 35A-35D show the anti-tumor effect of A2 and A2.3 antibodies in a humanized mouse model.

FIG. 41A shows a targeting vector construct generated for use in homologous recombination in ES cells. E1 and E2 indicate exon 1 and 2 of the CRIg gene. VSIG K/O mice are generated by homologous recombination replacing exon 1 with the neomycin resistance gene.

FIG. 41B shows southern blotting results confirming homologous recombination of the CRIg allele in heterozygous female offspring from ES cell clone 1 and 2 (C1, C2) chimeric mice bred to WT mice.

FIG. 41C shows a graph comparing the numbers of leukocytes in the peripheral blood of WT and K/O male and female mice. Total blood cell counts were determined using a hematocytometer.

DETAILED DESCRIPTION

Figure 1:
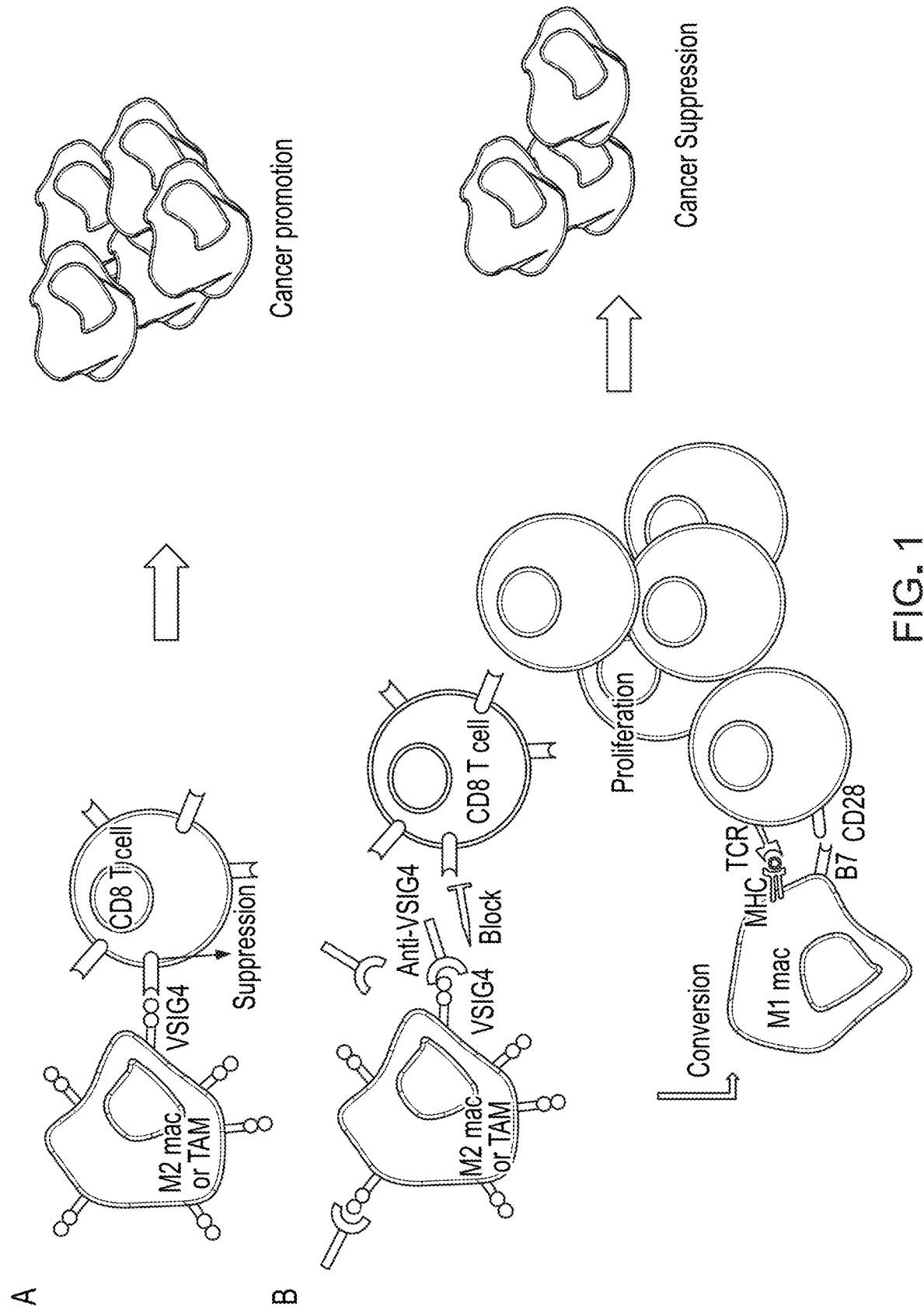
FIG. 1 is a schematic diagram illustrating mechanism of how administration of anti-VSIG4 antibody to macrophages result in conversion of M2 macrophages to M1 macrophages, which results in proliferation of CD8$^+$ T cells and subsequent suppression of cancer.

The present invention is based, at least in part, on the discovery that inhibition of VSIG4 interaction with CD8+ T cells using certain anti-VSIG4 antibodies result in proliferation of CD8+ T cells, which can lead to suppression of cancer.

As used herein, the term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intraarterial, intradermal, intragastric, intramedullary, intramuscular, intranasal, intraperitoneal, intrathecal, intravenous, intraventricular, within a specific organ (e.g. intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

As used herein, the term "affinity" typically refers to a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

As used herein, the term "affinity maturation" refers to a process in which an antibody is evolved from a reference antibody (also referred to herein as a template or parent antibody), typically by mutation of one or more amino acid residues, to have increased activity for a target antigen than a corresponding form of the reference antibody has for the same target antigen. Hence, the evolved antibody is optimized compared to the reference or template antibody. As used herein, the term "affinity matured antibody" typically refers to an antibody that has an increased activity for a target antigen relative to a reference antibody. In some embodiments, the affinity matured antibody exhibits increased binding to the target antigen compared to the reference or parent antibody. Typically, the affinity matured antibody binds to the same epitope as the reference antibody.

As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); humabodies, VHHs; Anticalins®; Nanobodies® minibodies; BiTE®s; ankyrin repeat proteins or DARPINs®; Avimers®; DARTs; TCR-like antibodies; Adnectins®; Affilins®; Trans-Bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.].

As used herein, an "antibody fragment" refers to a portion of an antibody or antibody agent as described herein, and typically refers to a portion that includes an antigen-binding portion or variable region thereof. An antibody fragment may be produced by any means. For example, in some embodiments, an antibody fragment may be enzymatically or chemically produced by fragmentation of an intact antibody or antibody agent. Alternatively, in some embodiments, an antibody fragment may be recombinantly produced (i.e., by expression of an engineered nucleic acid sequence. In some embodiments, an antibody fragment may be wholly or partially synthetically produced. In some embodiments, an antibody fragment (particularly an antigen-binding antibody fragment) may have a length of at least about 50, 60, 70, 80, 90, 100, 110, 120, 130, 140, 150, 160, 170, 180, 190 amino acids or more, in some embodiments at least about 200 amino acids.

As used herein, the term "binding" typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

As used herein, the terms "cancer", "malignancy", "neoplasm", "tumor", and "carcinoma" typically refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

As used herein, the term "CDR" refers to a complementarity determining region within an antibody variable region. There are three CDRs in each of the variable regions of the heavy chain and the light chain, which are designated CDR1, CDR2 and CDR3, for each of the variable regions. A "set of CDRs" or "CDR set" refers to a group of three or six CDRs that occur in either a single variable region capable of binding the antigen or the CDRs of cognate heavy and light chain variable regions capable of binding the antigen. Certain systems have been established in the art for defining CDR boundaries (e.g., Kabat, Chothia, etc.); those skilled in the art appreciate the differences between and among these systems and are capable of understanding CDR boundaries to the extent required to understand and to practice the claimed invention.

As used herein, the term "chemotherapeutic agent" has its art-understood meaning referring to one or more pro-apoptotic, cytostatic and/or cytotoxic agents, for example specifically including agents utilized and/or recommended for use in treating one or more diseases, disorders or conditions associated with undesirable cell proliferation. In many embodiments, chemotherapeutic agents are useful in the treatment of cancer. In some embodiments, a chemotherapeutic agent may be or comprise one or more alkylating agents, one or more anthracyclines, one or more cytoskeletal disruptors (e.g. microtubule targeting agents such as taxanes, maytansine and analogs thereof, of), one or more epothilones, one or more histone deacetylase inhibitors HDACs), one or more topoisomerase inhibitors (e.g., inhibitors of topoisomerase I and/or topoisomerase II), one or more kinase inhibitors, one or more nucleotide analogs or nucleotide precursor analogs, one or more peptide antibiotics, one or more platinum-based agents, one or more retinoids, one or more vinca alkaloids, and/or one or more analogs of one or more of the following (i.e., that share a relevant anti-proliferative activity). In some particular embodiments, a chemotherapeutic agent may be or comprise one or more of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIBO15, BT062, SGN-75, SGN-CD19A, AMG-172, AMG-595, BAY-94-9343, ASG-5ME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine.

As used herein, the term "combination therapy" refers to those situations in which a subject is simultaneously exposed to two or more therapeutic regimens (e.g., two or more therapeutic agents). In some embodiments, the two or more therapeutic regimens may be administered simultaneously. In some embodiments, the two or more therapeutic regimens may be administered sequentially (e.g., a first regimen administered prior to administration of any doses of a second regimen). In some embodiments, the two or more therapeutic regimens are administered in overlapping dosing regimens. In some embodiments, administration of combination therapy may involve administration of one or more therapeutic agents or modalities to a subject receiving the other agent(s) or modality.

As used herein, the term "framework" or "framework region" refers to the sequences of a variable region minus the CDRs. Because a CDR sequence can be determined by different systems, likewise a framework sequence is subject to correspondingly different interpretations. The six CDRs divide the framework regions on the heavy and light chains into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, FR1, for example, represents the first framework region closest to the amino terminal end of the variable region and 5' with respect to CDR1, and FRs represents two or more of the sub-regions constituting a framework region.

As used herein, the term "humanized" is commonly used to refer to antibodies (or antibody components) whose amino acid sequence includes $V_H$ and $V_L$ region sequences from a reference antibody raised in a non-human species (e.g., a mouse), but also includes modifications in those sequences relative to the reference antibody intended to render them more "human-like", i.e., more similar to human germline variable sequences. In some embodiments, a "humanized" antibody (or antibody component) is one that immunospecifically binds to an antigen of interest and that has a framework (FR) region having substantially the amino acid sequence as that of a human antibody, and a complementary determining region (CDR) having substantially the amino acid sequence as that of a non-human antibody. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor immunoglobulin) and all or substantially all of the framework regions are those of a human immunoglobulin consensus sequence. In some embodiments, a humanized antibody also comprises at least a portion of an immunoglobulin constant region (Fc), typically that of a human immunoglobulin constant region. In some embodiments, a humanized antibody contains both the light chain as well as at least the variable domain of a heavy chain. The antibody also may include a $C_H1$, hinge, $C_H2$, $C_H3$, and, optionally, a $C_H4$ region of a heavy chain constant region.

As used herein, the term "in vitro" refers to events that occur in an artificial environment, e.g., in a test tube or reaction vessel, in cell culture, etc., rather than within a multi-cellular organism. As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

As used herein, the term "isolated" refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 9'7%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced. As used herein, the term "$K_D$" refers to the dissociation constant of a binding agent (e.g., an antibody or binding component thereof) from a complex with its partner (e.g., the epitope to which the antibody or binding component thereof binds).

As used herein, the term "macrophage" refers to a cell of the monocyte/macrophage lineage which is found in the spleen or has differentiated into a tissue macrophage. These cells include follicular dendritic cells (FDC), dendritic cells, Langerhans cells, as well as other tissue macrophages. Macrophages are phagocytes and antigen presenting cells that differentiate from monocytes in circulating peripheral blood. They play an important role in both innate and adaptive immunity by activating T lymphocytes. Macrophages that activate Th1 T lymphocytes provide an inflammatory response and are denoted M1 macrophages. M1 macrophages, also referred to as "killer macrophages," inhibit cell proliferation, cause tissue damage, and are aggressive against bacteria. Macrophages that activate Th2 T lymphocytes provide an anti-inflammatory response and are denoted M2 macrophages. M2 macrophages, also referred to as "repair macrophages," promote cell proliferation and tissue repair and are anti-inflammatory. As used herein, the term "tumor associated macrophages" (TAMs) generally refers to macrophages that exist in the microenvironment of a cancer, for example, a tumor.

As used herein, the term "operably linked" refers to a juxtaposition wherein the components described are in a relationship permitting them to function in their intended manner. A control element "operably linked" to a functional element is associated in such a way that expression and/or activity of the functional element is achieved under conditions compatible with the control element. In some embodiments, "operably linked" control elements are contiguous (e.g., covalently linked) with the coding elements of interest; in some embodiments, control elements act in trans to or otherwise at a from the functional element of interest.

As used herein, the term "pharmaceutical composition" refers to a composition in which an active agent is formulated together with one or more pharmaceutically acceptable carriers. In some embodiments, the composition is suitable for administration to a human or animal subject. In some embodiments, the active agent is present in unit dose amount appropriate for administration in a therapeutic regimen that shows a statistically significant probability of achieving a predetermined therapeutic effect when administered to a relevant population. As used herein, the term "polypeptide" generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

As used herein, the term "prevent" or "prevention" when used in connection with the occurrence of a disease, disorder, and/or condition, refers to reducing the risk of developing the disease, disorder and/or condition and/or to delaying onset and/or severity of one or more characteristics or symptoms of the disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition.

As used herein, the term "recombinant" is intended to refer to polypeptides that are designed, engineered, prepared, expressed, created, manufactured, and/or or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc) that is transgenic for or otherwise has been manipulated to express a gene or genes, or gene components that encode and/or direct expression of the polypeptide or one or more component(s), portion(s), element(s), or domain(s) thereof and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc).

As used herein, the term "specific binding" refers to an ability to discriminate between possible binding partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. For example, in some embodiments, term "therapeutically effective amount", refers to an amount which, when administered to an individual in need thereof in the context of inventive therapy, will block, stabilize, attenuate, or reverse a cancer-supportive process occurring in said individual, or will enhance or increase a cancer-suppressive process in said individual. In the context of cancer treatment, a "therapeutically effective amount" is an amount which, when administered to an individual diagnosed with a cancer, will prevent, stabilize, inhibit, or reduce the further development of cancer in the individual. A particularly preferred "therapeutically effective amount" of a composition described herein reverses (in a therapeutic treatment) the development of a malignancy such as a pancreatic carcinoma or helps achieve or prolong remission of a malignancy. A therapeutically effective amount administered to an individual to treat a cancer in that individual may be the same or different from a therapeutically effective amount administered to promote remission or inhibit metastasis. As with most cancer therapies, the therapeutic methods described herein are not to be interpreted as, restricted to, or otherwise limited to a "cure" for cancer; rather the methods of treatment are directed to the use of the described compositions to "treat" a cancer, i.e., to effect a desirable or beneficial change in the health of an individual who has cancer. Such benefits are recognized by skilled healthcare providers in the field of oncology and include, but are not limited to, a stabilization of patient condition, a decrease in tumor size (tumor regression), an improvement in vital functions (e.g., improved function of cancerous tissues or organs), a decrease or inhibition of further metastasis, a decrease in opportunistic infections, an increased survivability, a decrease in pain, improved motor function, improved cognitive function, improved feeling of energy (vitality, decreased malaise), improved feeling of well-being, restoration of normal appetite, restoration of healthy weight gain, and combinations thereof. In addition, regression of a particular tumor in an individual (e.g., as the result of treatments described herein) may also be assessed by taking samples of cancer cells from the site of a tumor such as a pancreatic adenocarcinoma (e.g., over the course of treatment) and testing the cancer cells for the level of metabolic and signaling markers to monitor the status of the cancer cells to verify at the molecular level the regression of the cancer cells to a less malignant phenotype. For example, tumor regression induced by employing the methods of this invention would be indicated by finding a decrease in any of the pro-angiogenic markers discussed above, an increase in anti-angiogenic markers described herein, the normalization (i.e., alteration toward a state found in normal individuals not suffering from cancer) of metabolic pathways, intercellular signaling pathways, or intracellular signaling pathways that exhibit abnormal activity in individuals diagnosed with cancer. Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

As used herein in the context of molecules, e.g., nucleic acids, proteins, or small molecules, the term "variant" refers to a molecule that shows significant structural identity with a reference molecule but differs structurally from the reference molecule, e.g., in the presence or absence or in the level of one or more chemical moieties as compared to the reference entity. In some embodiments, a variant also differs functionally from its reference molecule. In general, whether a particular molecule is properly considered to be a "variant" of a reference molecule is based on its degree of structural identity with the reference molecule. As will be appreciated by those skilled in the art, any biological or chemical reference molecule has certain characteristic structural elements. A variant, by definition, is a distinct molecule that shares one or more such characteristic structural elements but differs in at least one aspect from the reference molecule. To give but a few examples, a polypeptide may have a characteristic sequence element comprised of a plurality of amino acids having designated positions relative to one another in linear or three-dimensional space and/or contributing to a particular structural motif and/or biological function; a nucleic acid may have a characteristic sequence element comprised of a plurality of nucleotide residues having designated positions relative to on another in linear or three-dimensional space. In some embodiments, a variant polypeptide or nucleic acid may differ from a reference polypeptide or nucleic acid as a result of one or more differences in amino acid or nucleotide sequence. In some embodiments, a variant polypeptide or nucleic acid shows an overall sequence identity with a reference polypeptide or nucleic acid that is at least 85%, 86%, 87%, 88%, 89%, 90%, 91%, 92%, 93%, 94%, 95%, 96%, 97%, or 99%. In some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid.

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., *Molecular Cloning: A Laboratory Manual* ($2^{nd}$ ed., Cold Spring Harbor Laboratory Press, Cold Spring Harbor, N.Y. (1989)), which is incorporated herein by reference for any purpose.

Macrophages in Cancer

Macrophages are phagocytes and antigen presenting cells that differentiate from monocytes in circulating peripheral blood. These cells have been known to play an important role in both innate and adaptive immunity by activating T lymphocytes. Macrophages that activate Th1 T lymphocytes provide an inflammatory response and are denoted M1 macrophages. M1 macrophages, also referred to as "killer macrophages," inhibit cell proliferation, cause tissue damage, and are aggressive against bacteria. Macrophages that activate Th2 T lymphocytes provide an anti-inflammatory response and are denoted M2 macrophages. M2 macrophages, also referred to as "repair macrophages," promote cell proliferation and tissue repair and are anti-inflammatory.

While macrophages are formed through differentiation of monocytes, monocytes mature into either M1 ($CD 68^+$ and $CD80^+$) or M2 ($CD68^+$ and $CD163^+$) macrophages depending on the cytokines and growth factors that cause them to differentiate. Lipopolysaccharide (LPS) and interferon gamma (IFNγ) activate monocytes to differentiate into M1 macrophages that secrete high levels of interleukin-1 (IL-1) and interleukin-12 (IL-12) and low levels of interleukin-10 (IL-10). Alternatively, interleukin-4 (IL-4), IL-10, interleukin-1 receptor antagonist (IL-1ra) and transforming growth factor beta (TGFβ) activate monocytes to differentiate into M2 macrophages that secrete high levels of IL-10, TGFβ, and insulin-like growth factor 1 (IGF-1) and low levels of IL-12.

The role of immunity in oncogenesis has been increasingly appreciated. Since macrophages are known to play important roles in both innate and adaptive immunity and they have been recognized as key components of tumors and their microenvironment. Tumor associated macrophages (TAMs) generally refer to macrophages that exist in the microenvironment of a cancer. The role of tumor-associated macrophages (TAMs) in the growth, invasion and metastasis of tumors has been extensively investigated and it is known that TAMs display a broad spectrum of phenotypes, ranging from the M1-like phenotype in early stages of selected tumors to the M2-like phenotype in most advanced tumors. As evidence to its role in promoting tumorigenesis, the M2 macrophages display the characteristic phenotype of elevated expression of IL-10, IL4, MMP, and VEGF, but decreased expression of pro-inflammatory cytokines and cytotoxic iNOs and ROIs, which are implicated in tumoricidal activities. Besides its intrinsic function in promoting tumorigenesis, TAMs also contribute to the suppression of anti-tumor immunity by alternating T-cell responses and balance in the tumor microenvironment. Other than promoting cell proliferation playing an anti-inflammatory role, in cancer, M2 macrophages can induce vascularization in an area of a tumor. Therefore, in such scenarios it would be useful to inhibit the M2 polarization of macrophages and induce the M1 polarization of macrophages, which are known to attack tumor cells.

VSIG4

Figure 2A:
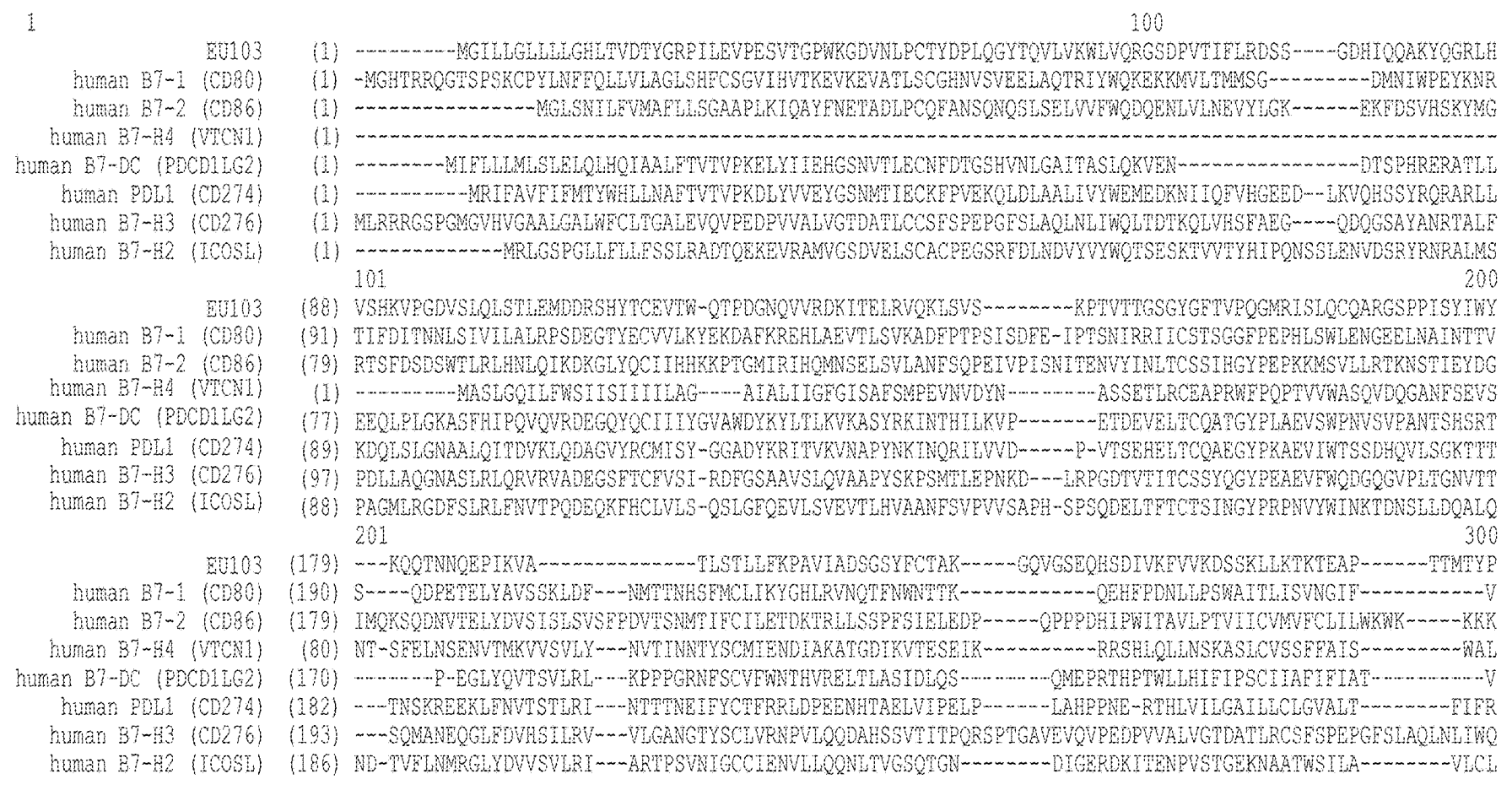
Figure 2B:
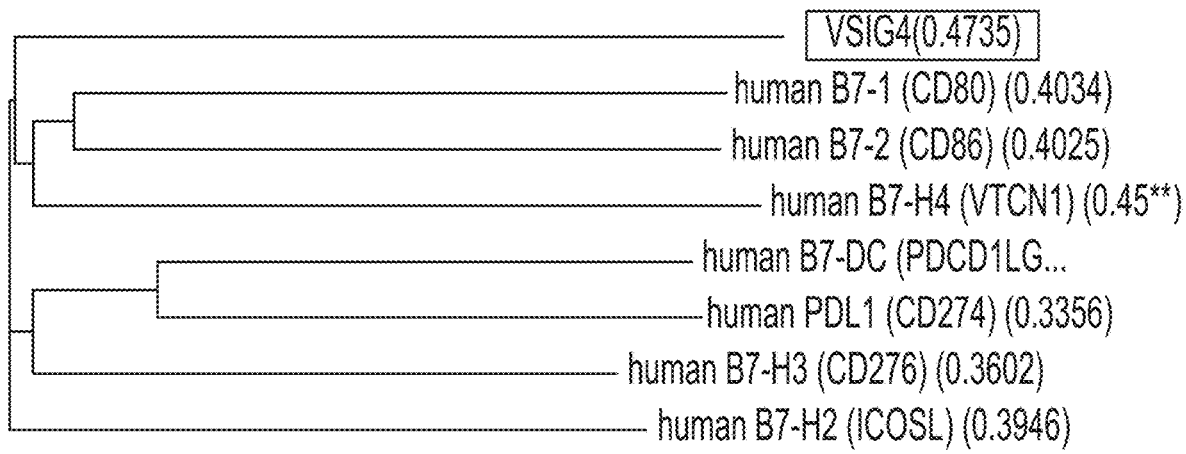
FIG. 2B is a phylogenic tree showing evolutionary relationship between VSIG4 and various human B7 family of proteins.

VSIG4 (V-set immunoglobulin-domain-containing 4) is a B7 family-related membrane protein belonging to complement receptor of the immunoglobulin superfamily (CRIg) which is known to negatively regulate $CD8^+$ T cell proliferation and IL-2 production by binding iC3b and C3b. The expression of VSIG4 is restricted to tissue macrophages, including peritoneal macrophages and liver-residential Kupffer cells. FIGS. 2A and 2B shows VSIG4's relationship (homology and phylogeny relationships, respectively) with other B7 family of proteins (VSIG4 is referred to as EU103 in FIGS. 2A and 2B). FIG. 2A shows amino acid sequence alignment of VSIG4 with various other B7 family proteins. FIG. 2B shows evolutionary relationship between VSIG4 and other B family proteins.

Anti-VSIG4 Antibody to Treat Cancer

Tumor associated macrophages (TAM) are the key cells that create an immunosuppressive tumor microenvironment (TME) providing multiple targets for immunotherapies. Macrophages are also known to be highly plastic and can also repolarize and acquire an anti-tumorigenic M1-like phenotype.

Tumor-associated macrophages (TAMs) are typically known for their protumoral functions such as promotion of cancer cell motility, metastasis formation and angiogenesis. Formation of TAMs is dependent on microenvironmental factors which are present in developing tumors. TAMs are abundant in many cancers, especially in the tumor microenvironment, and often display an immune-suppressive M2-like phenotype that fosters tumor growth and promotes resistance to therapy. TAMs also produce immunosuppressive cytokines like IL-10, TGFβ and PGE2, very small amount of NO or ROI and low levels of inflammatory cytokines such as IL-12, IL-10, TNFα, and IL-6. Conversion of macrophages to TAMs result in reduced ability to present tumor-associated antigens and stimulate anti-tumor functions of T and NK cells. Further, TAMs are not able to lyse tumor cells. Therefore, targeting of TAM is a new therapeutic strategy for suppressing or treating cancer, for example by delivering agents to either alter the recruitment and distribution of TAMs, depleting existing TAMs, or inducing the re-education (or converting) of TAMs from an M2 to an M1 phenotype.

The present disclosure is based on the discovery that VSIG4 expressing M2 macrophages can be treated with humanized anti-VSIG4 antibodies to convert (or repolarize)

the M2 macrophages to tumor-suppressive M1 macrophages, thereby inducing CD8⁺ T cell proliferation and proinflammatory cytokine production leading to tumor suppression. Further, the use of anti-VSIG4 antibodies can suppress cancer effectively by target both (1) conversion of M2 macrophages into M1 macrophages, and (2) inducing CD8⁺ T cell proliferation and proinflammatory cytokine production, thereby influencing the tumor microenvironment itself. This approach of using an anti-VSIG4 antibody to suppress cancer is superior to other therapies that only induce T cell proliferation or only block macrophages tumor-assisting activities. See FIG. 1 (schematically showing the effects of anti-VSIG4 antibodies on macrophage function, its effects on T-cell proliferation, and subsequent cancer suppression.)

Humanization of Mouse Antibody

Although monoclonal antibodies can be rapidly produced by the mouse immune system for biological studies, in a clinical setting, the use of these murine antibodies can result in a human anti-mouse antibody response (HAMA). While chimeric antibodies can reduce anti-IgG responses in human, murine variable domains may still have provocative T-cell epitope content, necessitating "humanization" of their framework regions.

Classical antibody humanization generally begins by transferring all six murine complementarity determining regions (CDRs) onto a human antibody framework (Jones et al., Nature 321, 522-525 (1986)). These CDR-grafted antibodies generally do not retain their original affinity for antigen binding, and in fact, affinity is often severely impaired. Besides the CDRs, certain non-human framework residues must also be incorporated into the variable domains to maintain proper CDR conformation (Chothia et al., Nature 342:877 (1989)). The incorporation of murine residues at key positions in the human frameworks to restore function is generally referred to as "back-mutations." Back-mutations can support structural conformation of the grafted CDRs and restore antigen binding and affinity. Many of the framework positions that are likely to affect affinity have been identified, thus structural modeling to select new residues in a stepwise fashion can generally lead to variants with restored antigen binding. Alternatively, phage antibody libraries targeted at these residues can also be used to enhance and speed up the affinity maturation process (Wu et al., *J. Mol. Biol.* 294:151-162 (1999) and Wu, H., *Methods in Mol. Biol.* 207:197-212 (2003)).

Antibody Affinity Maturation

Affinity maturation is a process by which $T_{FH}$ cell-activated B cells produce antibodies with increased affinity for a specific antigen during the course of an immune response. With repeated exposures to the same antigen, a host will produce antibodies of successively greater affinities. A secondary response can elicit antibodies with several fold greater affinity than in a primary response. Affinity maturation is an important strategy in antibody optimization to generate safe and efficacious second-generation therapeutics. Classically, therapeutic antibodies are obtained by immunizing mice or transgenic animals expressing human immunoglobulin genes with the desired antigen. Antigen-stimulated immune cells from these animals were transformed into hybridomas and subsequently screened to identify monoclonal antibodies with low nanomolar affinities for their target antigen. In vivo, natural affinity maturation by the immune system takes place by somatic hypermutation and clonal selection, while in vitro, in the laboratory affinity maturation, can be obtained by mutation and selection. Further, other methods for affinity maturation besides those using TFH cell-activated B cells are known in the art, and are within the scope of the present disclosure.

EXAMPLES

The invention is further described in the following examples, which do not limit the scope of the invention described in the claims.

Methods and Materials

The following methods and materials were used for the experiments described in the Examples.

CD14⁺ Monocyte Isolation from Human PBMC

Figure 5:
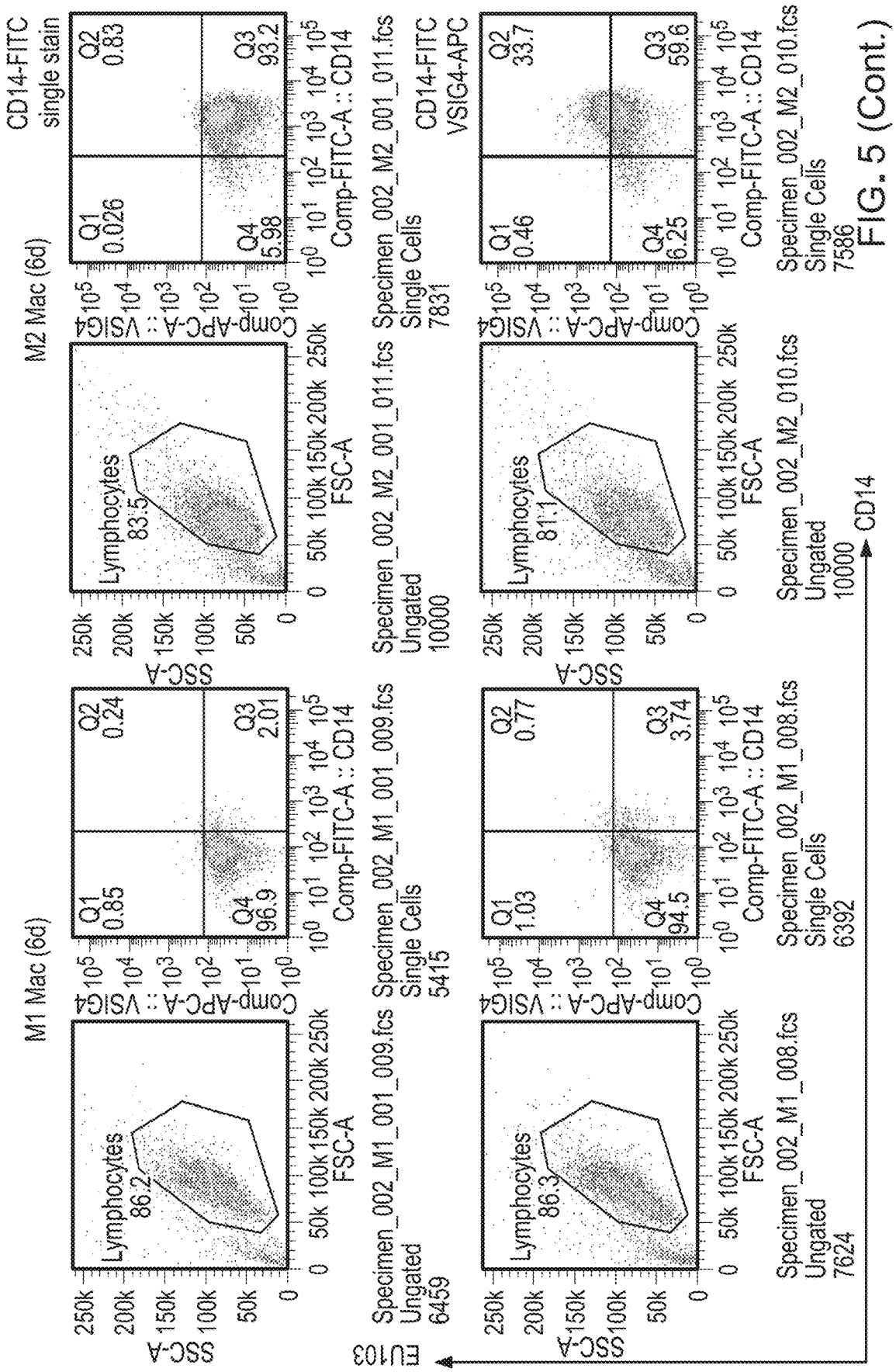
FIG. 5 shows light microscope images of M1 and M2 macrophages (top left and top right, respectively), and FACS analysis data showing expression of VSIG4 in M1 and M2 macrophages.

Differentiation of macrophages into M1 or M2 macrophages was performed by isolating PBMC from subjects and incubating the macrophages in 50 ng/ml hGM-CSF for 6 days to convert to M1 macrophages or incubating the macrophages in 100 ng/ml M-CSF for 6d to convert to M2 macrophages (FIG. 5).

Figure 6:
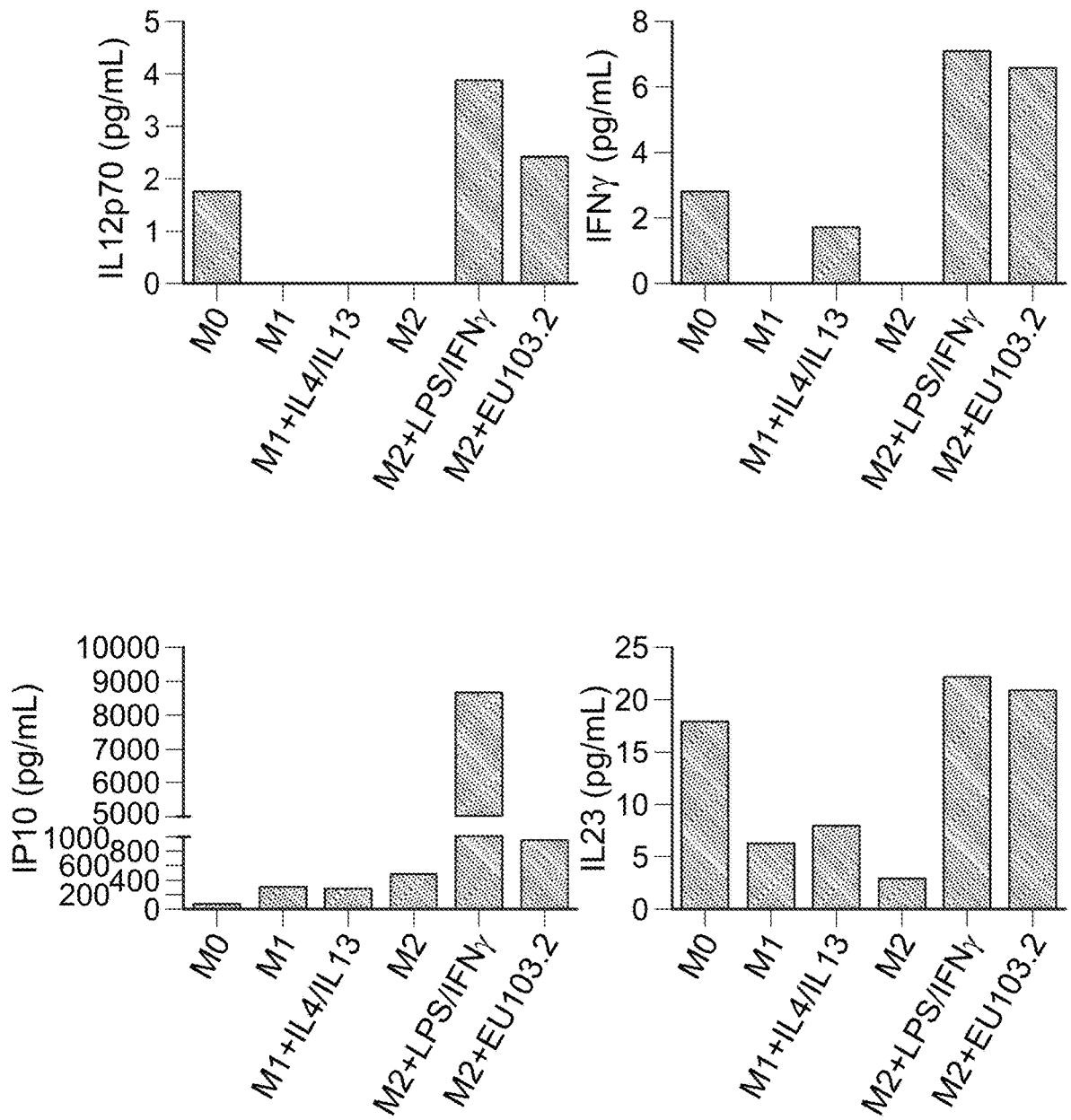
FIG. 6 is a set of graphs showing induction of proinflammatory cytokines and chemokines in M1 and M2 macrophages by EU103.2.
Figure 7:
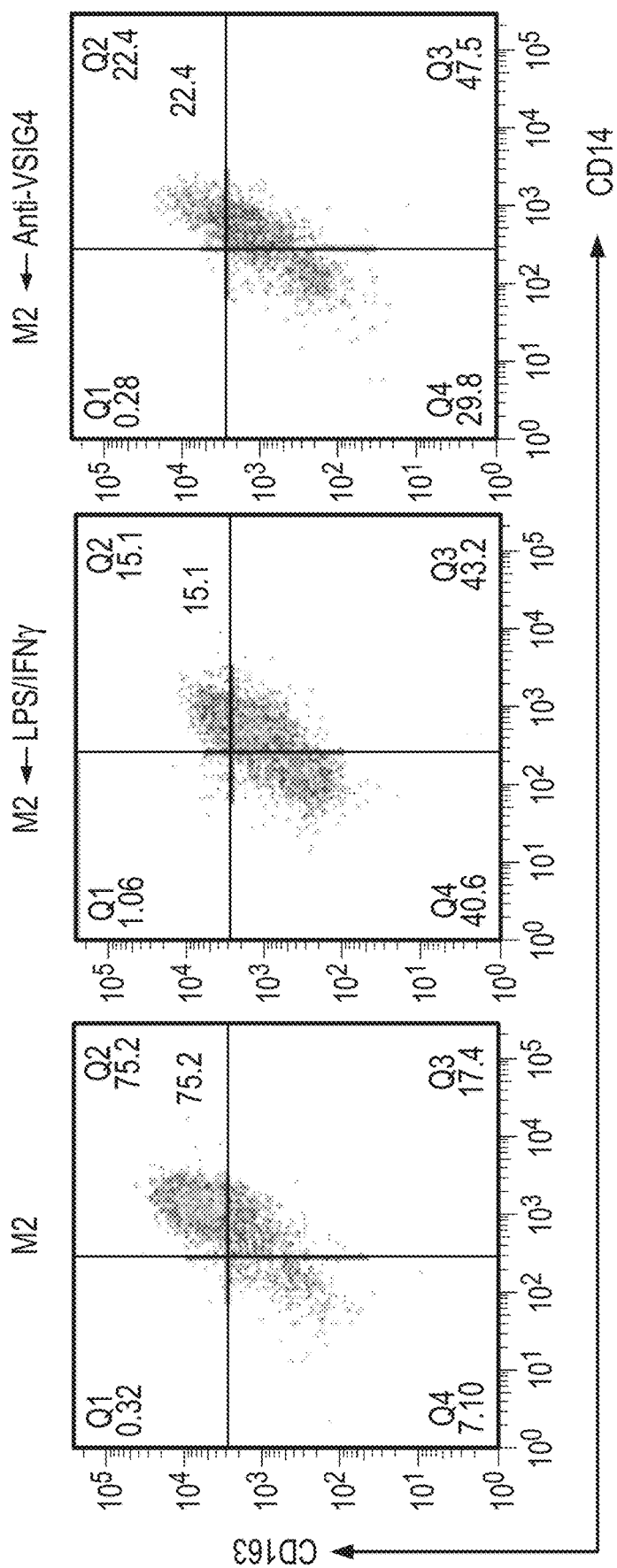
FIG. 7 is a set of FACS data showing decreased expression of CD163 in M2 macrophages treated with EU103.2.

Conversion of macrophages to M1 or M2 macrophages were confirmed by phenotype check (FIGS. 6 and 7).

Subsequent conversion of M1 or M2 macrophages to M1 macrophages was performed by incubating the macrophages in LPS(100 ng/ml)+IFNγ(100 ng/ml) or 500 ng/ml anti-VSIG4 antibody (EU103.2) for 24 hours (FIG. 12).

Conversion of M1 or M2 macrophages into M2 macrophages was performed by incubating the macrophages in 20 ng/ml IL-4 for 24 h (FIG. 12).

Humanized Anti-VSIG4 Antibody-EU103.2 Antibody

Figure 4A:
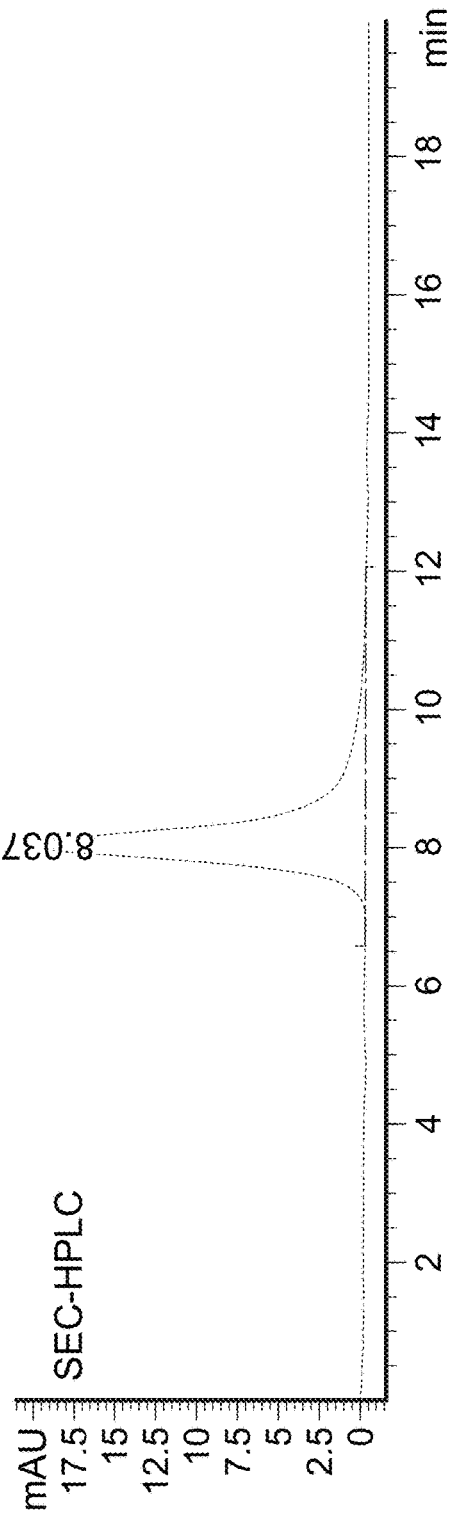
FIG. 4A is a HPLC plot showing protein profile of EU103.2 antibody.
Figure 4B:
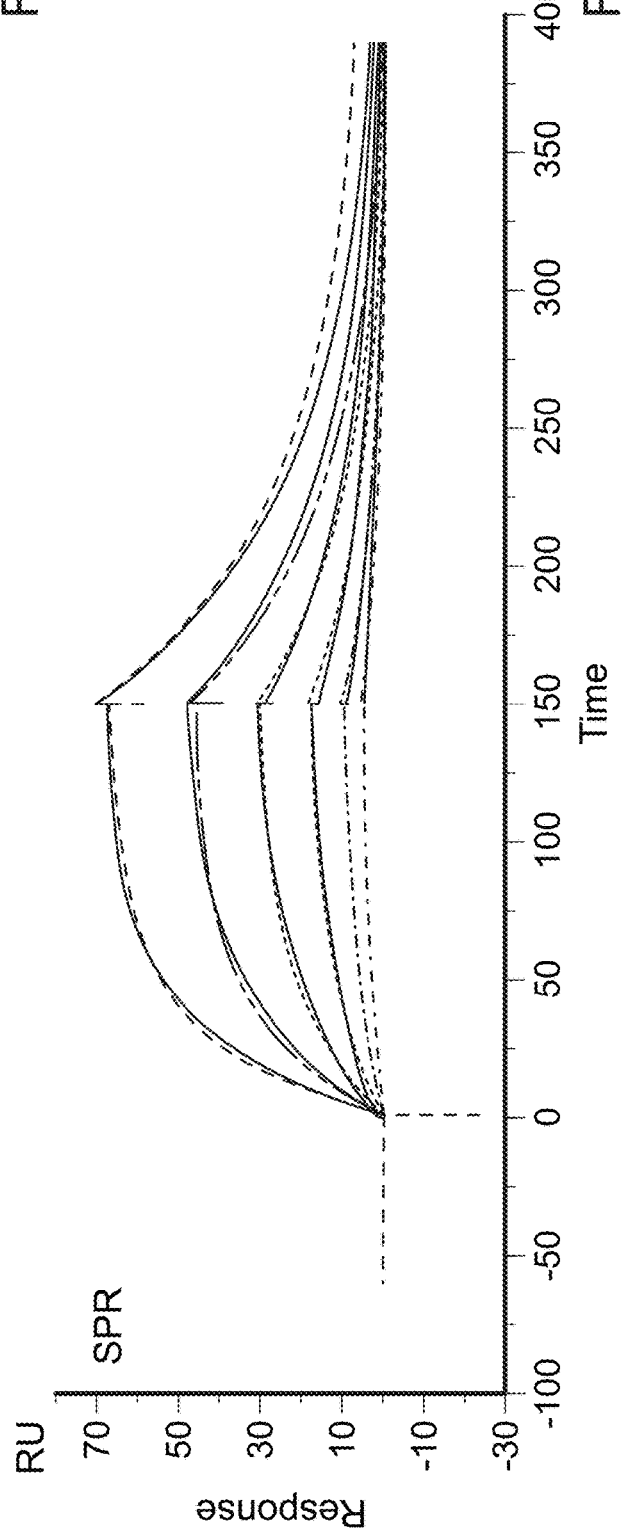
FIG. 4B is a surface plasmon resonance data showing binding of EU103.2 antibody to VSIG4.

EU103.2 antibody is a humanized anti-VSIG4 antibody generated from the mouse anti-VSIG4 antibody mu6H8. FIGS. 4A and 4B show biochemical characterization of EU103.2 antibody using size-exclusion HPLC (FIG. 4A) and surface plasmon resonance experiments, showing binding of VSIG4 to EU103.2 Antibody (FIG. 4B). A summary of EU103.2 antibody purification data is shown in TABLE 1, below.

TABLE 1

| SUMMARY OF SIZE EXCLUSION HPLC DATA FOR EU103.2 ANTIBODY | | |
|---|---|---|
| | concentration | Total per 30 ml (x5) Expi293F transfection |
| EU103.2 | 1.2 mg/ml × 7 ml 0.37 mg/ml × 2 ml | 9.14 mg |

Humanization of Mouse Anti-VSIG4 Antibody-EU103.3 Antibody

Humanized anti-VSIG4 antibody hu6H8 (or EU103.3) was produced as described below.

mu6H8 VH Humanization

Framework for the humanized variant of VH was produced using mouse 6H8 antibody and Blast (https://blast.ncbi.nlm.nih.gov/Blast.cgi?PAGE=Proteins) (germline gene: VH2-5/D3-3/JH6c). Kabat numbering was used to classify the CDRs, and the humanized VH was designed with the framework and classified mu6H8 VH CDRs, back-mutations of VH2, VH27, VH30, VH93, and VH94. (hu6H8.3 VH)

mu6H8 VL Humanization

Framework for the humanized variant of VL was produced using mouse 6H8 antibody and Blast (https://blast.ncbi.nlm.nih.gov/Blast.cgi?PAGE=Proteins) (germline gene: A17/JK2). Kabat numbering was used to classify the CDRs, and the humanized VL was designed with the framework and classified mu6H8 VL CDRs, back-mutations of VH2, VH4, VH36, and VH46. (hu6H8.3 VL)

Cloning and Expressions of IgG Antibody-EU103.3 Antibody

The heavy chain variable region sequence was modified by FES (L234F, L235E, P331S) mutations to construct heavy chain pOptivec (Invitrogen) expression plasmid without Fc effector functions, as shown in FIG. 21A. The light chain variable region sequence was constructed using pcDNA3.3 (Invitrogen) and synthesized using IDT, as shown in FIG. 21B. The gene encoding the heavy chain (HC) was flanked with EcoR1, Nhe1 restriction enzyme to construct the pOptivec (FES) plasmid vector and the gene encoding the light chain (LC) was flanked with EcoR1, BsiW1 restriction enzyme to construct the pcDNA3.3 plasmid vector. Cloning was done with the mutation sites sub-cloned into the hu6H8.3 backbone. The resulting insert genes and linearized vectors were each cloned with In-Fusion® HD Cloning Kit(Clontech) and the sequencing primer was identified with CMV Forward, EMCV IRES reverse primer.

VSIG4 Knock Out Mice

VSIG K/O mice were generated by homologous recombination replacing exon 1 with the neomycin resistance gene. A targeting vector was generated for use in homologous recombination in ES cells. E1 and E1 and E2 indicate exon 1 and 2 of the CRIg gene (FIG. 41A). Homologous recombination of the CRIg allele in heterozygous female offspring from ES cell clone 1 and 2 (C1, C2) chimeric mice bred to WT mice was confirmed by Southern blot (FIG. 41B). Numbers of leukocytes in the peripheral blood of WT and K/O male and female mice were compared. Total blood cell counts were determined using a hematocytometer. Leukocytes were incubated with fluorochrome-conjugated antibodies specific to several cell surface markers and the numbers of different leukocyte subsets were determined by flow cytometry. Data represent mean+SD of 5-7 mice (FIG. 41C).

A1, A2, A1.3 and A2.3 Antibodies

A1 and A2 antibodies are generated by affinity maturation of EU103.3 antibody (see Table 2, below), where light chain variable regions at positions 76, 90, and/or 92 (kabat number) are mutated, as shown in Table 2 below.

A1.3 and A2.3 antibodies are generated from A1 and A2 antibodies, respectively, to further improve affinity to VSIG4.

Figure 40:
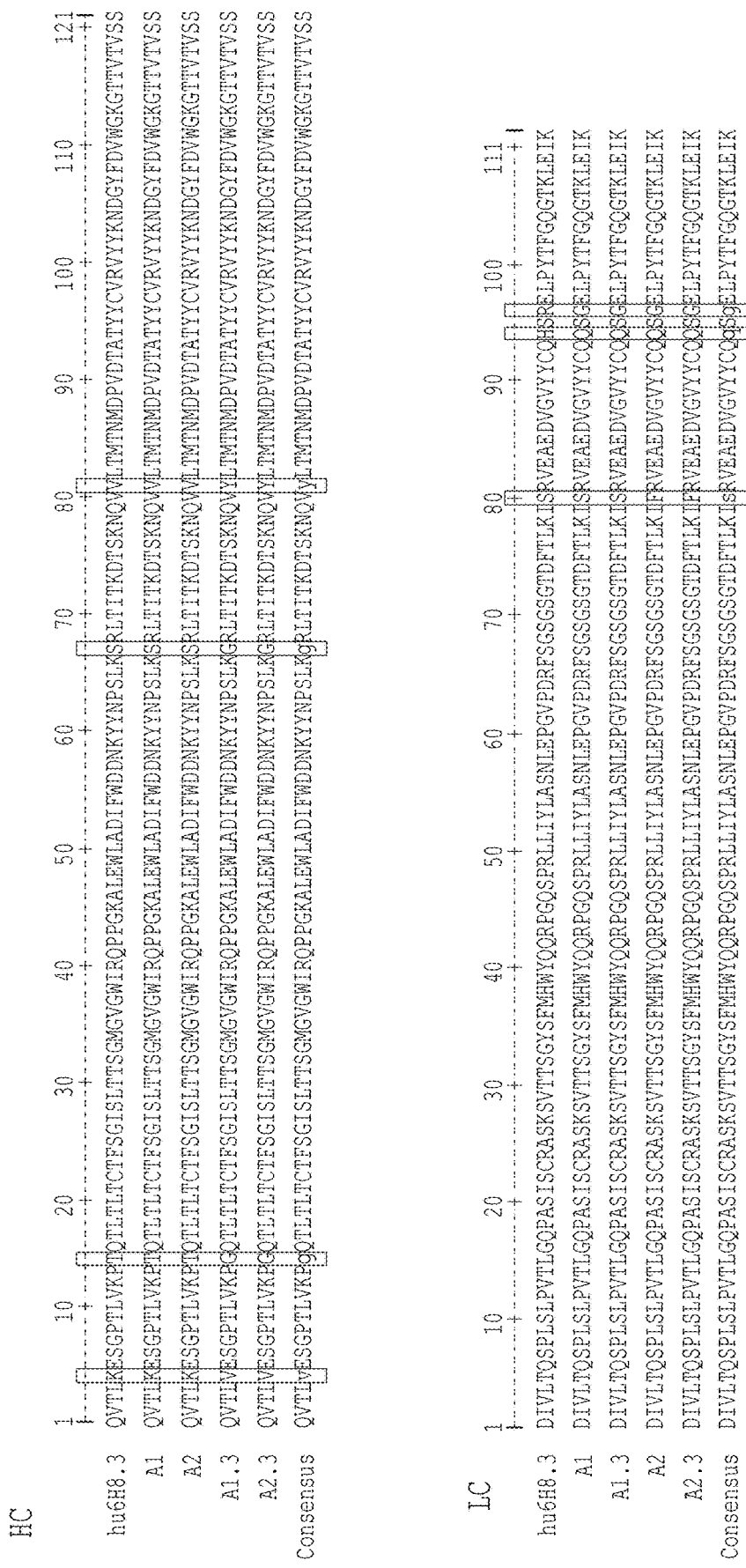
FIG. 40 shows sequence alignment of heavy chains and light chains of humanized EU103.3, A1, A2, A1.3, and A2.3 antibodies.

FIG. 40 provides amino acid sequences alignment for heavy chains and light chains of EU103.3, A1, A2, A1.3, and A2.3 are shown, along with consensus amino acid sequences for the heavy chain and light chain. Amino acid residues that differ between the different antibodies are shown in rectangular boxes.

TABLE 2

CLONES OF HUMANIZED ANTI-VSIG4 ANTIBODIES SCREENED IN AFFINITY MATURATION EXPERIMENTS

| Ab name | Library | HC | LC | Mutation sites (HC) (Kabat number) | Mutation sites (LC) (Kabat number) |
|---|---|---|---|---|---|
| T01.01 (A1) | L3A | WT | T01L1 | — | H90Q, R92G |
| T01.02 (A2) | L3A | WT | T01L2 | — | L76F, H90Q, R92G |
| T01.03 | L3B | WT | T01L3 | — | L76F, H90Q, R92F |
| T01.04 | L3B | WT | T01L4 | — | L76F, H90Q, R92L |
| T01.05 | H3B | T01H1 | WT | N99H | — |
| T01.06 | H3B | T01H2 | WT | Q1K, N99S | — |
| T01.07 | H3B | T01H3 | WT | K98E, N99K | — |
| T01.08 | L2 | WT | T01L5 | — | S52E, M106I |
| T01.09 | L2 | WT | T01L6 | — | L54R, M106I |
| T01.10 | L2 | WT | T01L7 | — | S52E, L54R, M106I |
| T01.11 | H1 | T01H4 | WT | S32Y | — |
| T01.12 | H1 | T01H5 | WT | S32F | — |
| T01.13 | H2A | T01H6 | WT | D50E, F52Y, W53S, D54G, D55E | — |
| T01.14 | H2A | T01H7 | WT | D50E, W53S | — |
| T01.15 | L1C | WT | T01L8 | — | L76F |
| T01.16 | L1C | WT | T01L9 | — | M33V, L76F |
| T01.17 | L1A | WT | T01L10 | — | K27E, L76F |
| T01.18 | L1B | WT | T01L11 | — | T27E, L76F |
| T01.19 | L1B | WT | T01L12 | — | T27K, L76F |
| T01.20 | H1 | T01H8 | WT | S32W | — |

Producing Antibodies with High Binding Affinity

The humanized antibody gene was inserted into a plasmid and expressed in IgG form using the Expi293 expression system (Invitrogen) then purified using AktaPure (GE healthcare), AktaPrime purifier (GE healthcare) and MabselectSURE column (GE healthcare, Cat #11-0034-95). The purified antibodies were run through a Desalting column (GE healthcare, Cat #17-1408-01) with PBS buffer change and the antibody concentration was measured with Multiskan GO (Thermo).

TABLE 3

PRODUCTION YIELDS OF ANTIBODIES WITH HIGH BINDING AFFINITY

| Ab name | Culture volume (mL) | Con. Of Ab (mg/mL) | Yield (mg) |
|---|---|---|---|
| T01.01 (A1) | 30 | 0.68 | 1.020 |
| T01.02 (A2) | 30 | 0.22 | 0.330 |
| T01.03 | 30 | 0.87 | 0.104 |

TABLE 3-continued

PRODUCTION YIELDS OF ANTIBODIES
WITH HIGH BINDING AFFINITY

| Ab name | Culture volume (mL) | Con. Of Ab (mg/mL) | Yield (mg) |
|---|---|---|---|
| T01.04 | 30 | 0.99 | 0.119 |
| T01.05 | 30 | 0.26 | 0.390 |
| T01.06 | 30 | 1.2 | 0.144 |
| T01.07 | 30 | 0.33 | 0.495 |
| T01.08 | 30 | 1.46 | 0.292 |
| T01.09 | 30 | 1.73 | 0.346 |
| T01.10 | 30 | 2.07 | 0.414 |
| T01.11 | 30 | 0.27 | 0.054 |
| T01.12 | 30 | 1.26 | 0.252 |
| T01.13 | 30 | 0.72 | 0.144 |
| T01.14 | 30 | 0.89 | 0.178 |
| T01.15 | 30 | 0.21 | 0.042 |
| T01.16 | 30 | 1.05 | 0.21 |
| T01.17 | 30 | 0.76 | 0.15 |
| T01.18 | 30 | 0.33 | 0.07 |
| T01.19 | 30 | 0.44 | 0.09 |
| T01.20 | 30 | 0.99 | 0.198 |

PBMC-Derived Macrophages Differentiation

M1 and M2 macrophages were obtained from PBMC using the protocol below.
1. Blood mixture with PBS(1:1) 20 ml overlay on to 10 ml of Ficoll-Paque™ Plus (GE Healthcare, Cat #17-1440-02)
2. Centrifugate at 400×g for 35 min (2 accel, 0 brake)
3. PBMC isolation and washing by RPMI-1640 medium (WelGene, Cat #LB011-01) at 2000 rpm for 5 min×2 times
4. Counting
5. MACs buffer (2% FBS(Millipore, Cat #TMS-013-BKR) in PBS(WelGene, Cat #LB004-02) 1~2 ml suspension
6. Add CD14-microbead (20 ul/$10^7$ cells) (Miltenyi Biotec, Cat #130-050-201)
7. Incubation for 30 min on ice
8. Washing by MACs buffer at 2000 rpm for 5 min×2 times
9. Counting
10. Load the cells into MACs column (Miltenyi Biotec, Cat #130-042-401)
11. Positive selection and counting
12. Suspension by culture medium (RPMI-1640+10% FBS+Penicillin/Streptomycin (Gibco, Cat #15140-122)+Glutamax (Gibco, Cat #35050-061)+20~40 ng/ml of rhM-CSF (Biolegend, Cat #574806)
13. Seed the CD14$^+$ cells in 100 mm culture dish (1×$10^6$ cells/10 ml/dish) (Thermo Scientific, Cat #150466)
14. Every 3 days later, fresh culture medium change
15. After 7~10 days, M0 macrophages differentiation check by FACs
16. Differentiation of M0 to M1 or M2 macrophages by LPS 20 ng/ml (Sigma-Aldrich, Cat #L4391)+rhIFNγ 20 ng/ml (Biolegend, Cat #570204) (M1) and rhIL4 20 ng/ml (Biolegend, Cat #574002)+rhIL13 20 ng/ml (Biolegend, Cat #571102) (M2) culture medium (RPMI-1640+10% FBS+Penicillin/Streptomycin+Glutamax) for 2 days
17. After M1 or M2 differentiation, cell phenotype check by FACs
18. For M2 to M1 macrophages conversion, add the antibodies 20 ug/ml or LPS 20 ng/ml+rhIFNγ 20 ng/ml (positive control) in fresh culture medium (RPMI-1640+10% FBS+Penicillin/Streptomycin+Glutamax) for 2 days
19. After M2 to M1 conversion, cell phenotype check by FACs and cytokines/chemokines check in cultured sup by LEGENDplex™ (Biolegend, Cat #740502)

FACs Analysis

The following antibodies were used for FACs analysis:
hCD14-BV650 (BD Bioscience, Cat #563419)
hCD14-BV421 (BD Bioscience, Cat #565283)
hIFNγ-PE/Cy7 (BD Bioscience, Cat #557844)
hCD3-BV510 (BD Bioscience, Cat #563109)
hCD8-V450 (BD Bioscience, Cat #560347)
hCD68-PE (Biolegend, Cat #333808)
hCD93-PE (Biolegend, Cat #336108)
HLA-DR-BV421 (Biolegend, Cat #307636)
hCD45-PE (Biolegend, Cat #304008)
hCD64-APC (Biolegend, Cat #305014)
hCD163-APC/Cy7 (Biolegend, Cat #333622)
hCD86-PerCP/Cy5.5 (Biolegend, Cat #305420)
hCD86-BV421 (BD Bioscience, Cat #562432)

Example 1: VSIG4 Expression in Macrophages

Figure 3A:
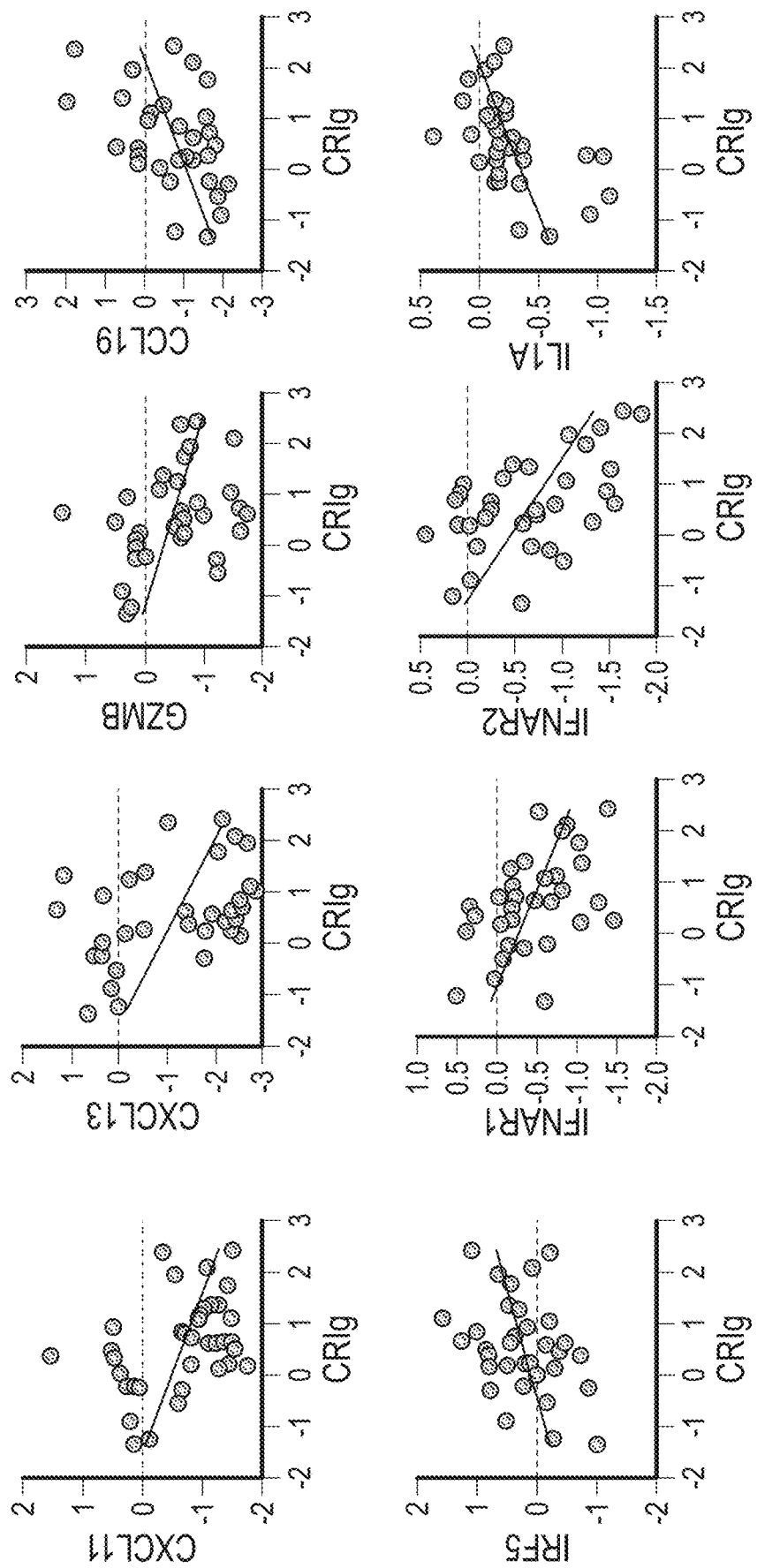
FIGS. 3A and 3B show correlation of VSIG4 mRNA expression with various genes in tumor tissue.
Figure 3B:
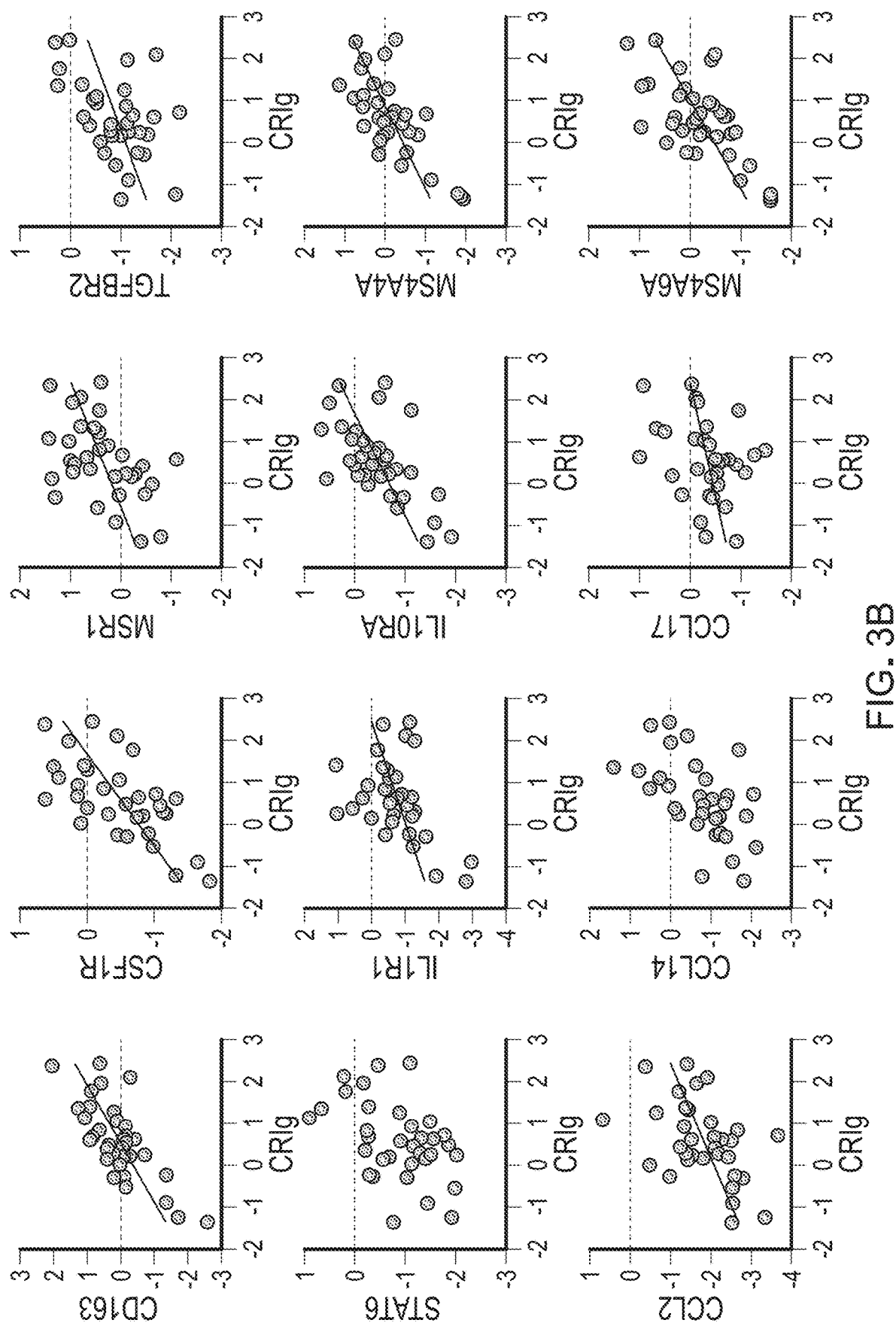

VSIG4 is expressed in M2 macrophages. FIGS. 3A and 3B show correlative data for VSIG4 expression (as measured by mRNA) to that of various genes associated with type 2 macrophages (M2) and tumor-associated macrophages. As shown in FIG. 3A, VSIG4 expression correlates negatively with [CXCL11, CXCL13, ZNMB, IFNAR1, IFNAR2] expression, but while it correlates positively with CCL19, IRF5, and ILIA expression. FIG. 3B shows VSIG 4 expression correlates positively with CD163, CSF1R, MSR1, TGFBR2, STAT6, IL1R1, IL10RA, MS4A4A, CCL2, CCL14, CCL17, and MS4A6A expression.

FIG. 5 shows expression of VSIG4 in M2 macrophages. The two panels in the top row of FIG. 5 shows light microscope images showing M1 and M2 macrophages' morphology. The second and third rows show flow cytometry data for lymphocytes stained for CD14 and VSIG4, demonstrating that M2 cells (stained positive for CD14) also expressing VSIG4.

Example 2: Human Anti-VSIG4 Antibody Induces Cytokine and Chemokine Secretion in M2 Macrophages M1 and M2 macrophages were treated with EU103.2 antibody and secretion of proinflammatory cytokines and chemokines were measured. As shown in FIG. 6, treatment of M2 macrophages with EU103.2 resulted in induction of the cytokines and chemokines IL12, IFNγ, IL10, and IL23.

Example 3: Humanized Anti-VSIG4 Antibody Converts M2 Macrophages into M1 Macrophages To further test the effects of EU103.2 on macrophages, M2 macrophages were treated with EU103.2 antibody and stained for the M2 macrophage marker CD163. As shown in FIG. 7, EU103.2 treatment decreased the expression of M2 macrophage marker CD163 in M2 macrophages, which suggested blocking of VSIG4 using EU103.2 resulted in conversion of M2 macrophages into a different cell type.

Figure 8:
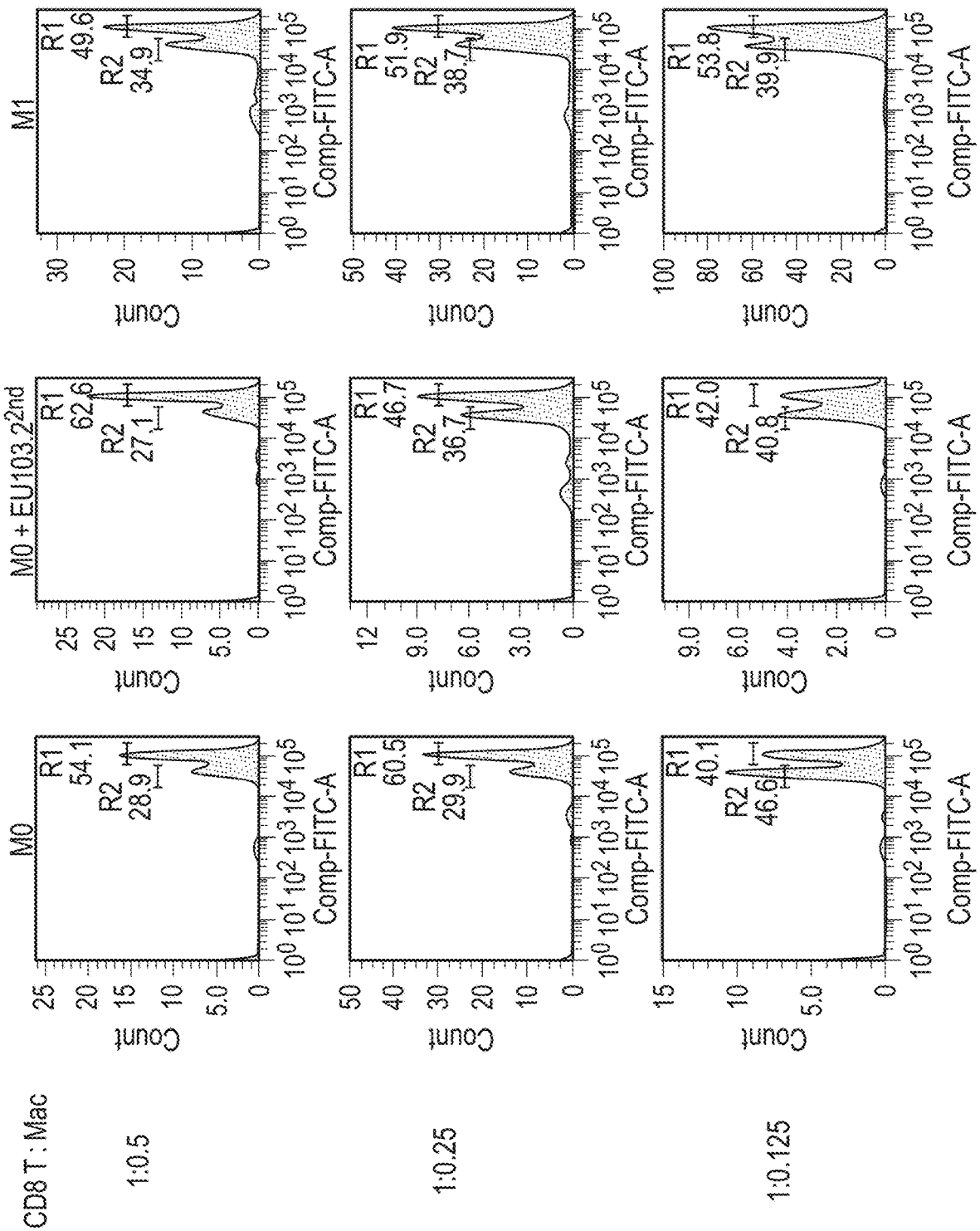
FIG. 8 is a set of FACS data (first six columns) and quantification of these data (last column) showing induction of CD8+ T cell proliferation when CD8+ T cells were co-cultured with M2 macrophages treated with EU103.2.
Figure 8:
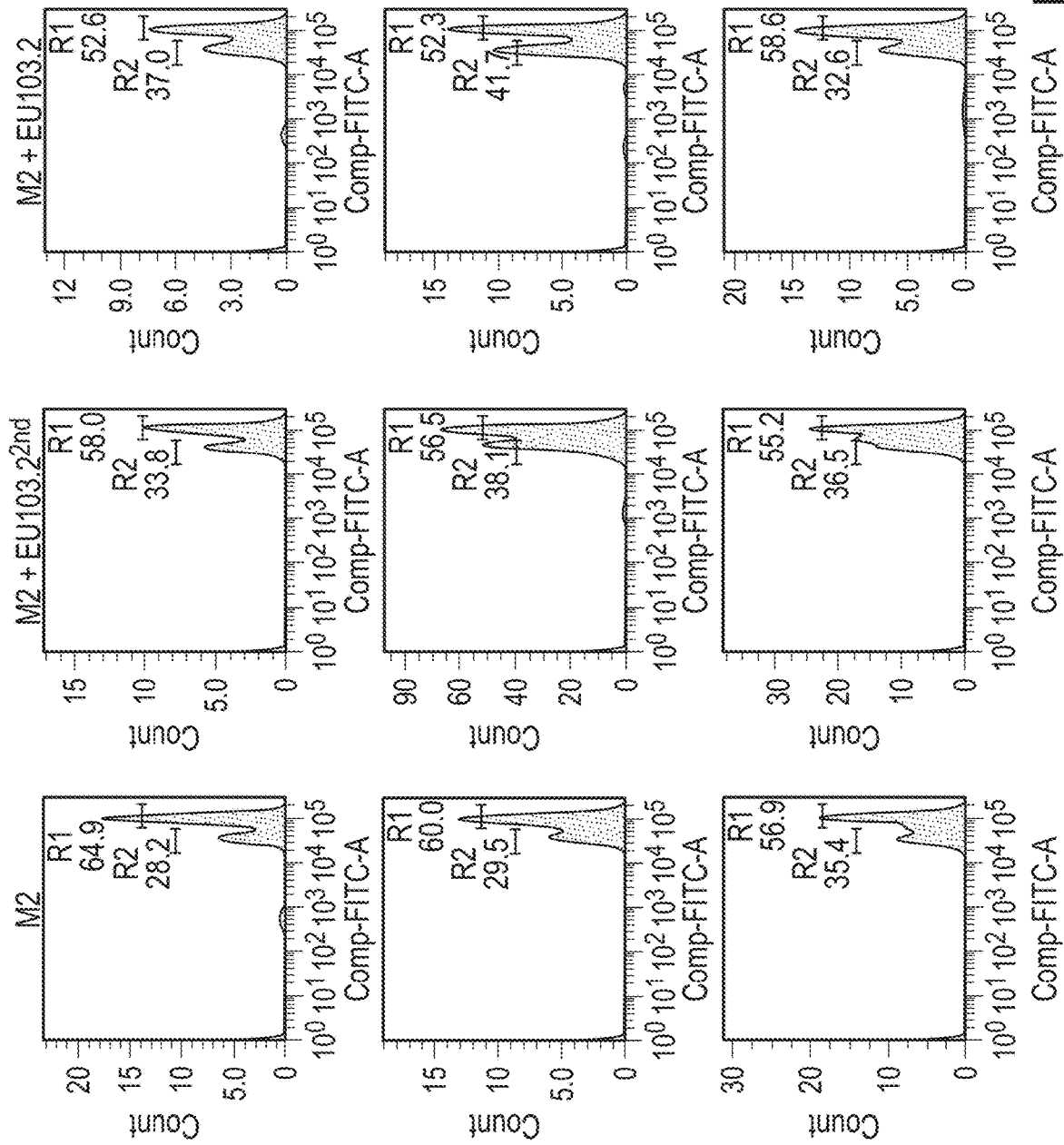
Figure 8:
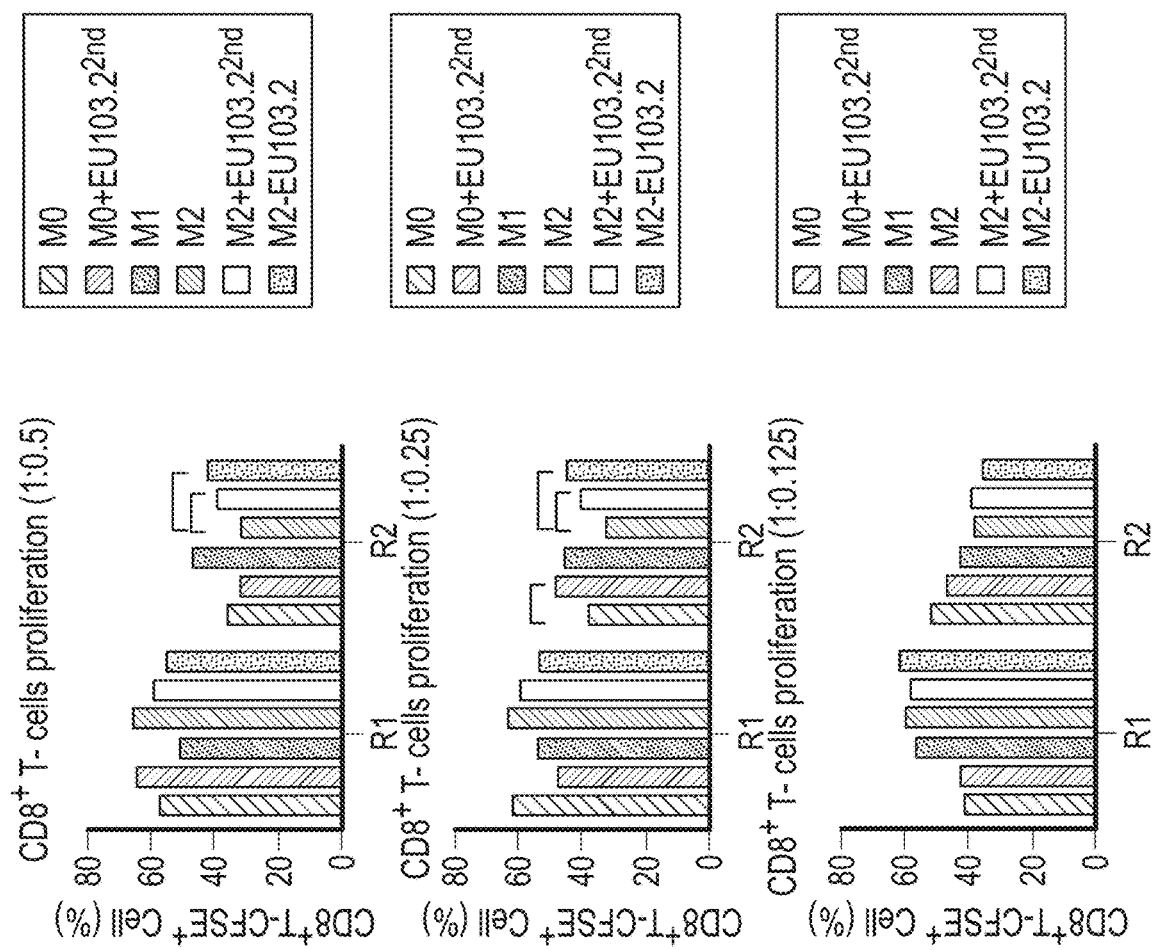

Next, the effects of EU103.2 antibody on macrophage-T cell interaction was tested by co-incubating M2 macrophages with CD8$^+$ T cells with or without EU103.2 antibody treatment. As shown in FIG. 8, EU103.2 treated M2 macrophages, when co-incubated with CD8+ T cells, resulted in proliferation of the CD8+ T cells, indicating that M2 macrophages are convert into M1 macrophages when treated with EU103.2 antibody, since M1 macrophages induce CD8+ T cell proliferation while M2 macrophages suppress CD8+ T cell proliferation.

Figure 9:
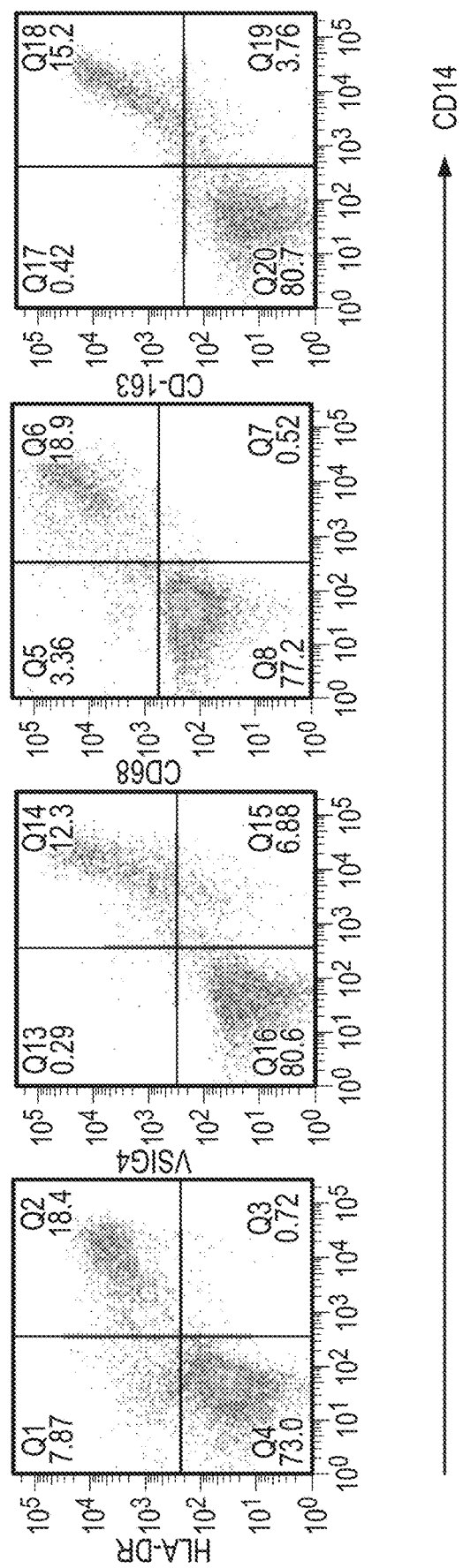
FIG. 9 is a set of FACS data showing VSIG4 expression in macrophages isolated from abdominal fluid from ovarian cancer patients.
Figure 10:
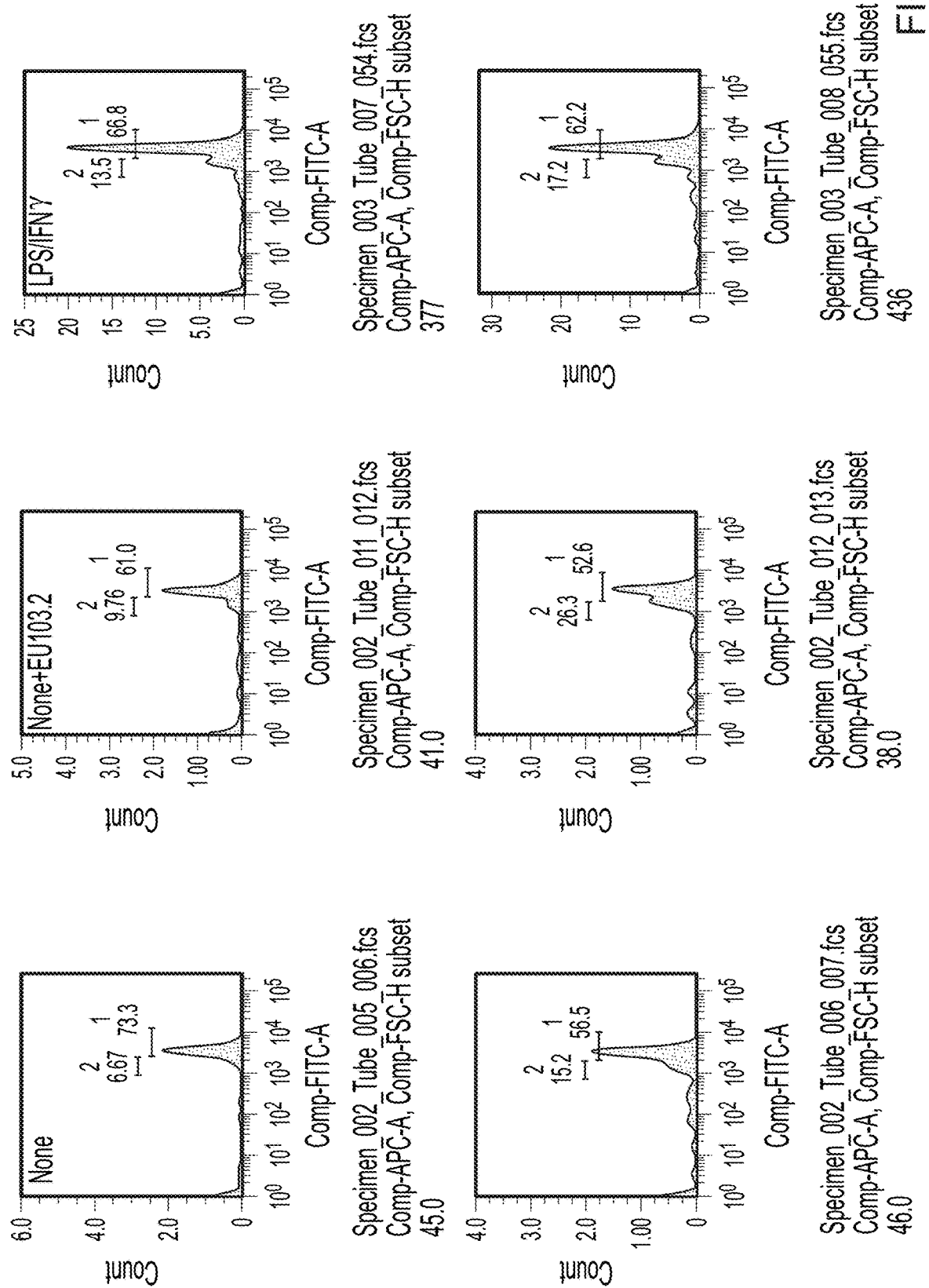
FIG. 10 is a set of FACS data showing induction of CD8+ T cell proliferation when co-cultured with EU103.2-treated macrophages isolated from ovarian cancer patients.
Figure 10:
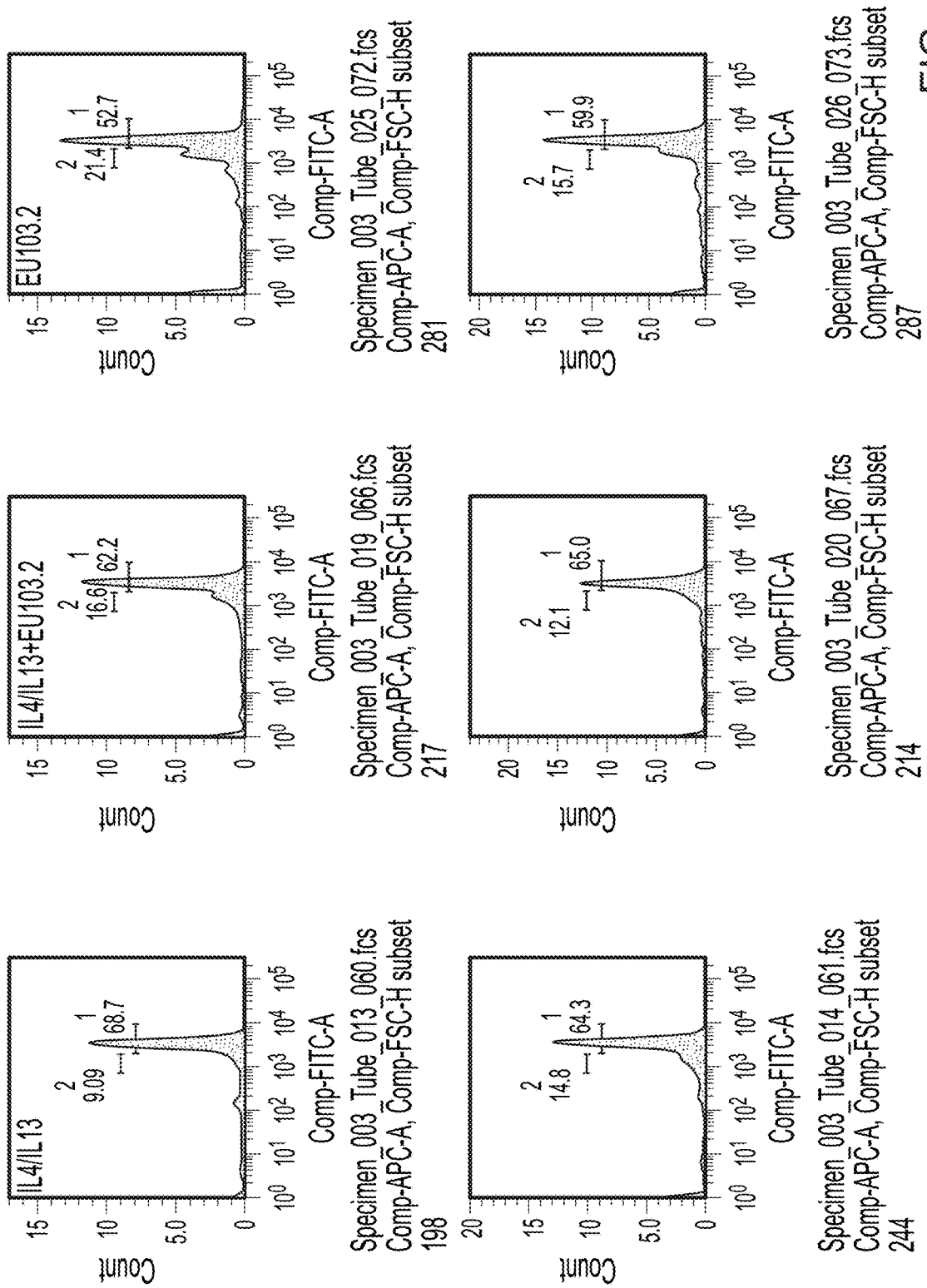
Figure 11:
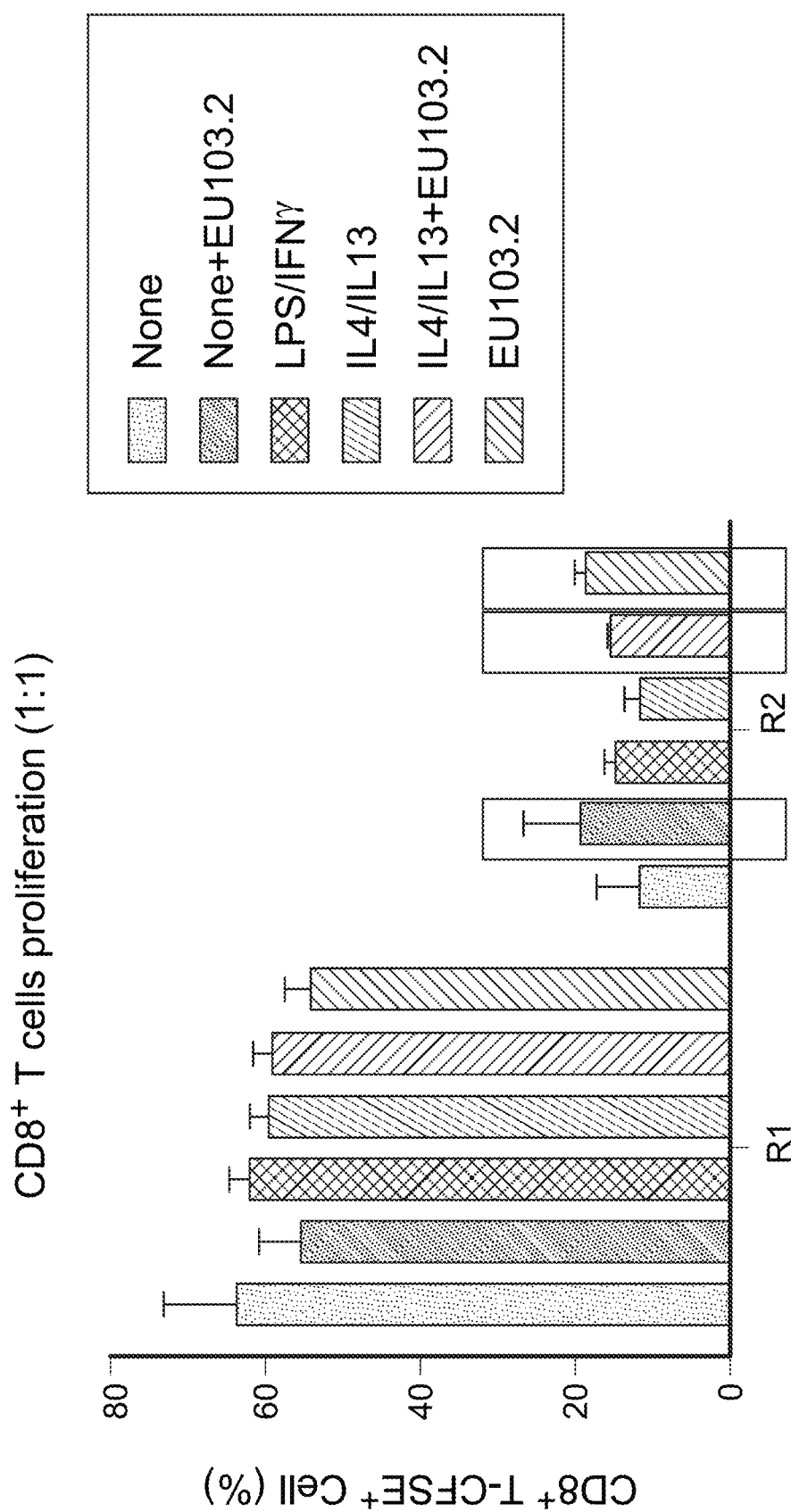
FIG. 11 is a graph showing induction of CD8+ T cell proliferation when co-cultured with anti-EU103.2-treated macrophages isolated from ovarian cancer patients.

Next, to further investigate the effects of EU103.2 antibody on human macrophages in the context of cancer biology, abdominal fluid samples from ovarian cancer patients were collected and first analyzed for VSIG4 expression. As shown in FIG. 9, macrophages obtained from abdominal fluid of ovarian cancer patients included M2 macrophages that co-expressed VSIG4 and CD14, and as shown in FIGS. 10 and 11, induced CD8+ T cell proliferation.

Further, microscope images confirm that EU103.2 antibody treatment converted M2 macrophages into M1 macrophages, as shown in FIG. 12.

Figure 13:
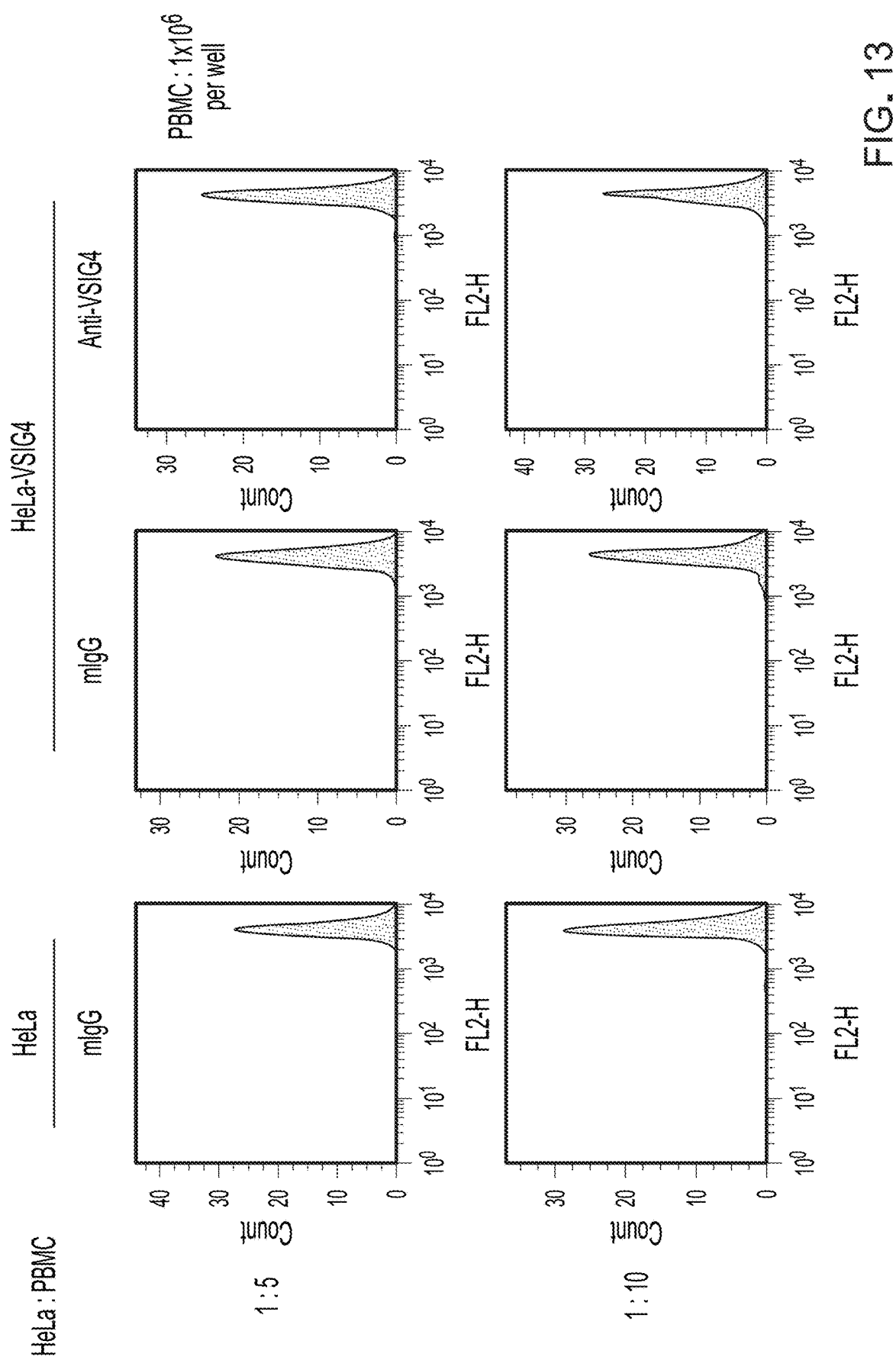
FIG. 13 is a set of FACS data showing blocking interaction between CD8+ cells and VSIG4 enhances proliferation of CD8+ T cells.
Figure 13:
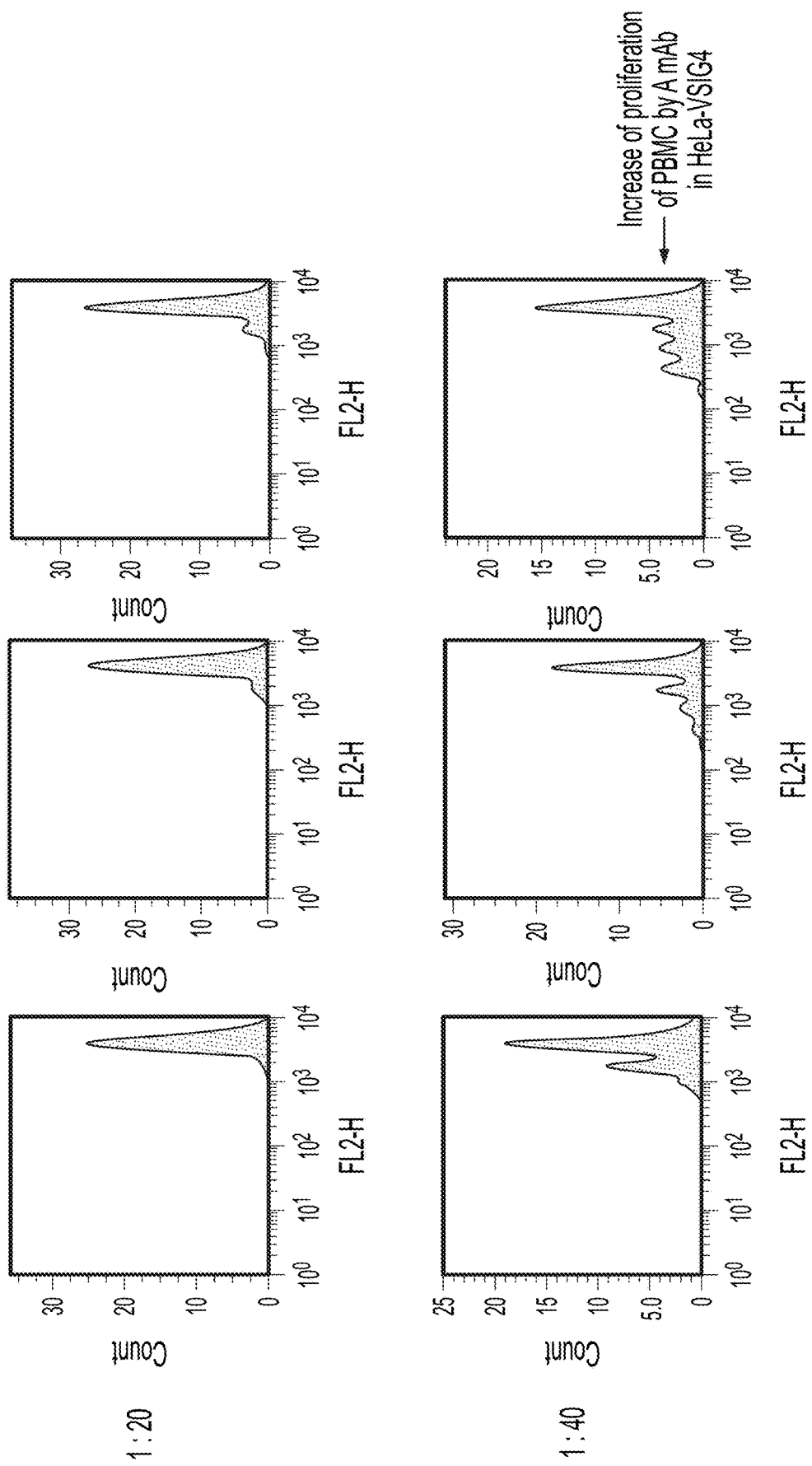
Figure 14A:
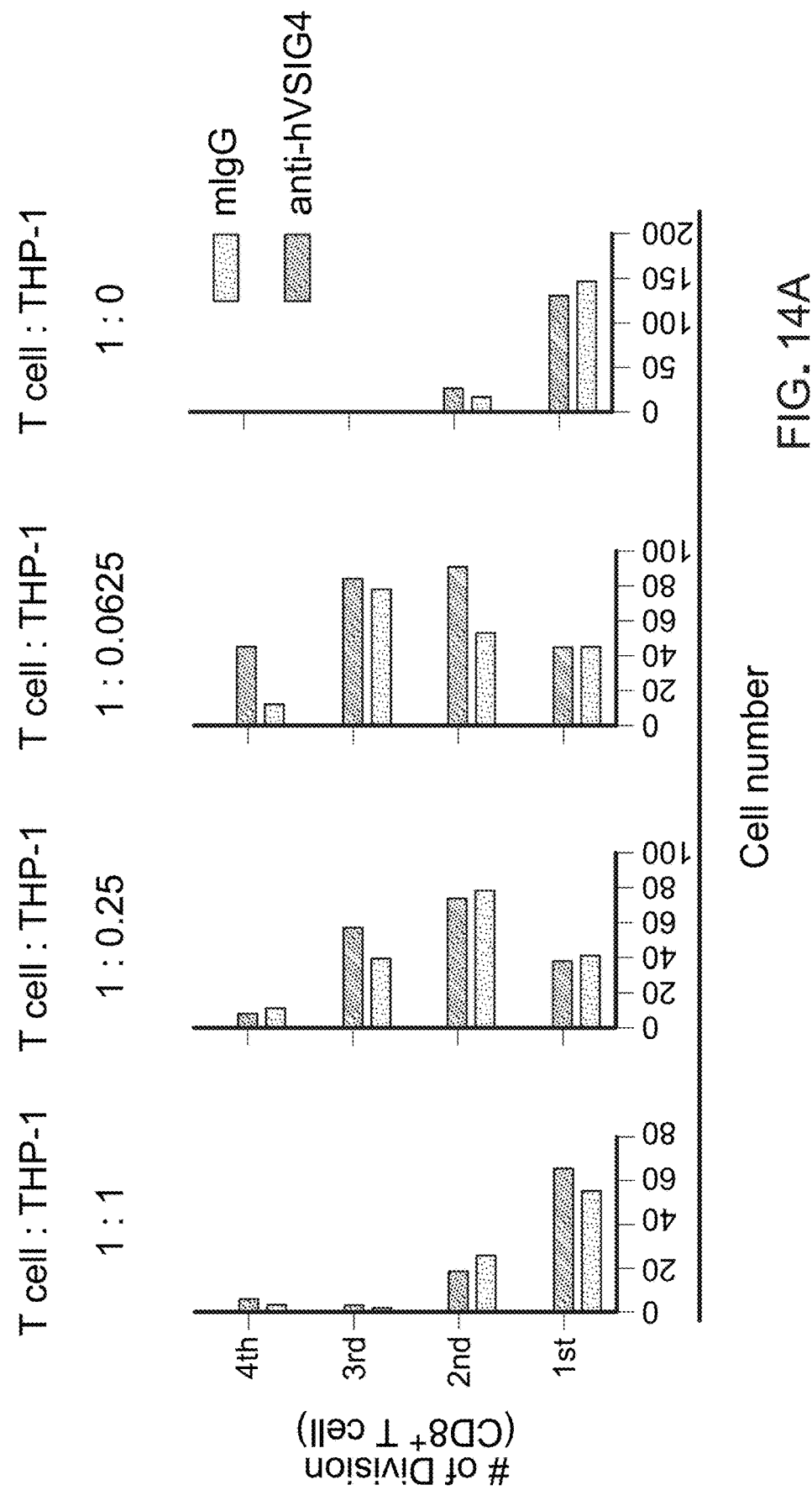
FIGS. 14A and 14B are set of graphs showing enhanced CD8+ cell proliferation by blocking the suppression by THP-1 cells.
Figure 14B:
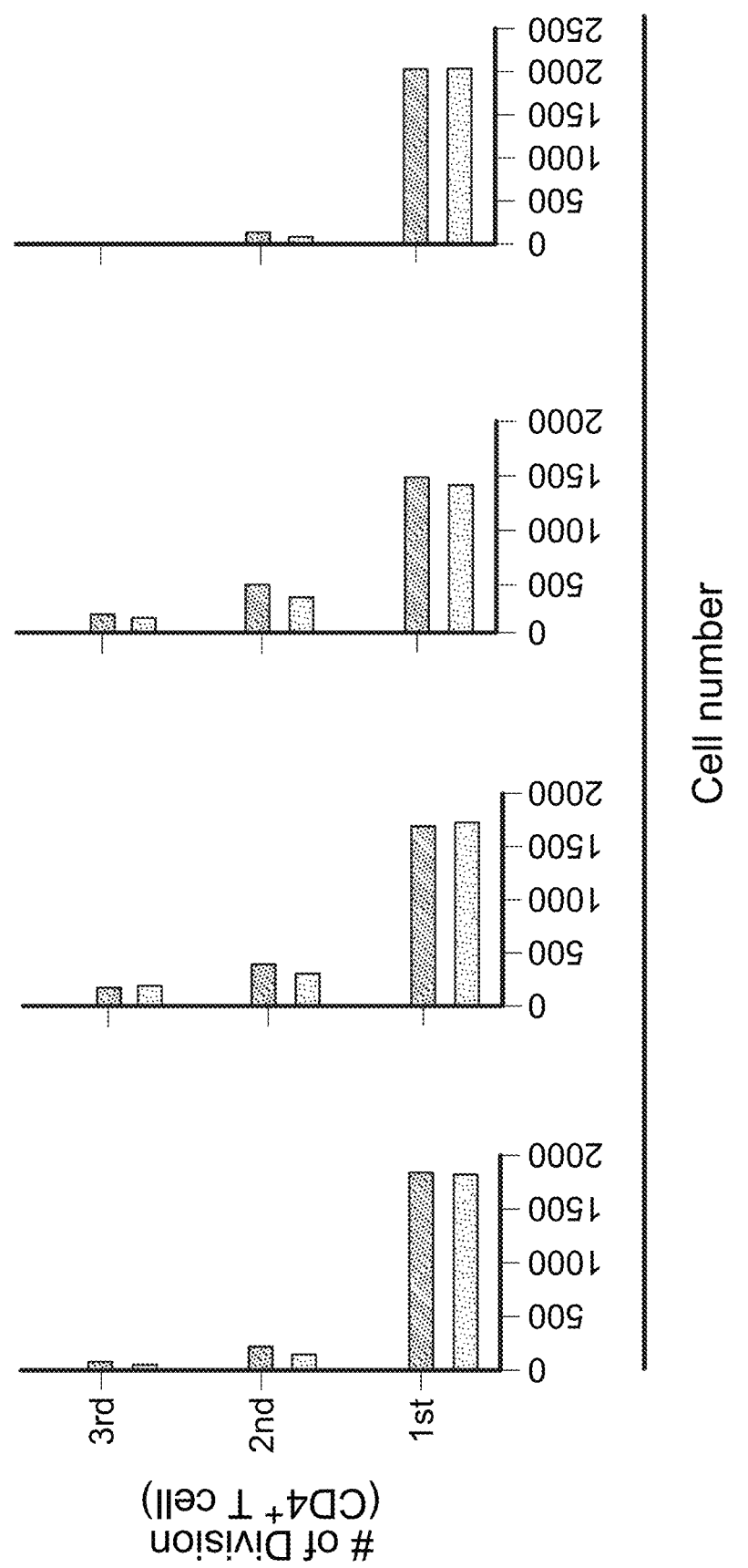

The role of VSIG4 signaling in CD8+ T cell proliferation by macrophages was further confirmed by co-culturing of HeLa cells expressing VSIG4 with PBMC, with or without anti-VSIG4 antibody to block VSIG4, as shown in FIG. 13. This experiment showed blocking the interaction between VSIG4 and CD8+ T cells leads to enhanced proliferation of CD8+ T cells. To further examine the role of VSIG4 in CD8+ T cells, the monocytic THP-1 cells were co-incubated at various ratios with T cells, either in the presence of anti-VSIG4 antibody or a control IgG antibody, to show that anti-VSIG4 antibody was able to increase CD8+ T cells at 4 divisions, as compared to the control IgG.

Example 4: Antitumor Effects Blocking VSIG4 Signaling Using Anti-VSIG4 Antibody or VSIG4 Knock Out Mouse Model To determine the antitumor effects of anti-VSIG4 antibody, three mouse tumor models were used: MC38 colon adenocarcinoma mouse tumor model, B16F10 melanoma mouse tumor model, and 3LL lung carcinoma mouse tumor model using VSIG4 knock out mice, and compared to wild-type mice, as shown in FIGS. 15A, 15B, and 15C, respectively. Tumor growth was suppressed, especially for MC38 and 3LL mouse tumor models in VSIG4 knock out mice, as compared to wild type mice (see FIGS. 15A and 15C, respectively), confirming that tumor growth is suppressed in the absence of VSIG4 signaling.

Figure 16:
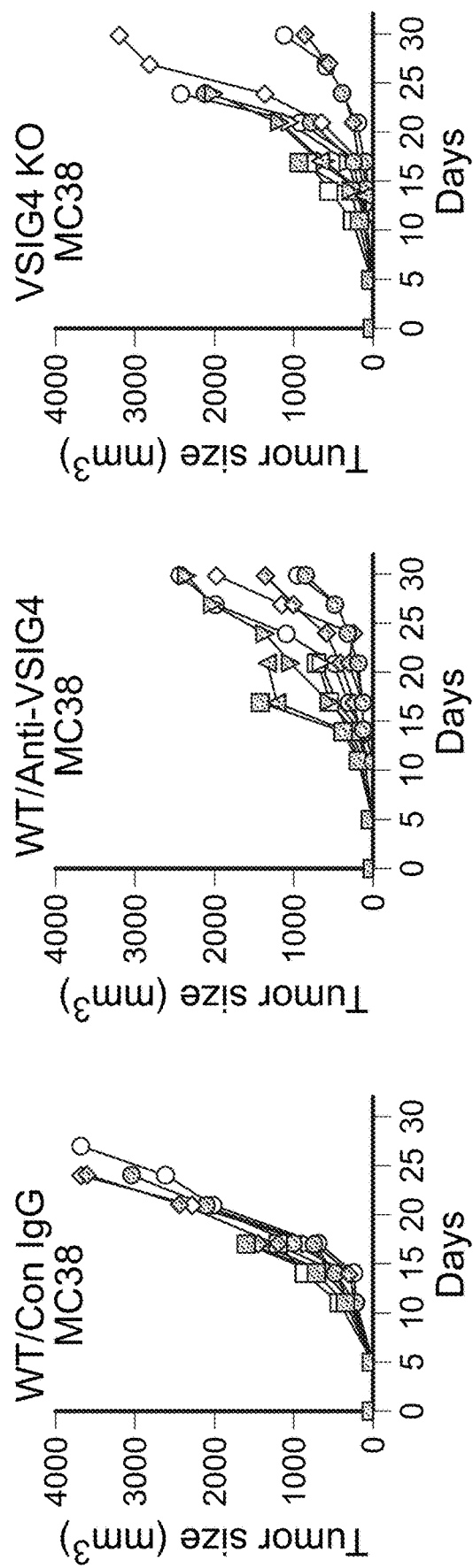
FIG. 16 is a set of graphs showing the anti-tumor activities of anti-VSIG4 antibody in a VSIG4 knockout mouse model.

Similar suppression of tumor growth was observed in MC38 mouse tumor model in wild type mice that were injected with anti-VSIG4 antibody, as compared to mice injected with control IgG, as shown in FIG. 16. The extent of tumor growth suppression by anti-VSIG4 antibody was at least as pronounced, if not greater, than those in VSIG4 knock out mice.

Figure 17A:
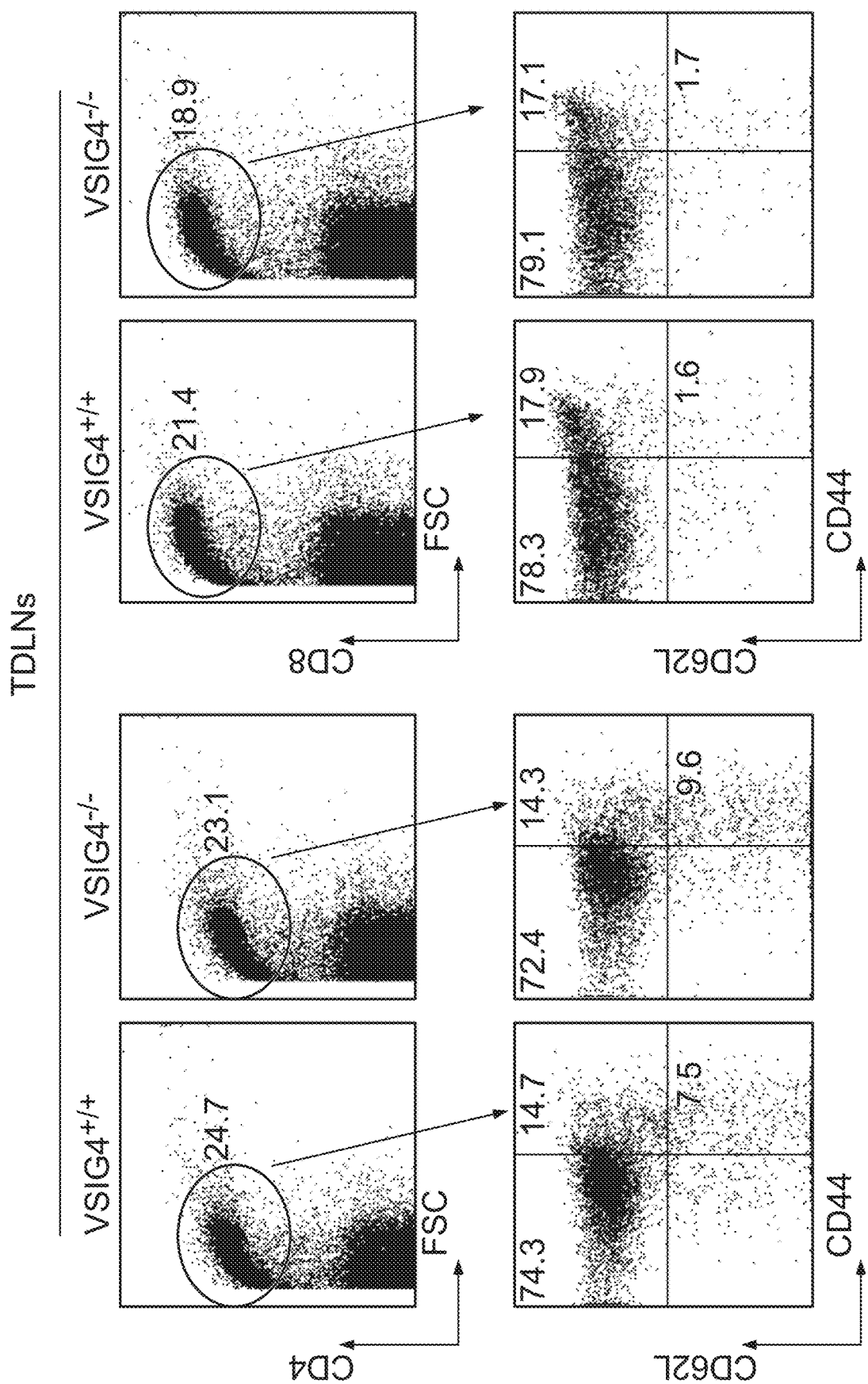
FIG. 17A is a set of FACS data showing activation status of T cells and MDSCs in TDLNs in the absence of VSIG4 signaling.
Figure 17B:
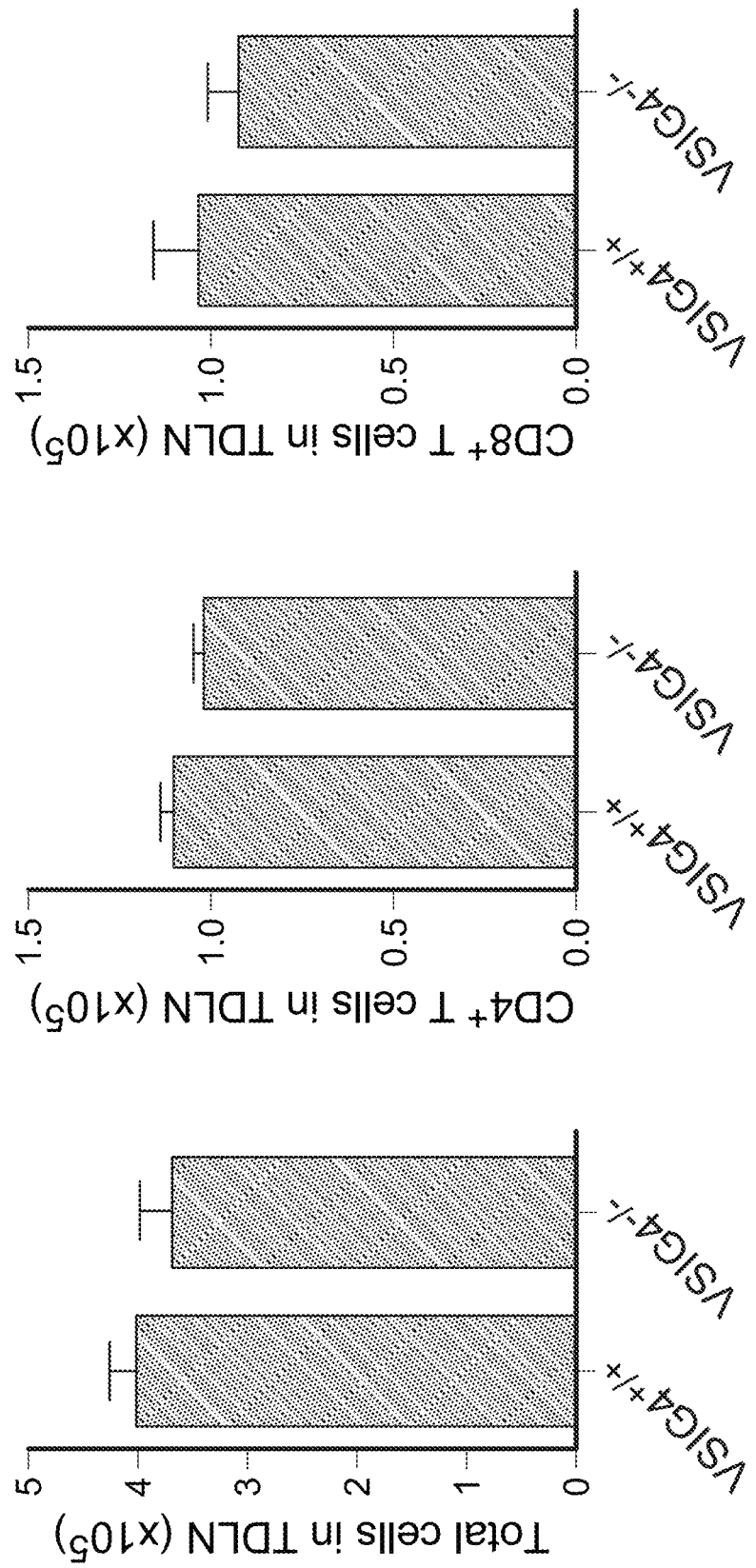
FIG. 17B is a set of graphs showing activation status of T cells and MDSCs in TDLNs in the absence of VSIG4 signaling.

Next, activation status of lymphocytes from tumor-draining lymph nodes were examined in VSIG4 knock out mice and compared to wild-type mice. As shown in FIGS. 17A and 17B, comparable levels of CD4+ and CD8+ lymphocytes were observed in the VSIG4 knock out mice as compared to their wild-type counterparts, and comparable CD62L expression was observed in those lymphocytes expressing CD4 and CD8 between the VSIG4 knock out mice and wild-type mice. Further, VSIG4 knock out mice had increased CD8β+ T cells, as compared to wild-type mice, as shown in FIG. 17C, but comparable levels of CD11β+/Gr-1-lymphocytes, as shown in FIG. 17D.

Figures 18A, 18B:
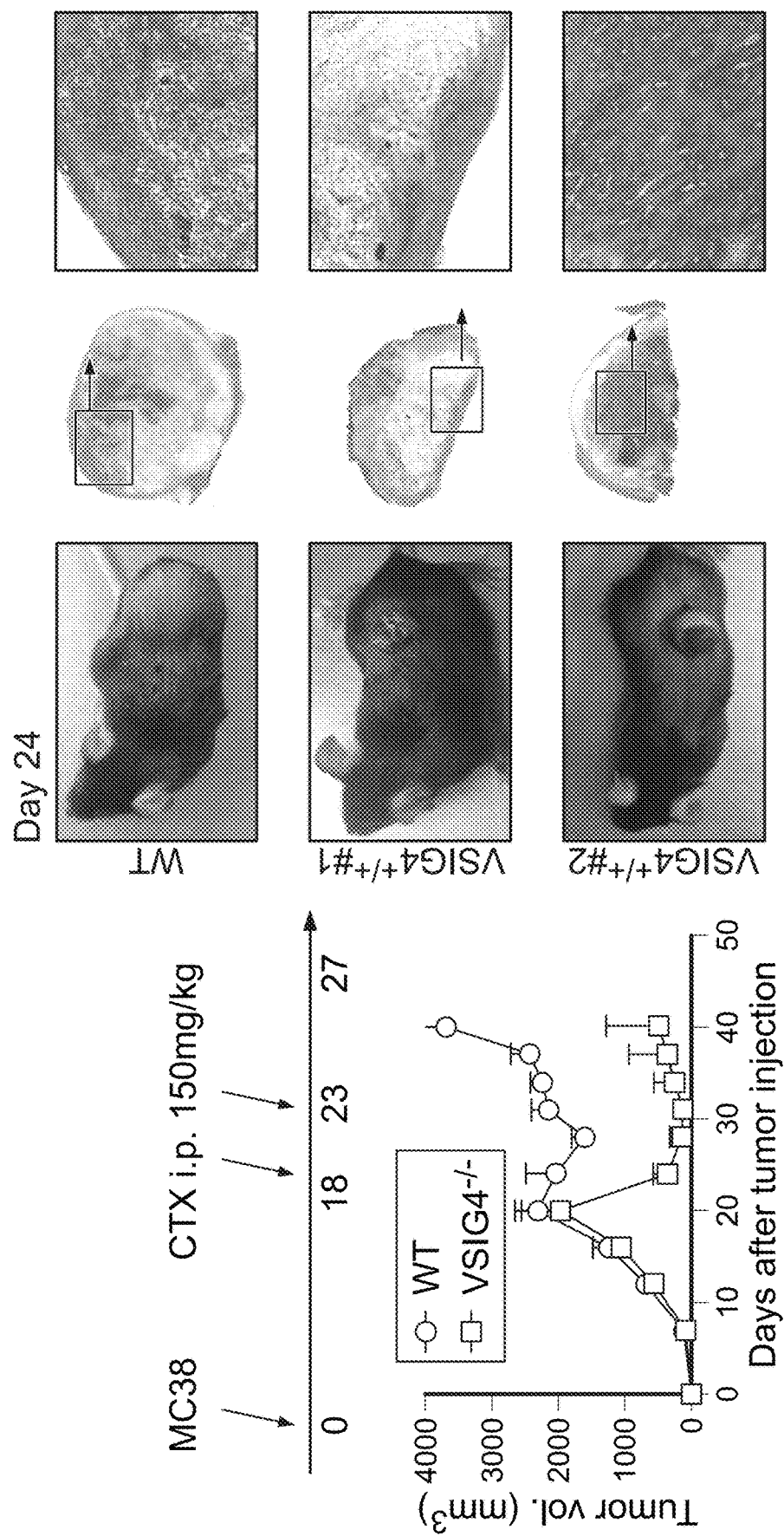
FIG. 18A is a graph showing suppression of tumor growth in the absence of VSIG4 signaling.
FIG. 18B is a set of histological slides showing suppression of tumor growth in the absence of VSIG4 signaling.

To further evaluate the role of VSIG4 signaling in tumor growth, CD38 colon adenocarcinoma mouse tumor model was used in both VSIG4 knock out mice and wild-type mice, where the chemotherapy agent Claforan (CTX) was injected interperitoneally at days 18 and 23 after tumor injection in the subject mice, as shown in the schematic diagram at the top of FIG. 18A. Claforan injection resulted in a greater reduction of tumor volume in VSIG4 knock out mice as compared to wild type mice, and this reduction in tumor size was maintained 40 days after tumor injection. In contrast, in wild-type mice, CTX injection resulted in a slight reduction in tumor size, followed by continued growth of tumor size, as shown in FIG. 18A. Images of mice and micrographs of tumor sections for both VSIG4 knock out mice and a wild-type mouse at day 24 after tumor injection are shown in FIG. 18B. Tumor sections were collected from VSIG4+/+ and VSIG4-/- C57BL/6 mice at day 24 and paraffin sections of tumor tissues were stained with H&E.

Figure 19:
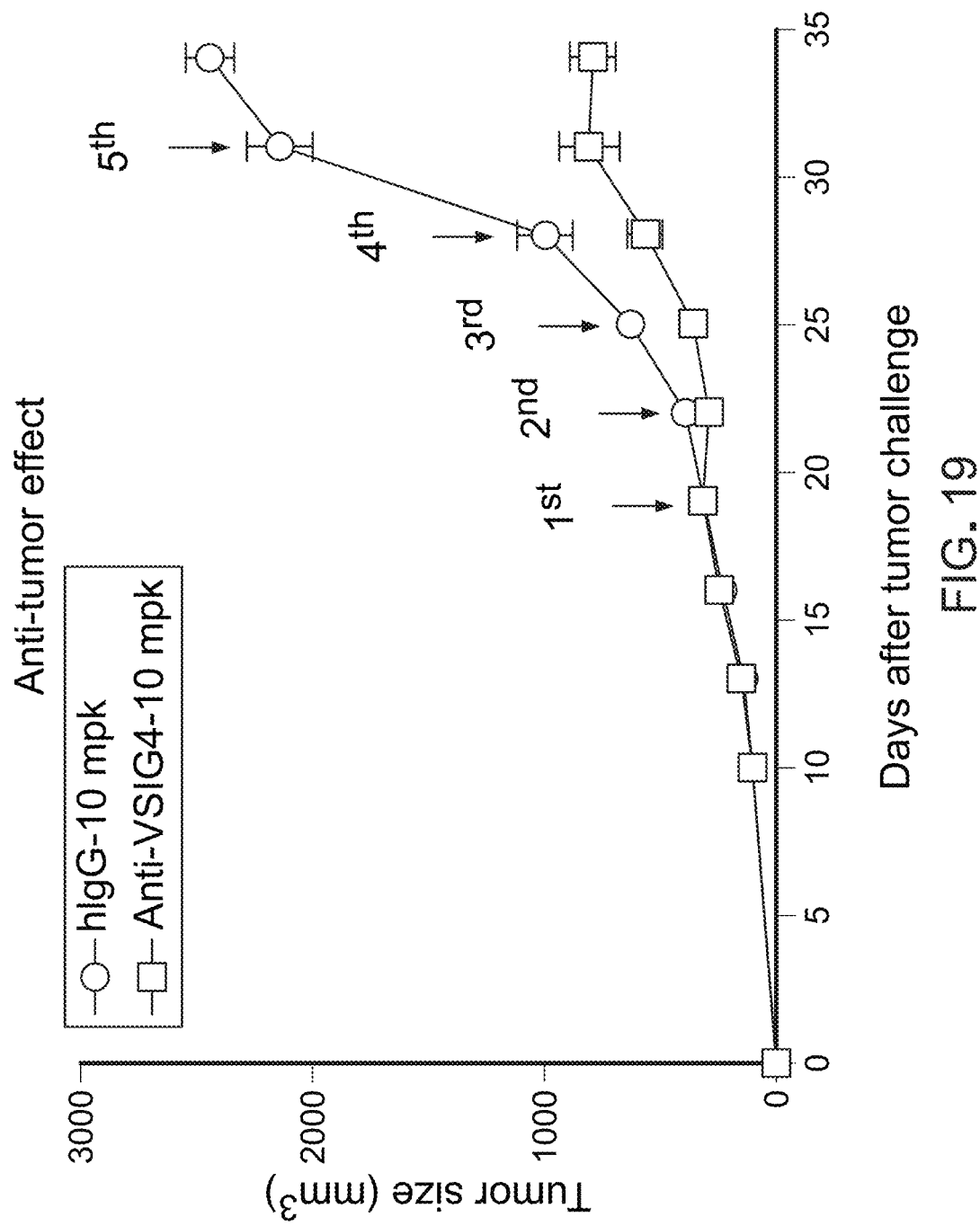
FIG. 19 is a graph showing anti-tumor activities of anti-VSIG4 antibody in humanized mouse model.

The effects of anti-VSIG4 on tumor suppression in humanized mouse model was evaluated by injecting 10 mg/kg of anti-VSIG4 antibody at days 19, 22, 25, 28, and 31 after HT29 cancer cell injection in humanized mice, as shown in FIG. 19. Significant suppression of tumor growth was observed in mice that received anti-VSIG4 antibody as compared to those that received IgG control injection.

Figure 20:
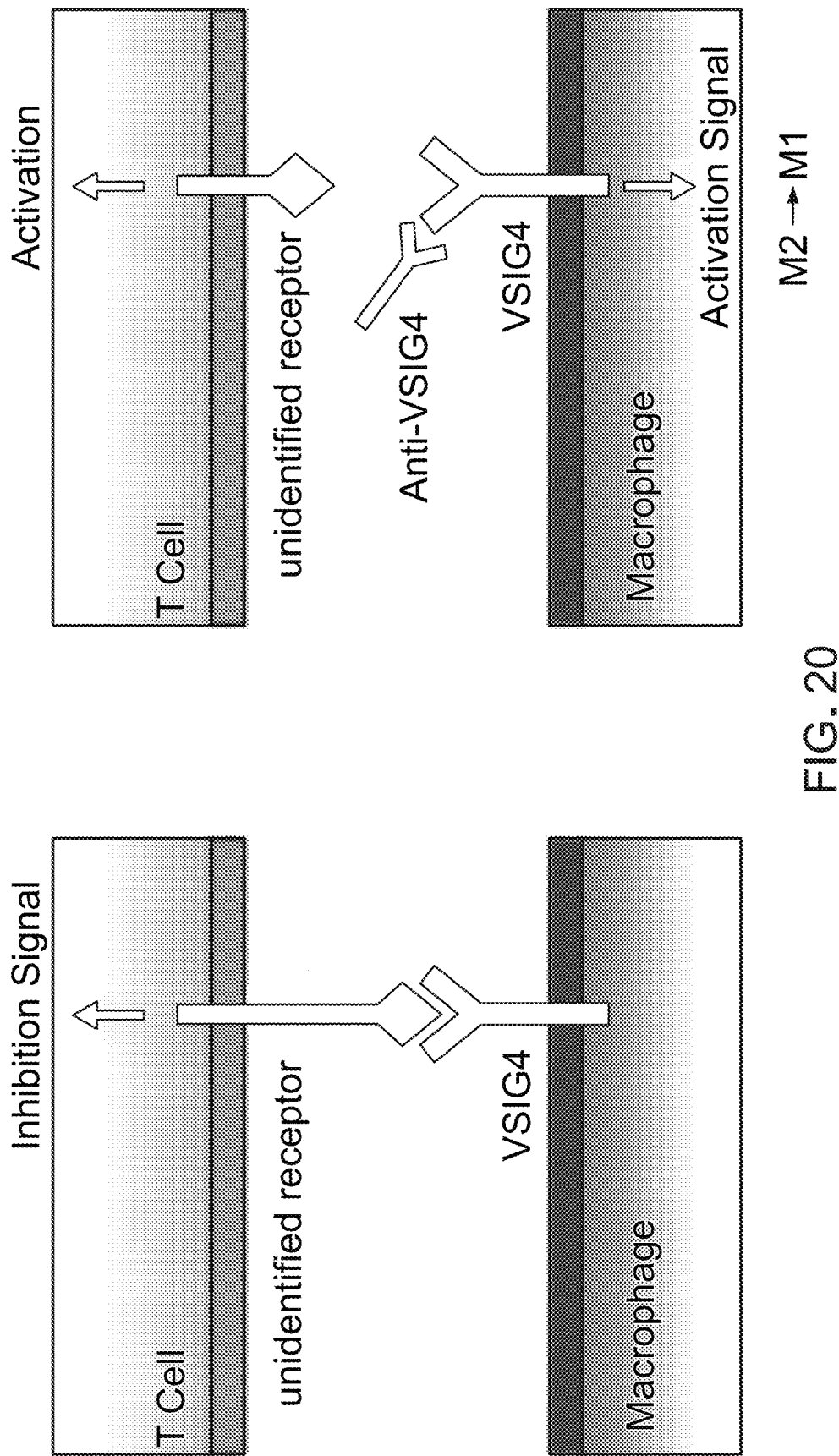
FIG. 20 is a schematic diagram illustrating mechanism of how administration of EU103.2 antibody to macrophages results in conversion of M2 macrophages to M1 macrophages, which results in proliferation of CD8+ T cells.
Figure 24:
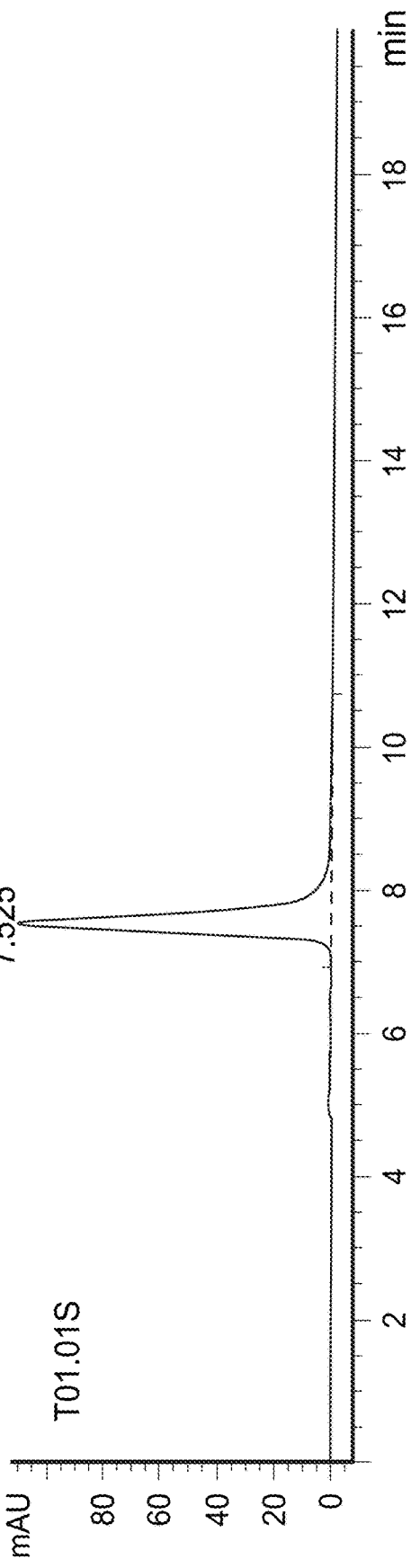
FIG. 24 is a HPLC plot showing protein profile of A1.3 antibody (EU103_T01.01S).
Figure 25:
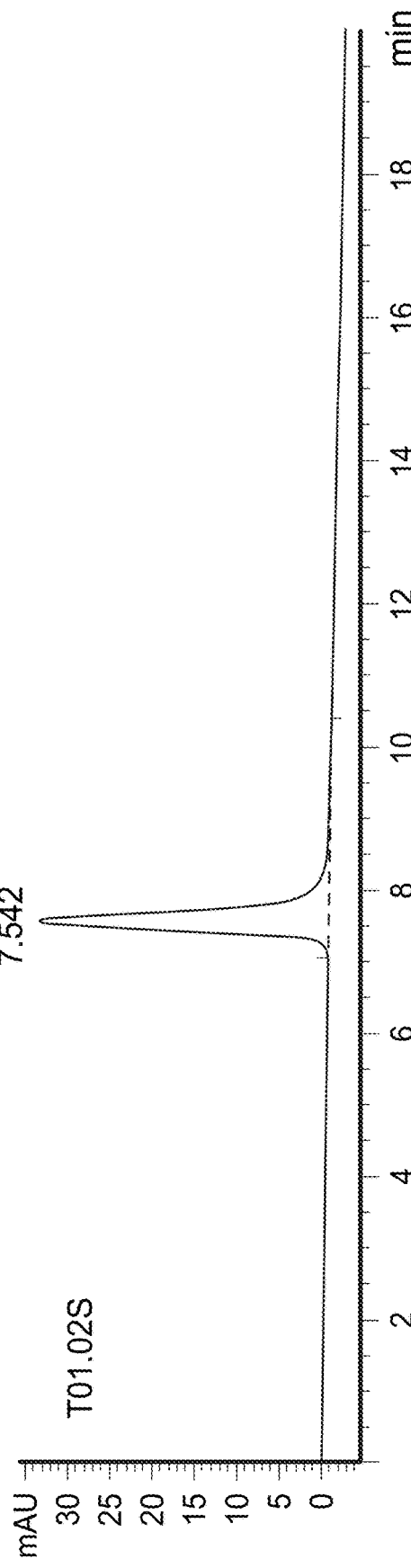
FIG. 25 is a HPLC plot showing protein profile of A2.3 antibody (EU103_T01.02S).

These experiments demonstrated, as shown schematically in FIG. 20, that VSIG4 signaling modulates suppression of T cell proliferation by M2 macrophages, and that blocking of VSIG4 signaling results in (1) abrogation of T cell proliferation induced by M2 macrophages, which leads to CD8+ T cell proliferation and tumor suppression; and (2) conversion of M2 macrophages into M1 macrophages.

Example 5: Evaluation of A1, A2, A1.3, and A2.3 Antibodies

Antibody clones A1, A2, A1.3, and A2.3 were developed by affinity maturation of EU103.2 antibodies. Protein profile by size exclusion HPLC shown in FIGS. 22, 23, 24, and 25, respectively, and summarized below in Table 4.

TABLE 4

SEC HPLC DATA FOR A1, A2, A1.3, and A2.3 antibodies

| Ab | Time | Area | Height | Width | % Area | Log (MW) | MW |
|---|---|---|---|---|---|---|---|
| A1 | 7.551 | 8.57E+02 | 29.91175 | 0.4484 | 100.000 | 2.135 | 136.605 |
| A2 | 7.567 | 2.62E+02 | 8.96929 | 0.4567 | 100.000 | 2.128 | 134.380 |
| A1.3 | 7.525 | 2.02E+03 | 106.8666 | 0.2842 | 100.000 | 2.134 | 136.081 |
| A2.3 | 7.542 | 6.61E+02 | 34.47963 | 0.2898 | 100.000 | 2.126 | 133.730 |

As shown in FIGS. 26A and 26B, A1 or A2 antibodies were applied to differentiated M2 macrophages for 2 days and FACs analysis showed a decrease in CD163, a marker for M2 macrophages, and a significant increase in CD86, a marker for M1 macrophages. Treatment with LPS/IFNγ for two days was used as positive control. Treatment with both A1 and A2 antibodies showed increased M1/M2 ratio. Specifically, A2 antibody showed a ratio increase close to that of the positive control group.

Figure 27:
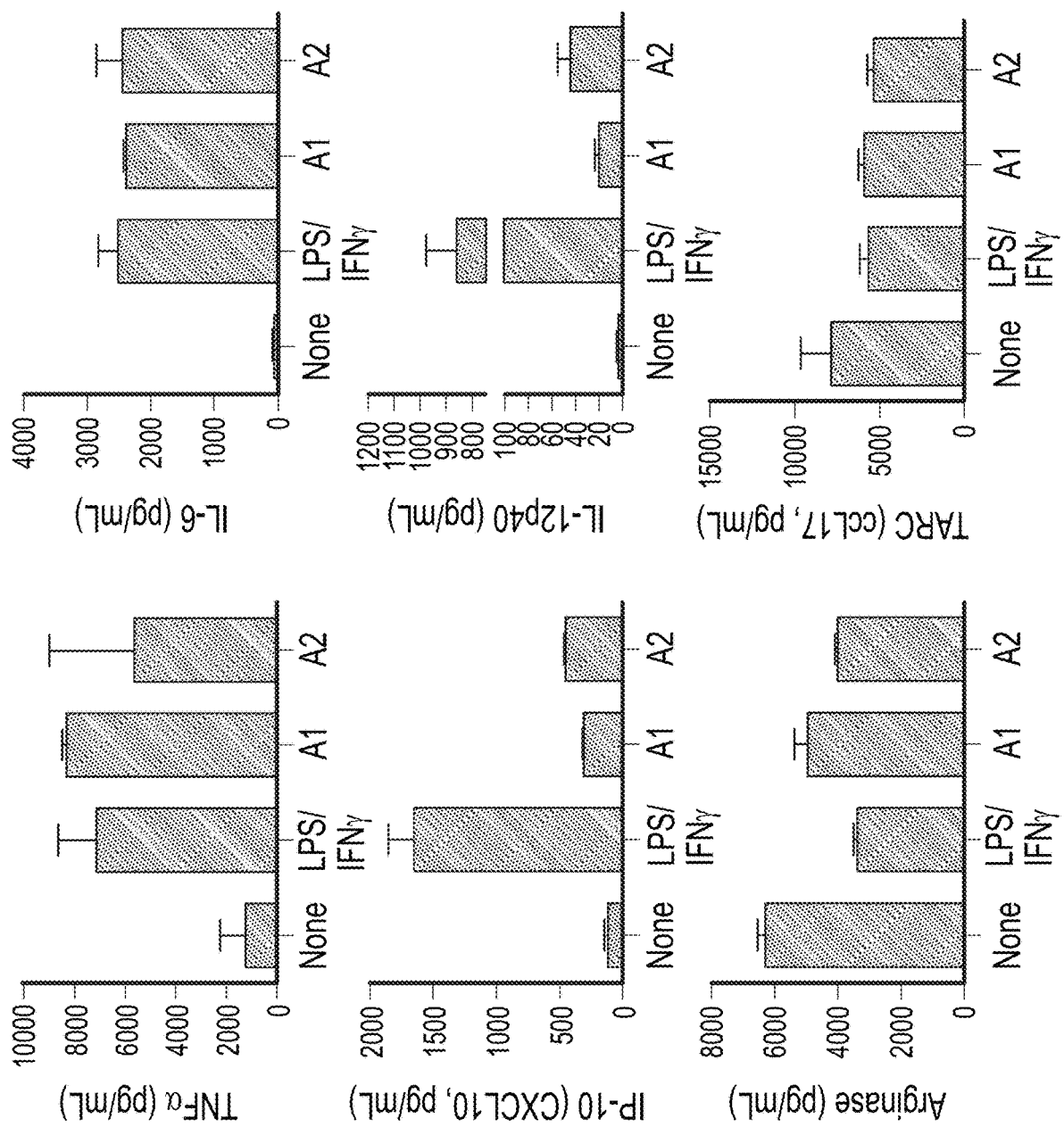
FIG. 27 is a set of graphs showing decrease of M2 type cytokines and chemokines in M2 cells treated with A1 or A2 antibodies.
Figure 27:
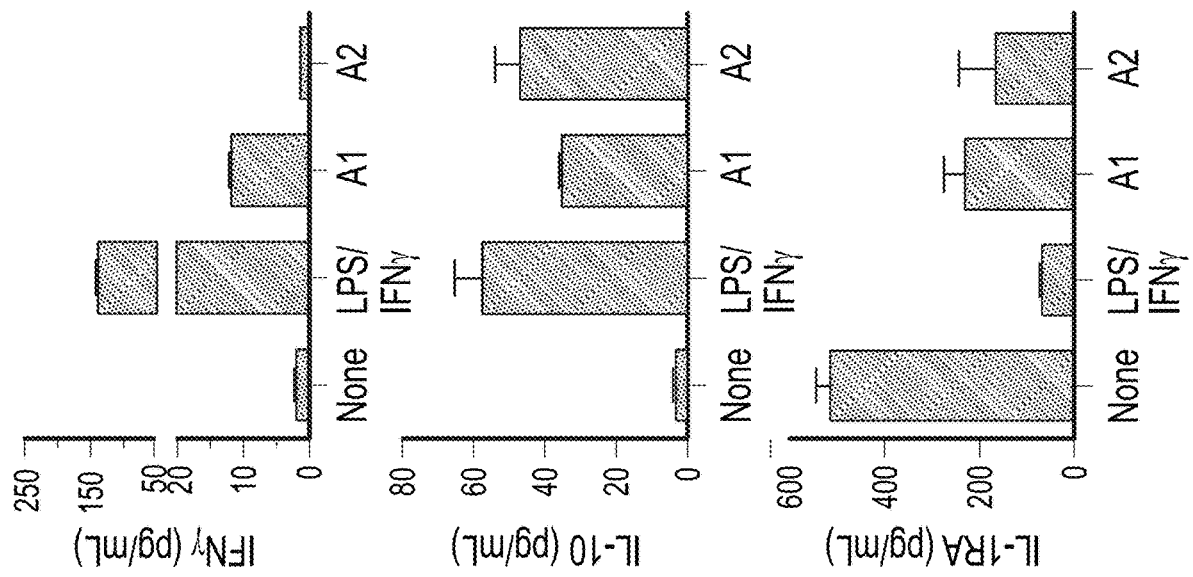

Next, as shown in FIG. 27, A1 or A2 antibodies were applied to differentiated M2 macrophages for 2 days repolarizing them to M1 macrophages and the changes in production of cytokines and chemokines in the culture medium was measured using LEGENDplex™. This is to confirm repolarization of M2 macrophages to M1 macrophages. Treatment with LPS/IFNγ for two days was used as positive control. Both A1 and A2 groups showed an increase of M1 type cytokine/chemokine (TNFα, IL6, IFNγ, IP-10, and IL12p40) compared to M2 macrophages while the production of M2 type cytokine/chemokine (IL-10, Arginase, TARC, and IL-1RA) decreased. Specifically, the increase of production of TNFα and IL6 was comparable to that of the positive control group.

Figure 28:
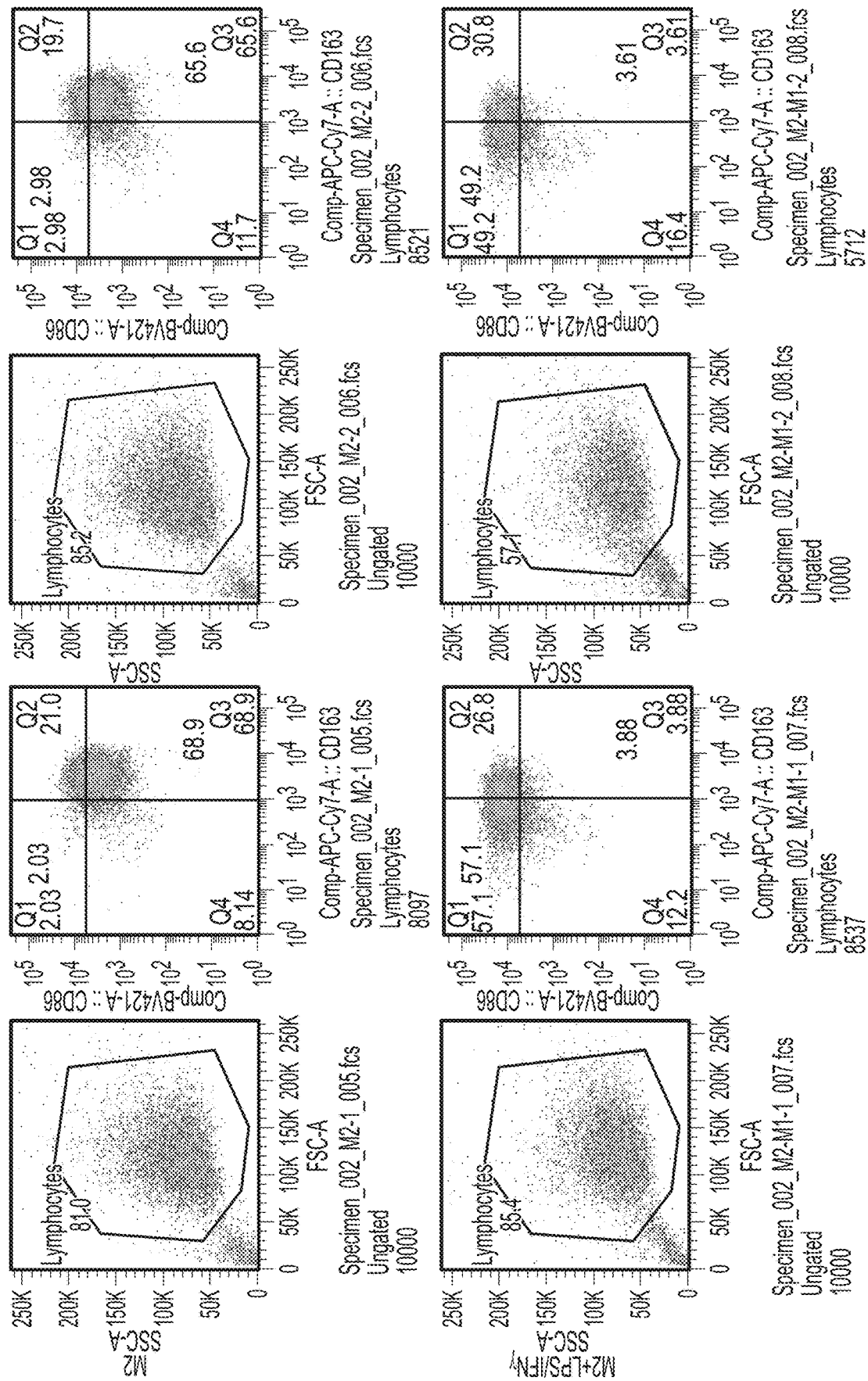
FIG. 28 is a set of FACS data showing decreased expression of CD163 and an increased expression of CD86 in M2 macrophages treated with A1 or A2 antibodies.
Figure 28:
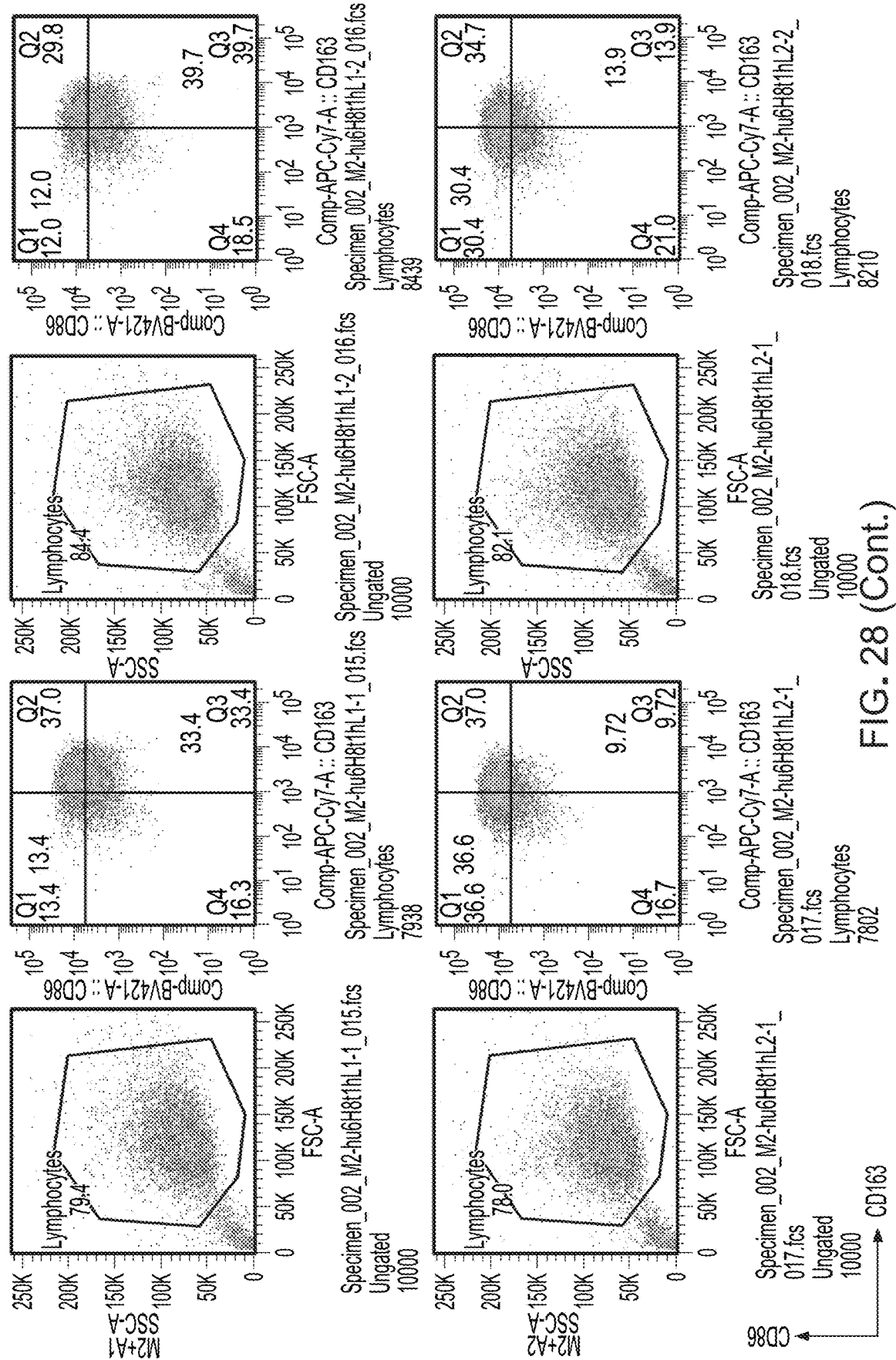

Further, as shown in FIG. 28, A1 or A2 antibodies were applied to differentiated M2 macrophages for 2 days and FACs analysis were performed to show a decrease in expression of CD163, a marker for M2 macrophages, and a significant increase in expression CD86, a marker for M1 macrophages. Treatment with LPS/IFNγ for two days was used as positive control.

Figure 29:
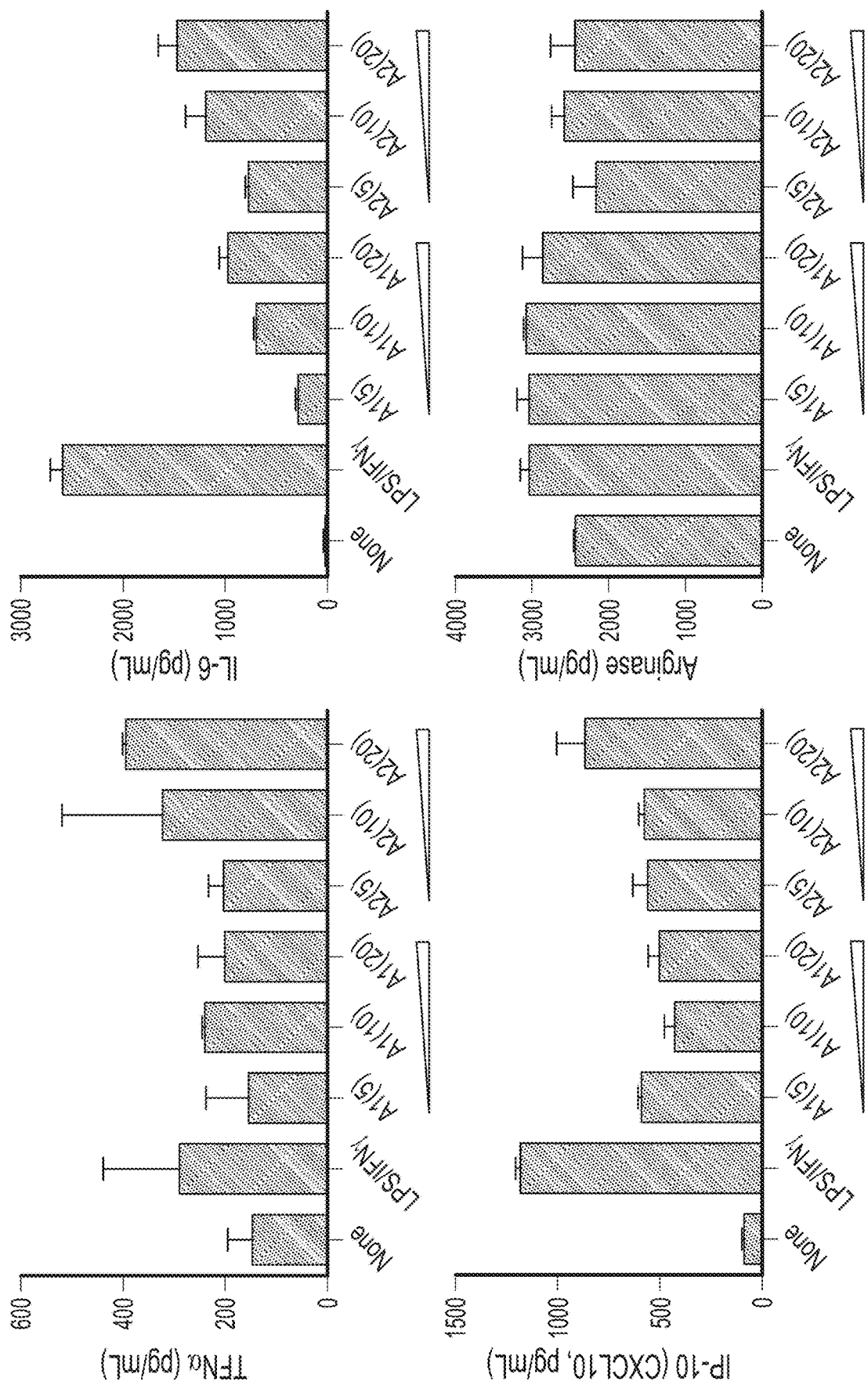
FIG. 29 is a set of graphs showing increased expression of M1 type cytokine/chemokines in M2 macrophages treated with A1 or A2 antibodies.

To further ascertain the repolarization of M2 macrophages to M1 macrophages by A1 and A2 antibodies, A1 or A2 antibodies were applied with different concentrations (5, 10 and 20 ug/ml) to differentiated M2 macrophages for 2 days and cytokine and chemokine production by the macrophages were assessed, as shown in FIG. 29. The change in the production of cytokine/chemokines in the culture medium was measured using LEGENDplex™. Treatment with LPS/IFNγ for two days was used as positive control. Both A1 and A2 groups showed an increase of TNFα, IL6, and IP-10, which are associated with M1 macrophages, and this trend was especially pronounced with when the M2 macrophages were treated with A2 antibody. The production of Arginase, which is associated with M2 macrophages, decreased regardless of concentration of the antibodies.

Figure 30:
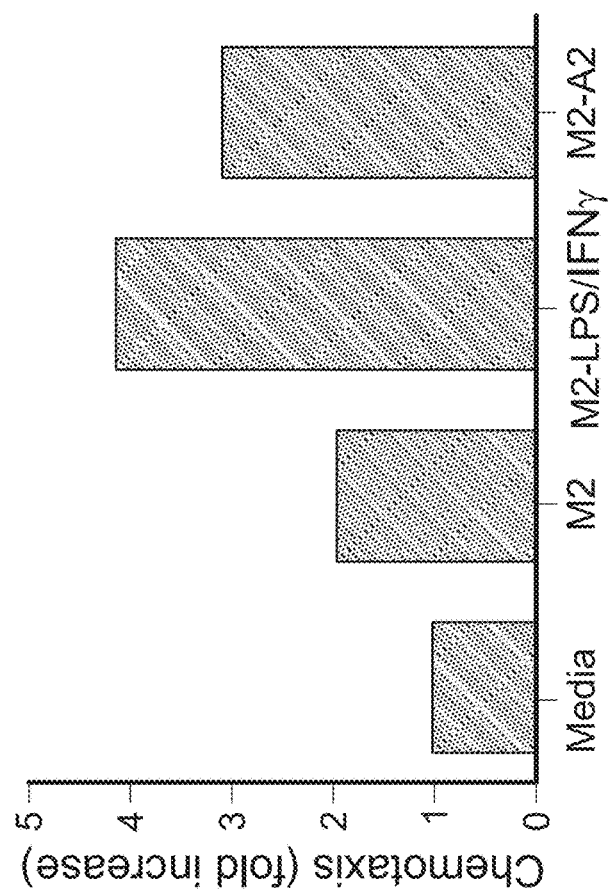
FIG. 30 is a graph showing data from a chemotaxis assay measuring the chemotactic ability of macrophages after the M2 to M1 macrophage conversion by A2 antibodies.

The chemotactic ability of macrophages after conversion of M2 macrophages into M1 macrophages by A2 antibody was assessed by chemotaxis assay. Using a Transwell 24 well 5 μm pore size chamber (Corning, Cat #CLS3421-48EA), the lower chamber was treated with the chemoattractant rhCCL19 (Biolegend, Cat #582104), which is a M1 type chemokine, at a concentration of 100 ng/ml (volume 400 μl) and the upper chamber was treated with repolarized M1 macrophages at $1.5~5\times10^5$ cells/600 μl, where M2 or A2 was applied for 2 days. (treatment with LPS/IFNγ for two days was used as positive control) After a 4 hour incubation period at 37° C. and 5% $CO_2$, 100 μl of the cells in the lower chamber were moved to a 96 well plate. Then 10 μl of CCK-8 solution (Dojindo, Cat #CK04) were added to each well and after a 1 hour incubation period the absorbance was measured (450 nm). As shown in FIG. 30, M1 macrophages from the A2 group showed chemotactic ability, confirming macrophage conversion from M2 to M1 by A2 antibody.

Figure 42:
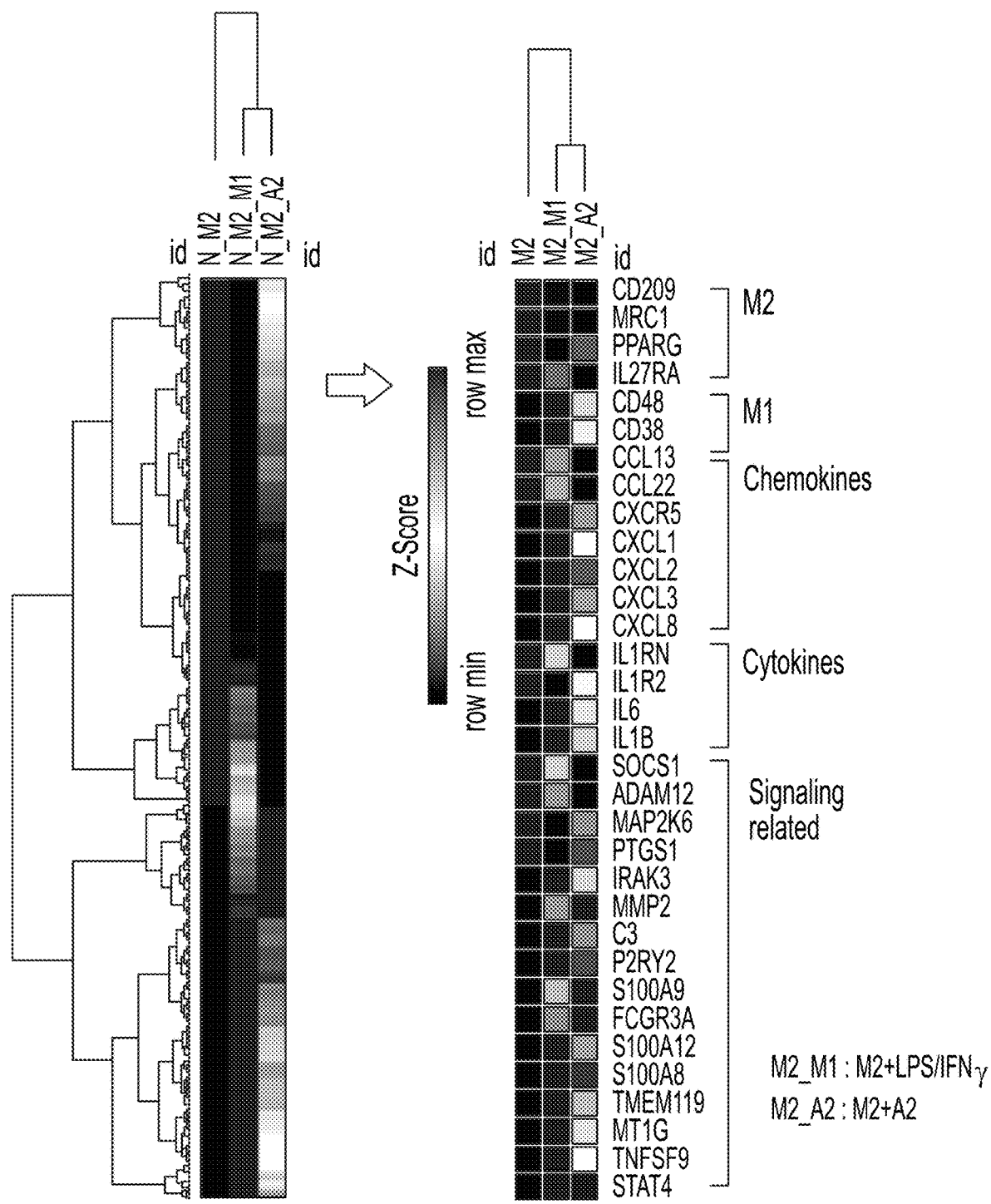
FIG. 42 is data from gene array analysis showing change in gene expression after conversion of M2 macrophages to M1 macrophages by A2 antibodies.

Gene array analysis was performed to analyze change in gene expression after conversion of M2 macrophages to M1 macrophages by A2 antibodies, as shown in FIG. 42. M2 macrophages were treated with A2 antibodies and the cells were harvested after two days. (Macrogen, Agilent Human GE 8×60K V3) Analysis shows increase of expression of M1 phenotype marker and M1 type cytokines/chemokines, similar to cells treated with LPS/IFNγ as a positive control, and decrease of expression of M2 phenotype marker and M2 type cytokines/chemokines.

Example 6: Anti-Tumor Effects of A1, A2, A1.3, and A2.3 Antibodies

Figure 31A:
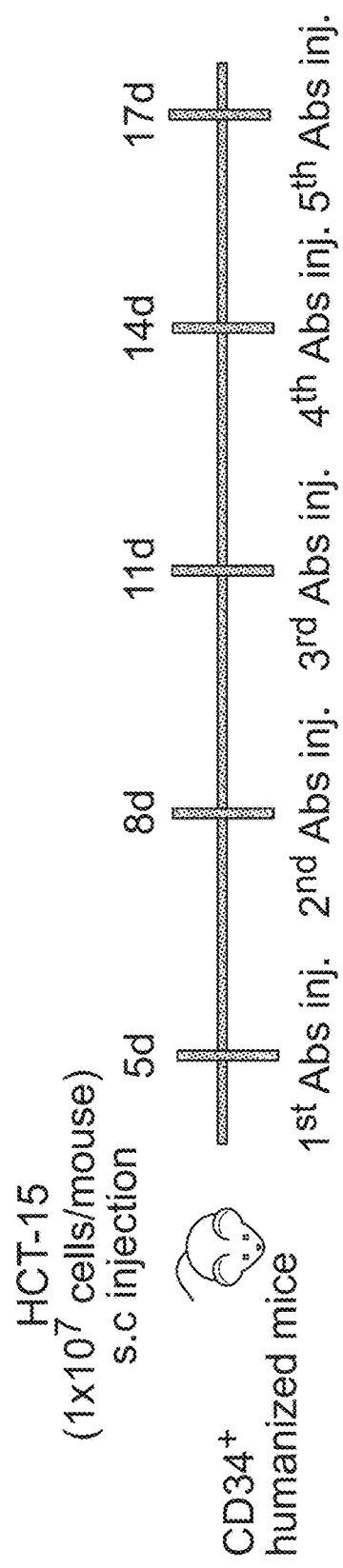

Anti-tumor effect of A1 and A2 antibodies were assessed using a humanized mouse model. human CD34 cells were injected into NBSGW mice, after that blood samples were collected and human CD45 cells in the PBMC were measured to observe humanization of the mice over a 12~14 weeks period. HCT-15 colon cancer cells were injected, $1\times10^7$ cells/mouse, into the humanized mice and after 5 days the mice were divided into three groups each receiving injections of hIgG (Sigma-Aldrich, Cat #I4506), A1 antibody, or A2 antibody. The antibodies were injected every three days for a total of 5 injections, as schematically shown in FIG. 31A. Tumor sizes were observed and after the mice were sacrificed, serum from the blood was used to measure IFNγ using ELISA (invitrogen, Cat #88-7316-88) and the tumor samples were used to analyze infiltrated leukocytes.

As shown in FIGS. 31B and 31C, no anti-tumor effect from A1 antibodies was observed but the samples from the A2 antibody group showed smaller tumor size and increase of IFNγ, confirming the anti-tumor effect of A2 antibodies.

Next, the effect of conversion of M2 macrophages into M1 macrophages by A2 antibody in the context of tumor growth was assessed in vivo. As shown schematically in FIG. 32A, SW480 colon cancer cells were injected to mice ($1\times10^7$ cells/mouse) and once the tumor size grew to a certain size (1000 mm3~), differentiated M2 macrophages ($7\times10^5$ cells/mouse) were injected with hIgG or A2 antibody. The antibodies were injected every 2 days for a total of 5 injections, and after the first injection blood samples were collected at days 4, 7 and 11 after tumor injection, and the blood samples were used to isolate serum or PBMCs to analyze the change in macrophage phenotype using FACs analysis.

Figure 32B:
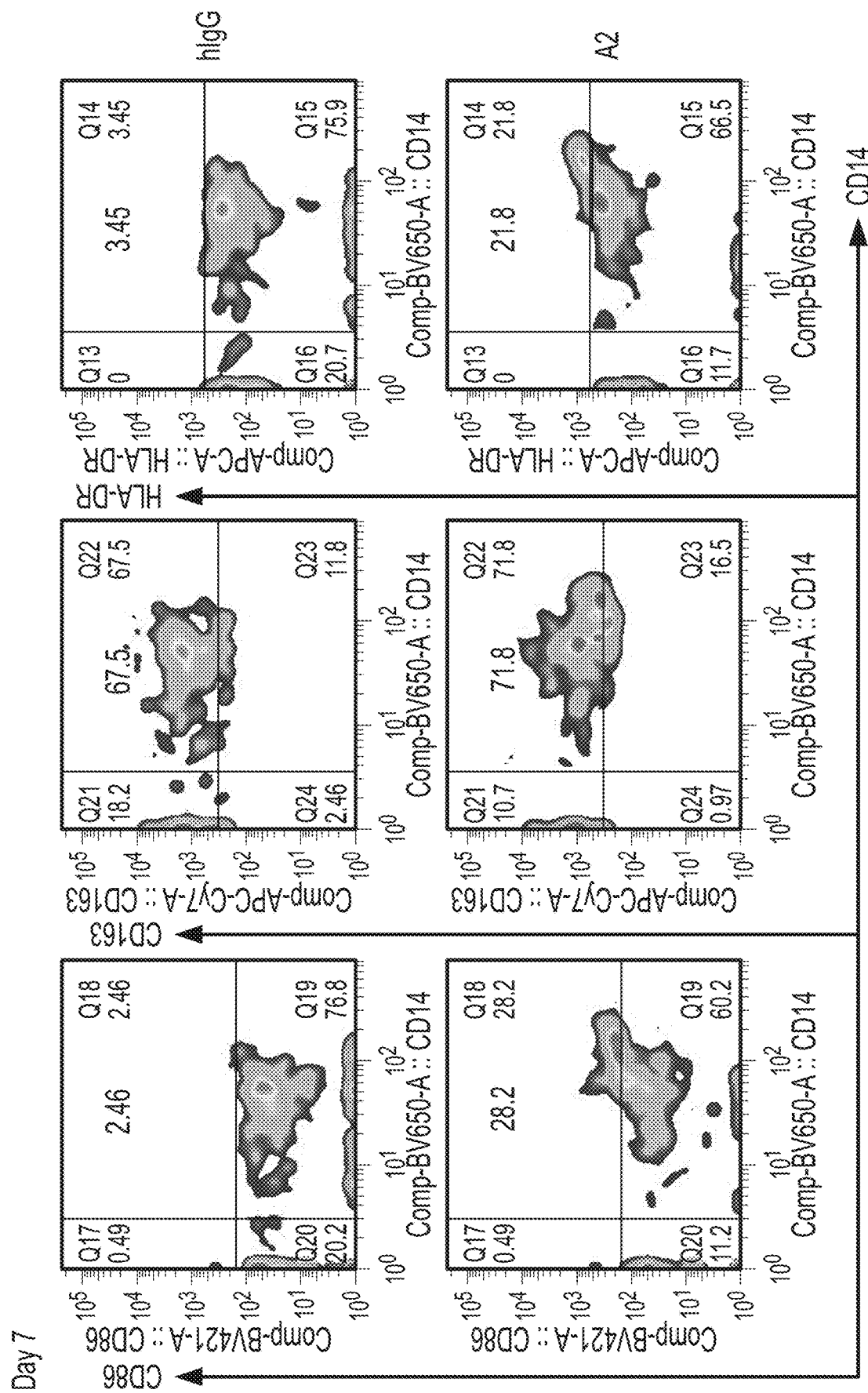
Figure 32C:
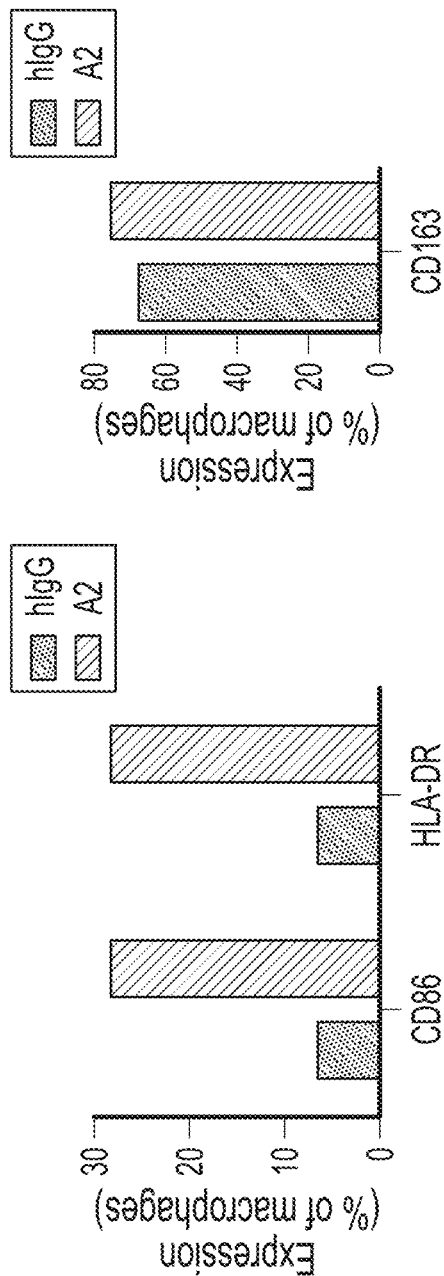

At day 7 after the tumor cell injection, a change in M1 macrophage phenotype was observed from the A2 antibody group, as shown in FIG. 32B. While there was no change in CD163, a M2 macrophages marker, the expression of CD86 and HLA-DR a M1 macrophages markers, noticeably increased compared to the hIgG group which confirms M2 to M1 macrophage conversion by A2 antibody, as shown in FIG. 32C.

Figure 33A:
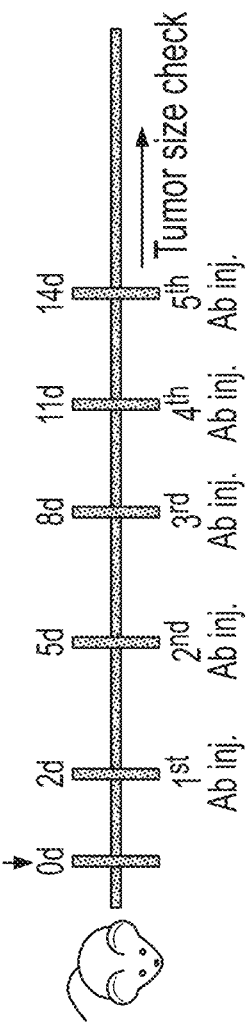
FIGS. 33A and 33B show macrophage conversion with A2 antibodies in vivo by analyzing the effect of M2 conversion to M1 macrophages on tumor growth.

Next, the effect of M2 conversion to M1 macrophages on tumor growth was analyzed. As shown schematically in FIG. 33A, a mixture of HCT-15 colon cancer cells ($8\times10^6$ cells/mouse) and varying concentrations of M2 macrophages ($2.5\times10^5/5\times10^5/1\times10^6$ cells/mouse) were injected to the mice. After 2 days, hIgG or A2 antibody was injected every 3 days for a total of 5 injections.

Figure 33B:
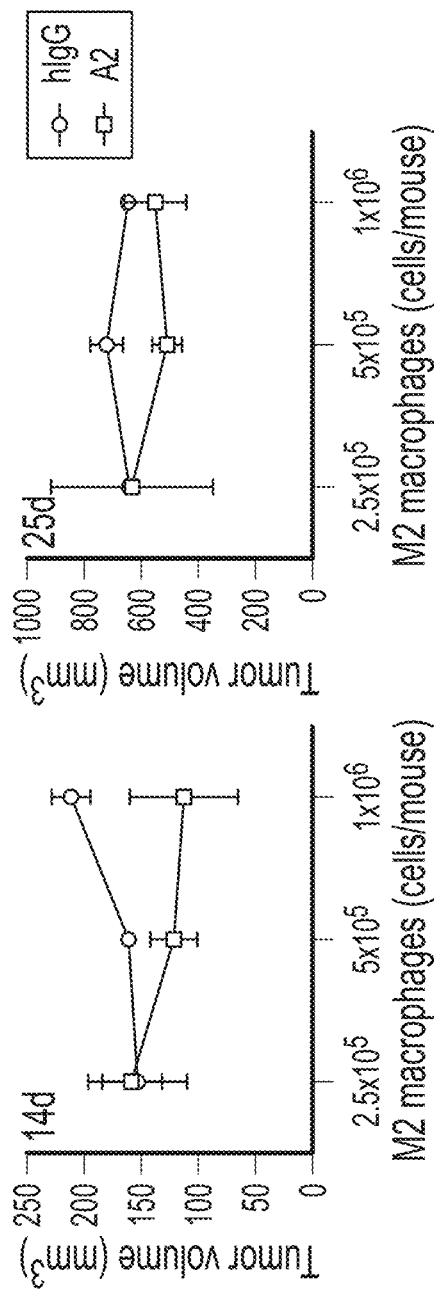

As shown in FIG. 33B, A2 antibody reduced or slowed the growth of the tumor in a dose-dependent manner at day 14 after the tumor injection, as compared to the hIgG control mice, and this effect persisted at day 25 after the tumor injection.

Figure 34A:
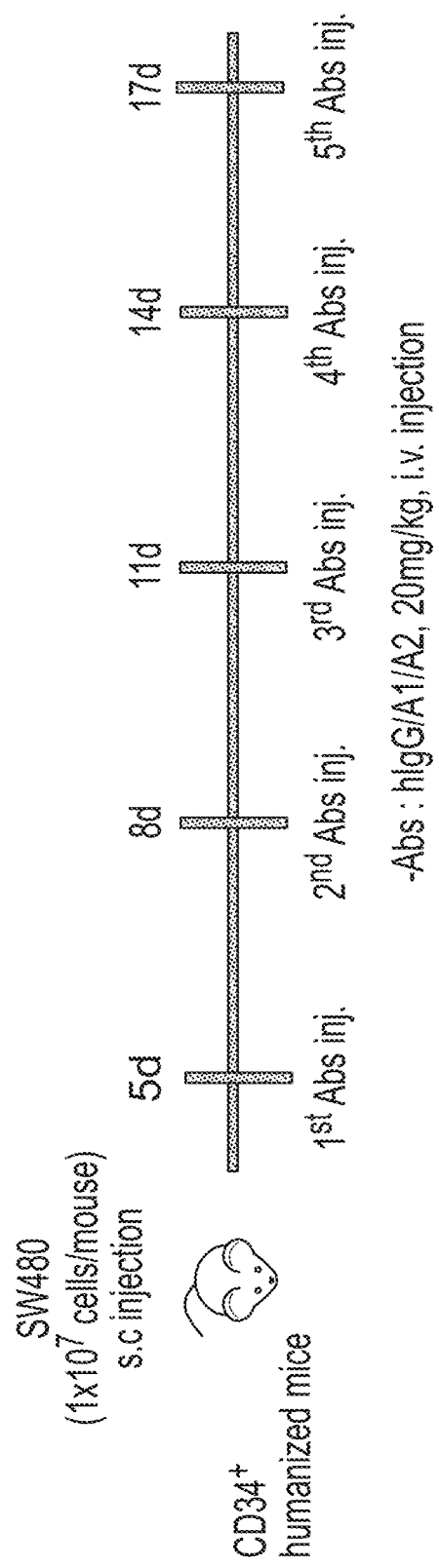
FIGS. 34A-34E show the anti-tumor effect of A2 antibodies in a humanized mouse model.

Next, the anti-tumor effects of A2 antibody in a humanized mouse model was assessed using a different mouse tumor model. As shown schematically in FIG. 34A, human CD34 cells were injected into NBSGW mice, after that blood samples were collected and human CD45 cells in the PBMC were measured to observe humanization of the mice over a 12~14 weeks period. SW480 colon cancer cells ($1\times10^7$ cells/mouse) were injected to mice and after 5 days the mice were divided into two groups each injected with hIgG or A2 antibody (20 mg/kg). The antibodies were injected every 3 days for a total of 5 injections for each group. Tumor size was observed and after the mice were sacrificed, serum from the blood was used to measure IFNγ using ELISA and the tumor samples were used to analyze infiltrated leukocytes.

Figure 34B:
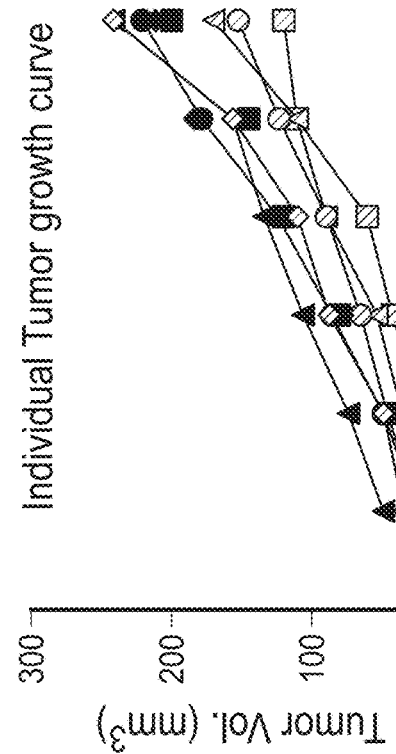
Figure 34C:
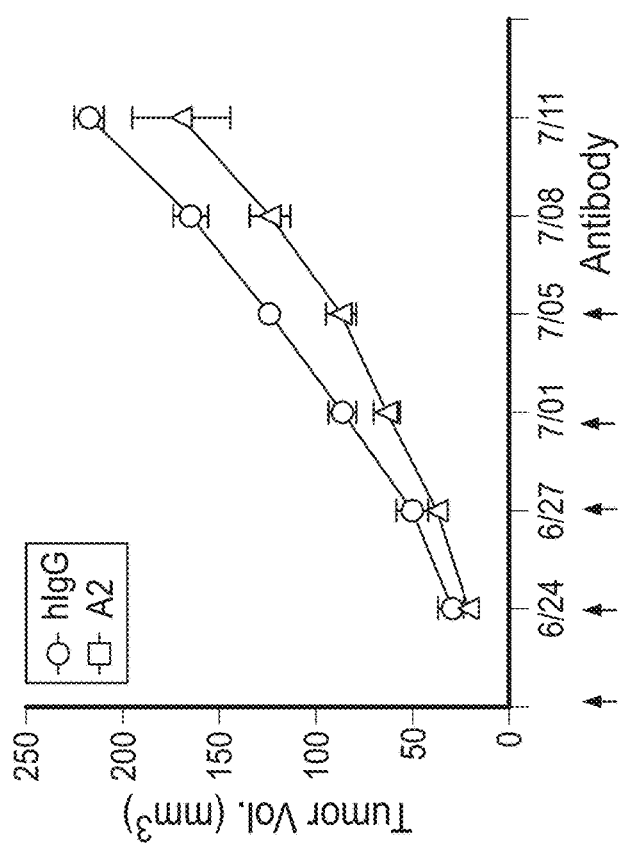

No anti-tumor effect from A1 antibodies was observed but, as shown in FIGS. 34B and 34C, the samples from the A2 antibodies group showed smaller tumor size, and increase of IFNγ was observed, further confirming the anti-tumor effects of A2 antibody.

Figure 34D:
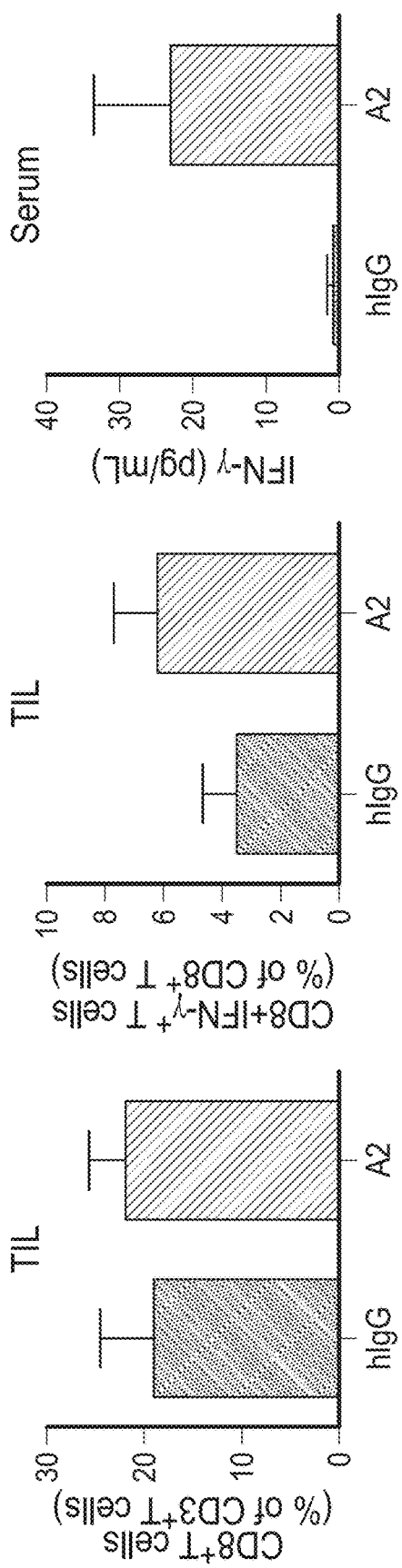
Figure 34E:
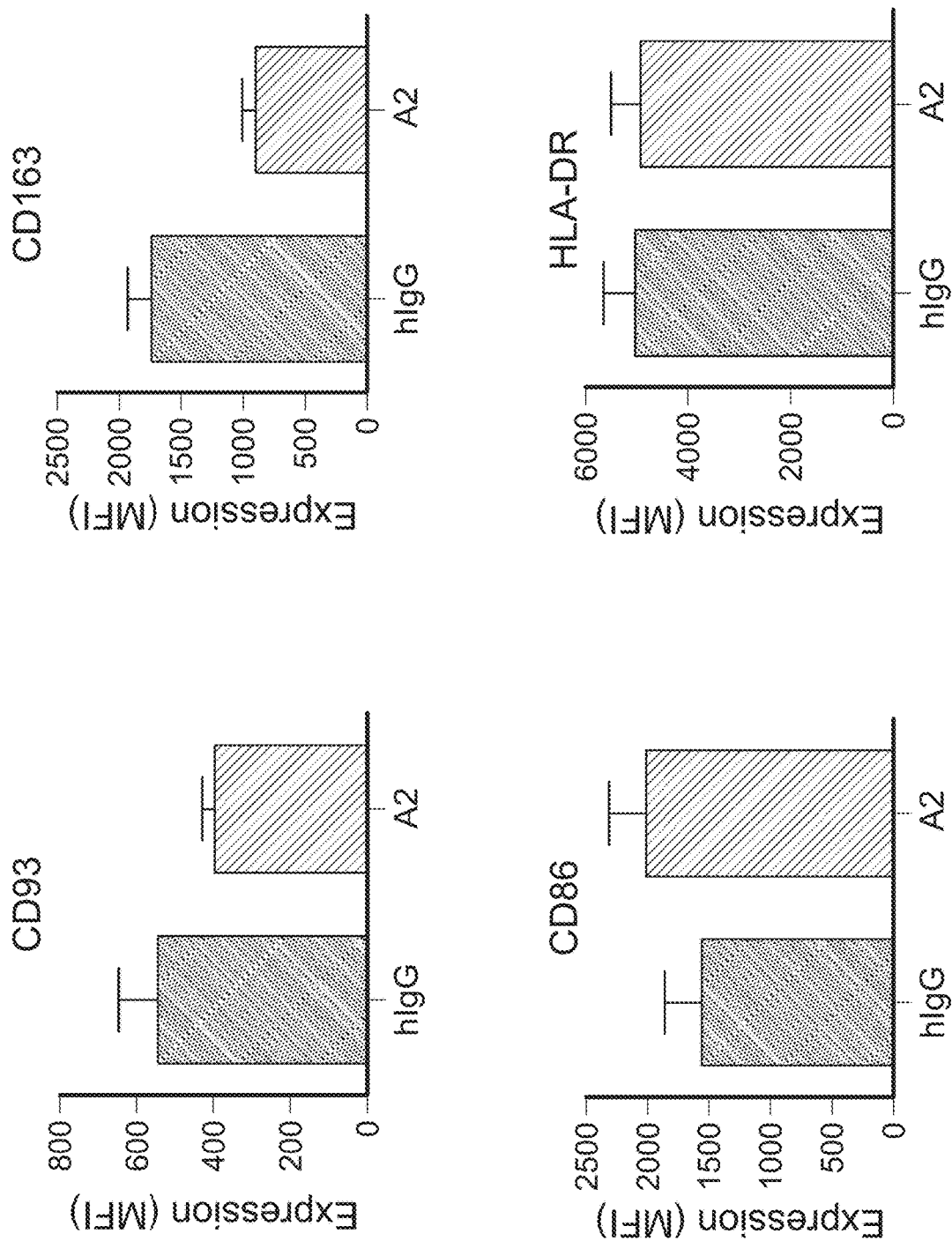

Overall, the group with A2 antibody injections showed smaller tumor size and increase of IFNγ in the serum. Further, as shown in FIG. 34D, an increase in CD8$^+$ T cells, specifically IFNγ secreting CD8γ T cells was observed. As shown in FIG. 34E, decreased CD93 and CD163 expression (M2 macrophages marker), and increased expression of CD86 (a M1 macrophages marker) was observed, while no change in HLA-DR was seen. These data confirm that A2 antibody mediates cytotoxic activity of CD8$^+$ T cells.

Figure 35A:
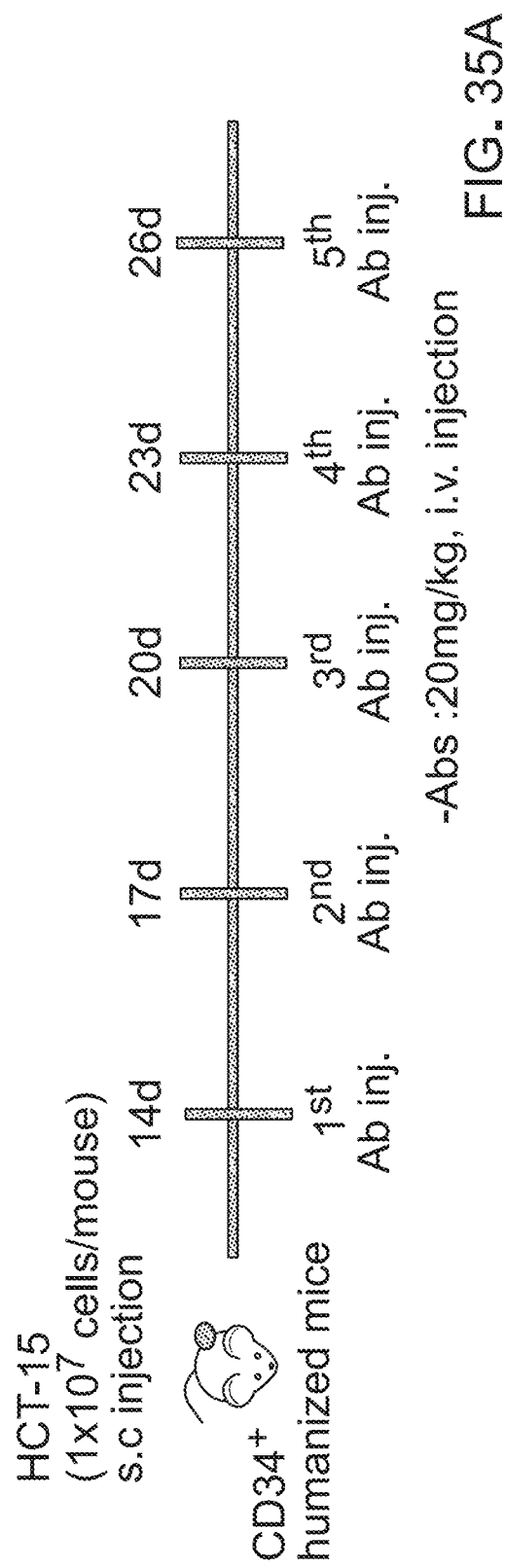
Figure 35B:
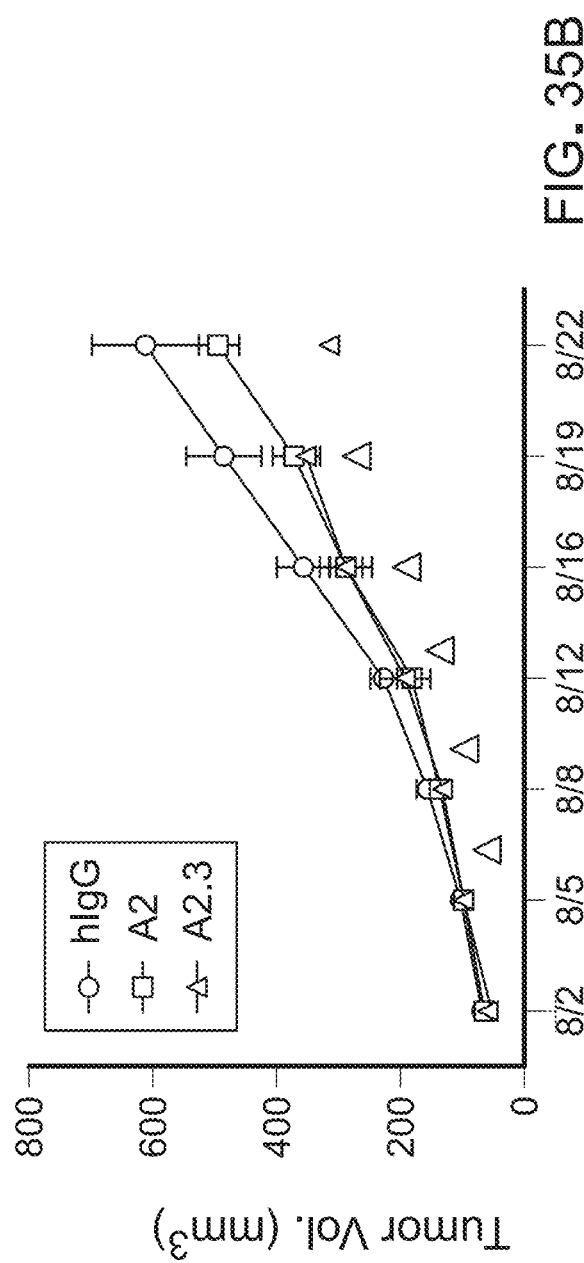

Next, anti-tumor effect of A2 and A2.3 antibodies were compared in a humanized mouse model. As schematically shown in FIG. 35A, human CD34 cells were injected into NBSGW mice, after that blood samples were collected and human CD45 cells in the PBMC were measured to observe humanization of the mice over a 12~14 weeks period. HCT-15 colon cancer cells were injected, at $1 \times 10^7$ cells/mouse, into the humanized mice and once the tumor size was grown to a certain size (~100 mm$^3$) the mice were divided into three groups each receiving injections of hIgG, A2, or A2.3 antibodies (20 mg/kg). The antibodies were injected every three days for a total of 5 injections. Tumor size was observed and after the first injection blood samples were collected at D5 and D13 where inflammatory cytokines were observed in serum from the blood. As shown in FIG. 35B, both A2 and A2.3 antibodies reduced tumor size.

Figure 36A:
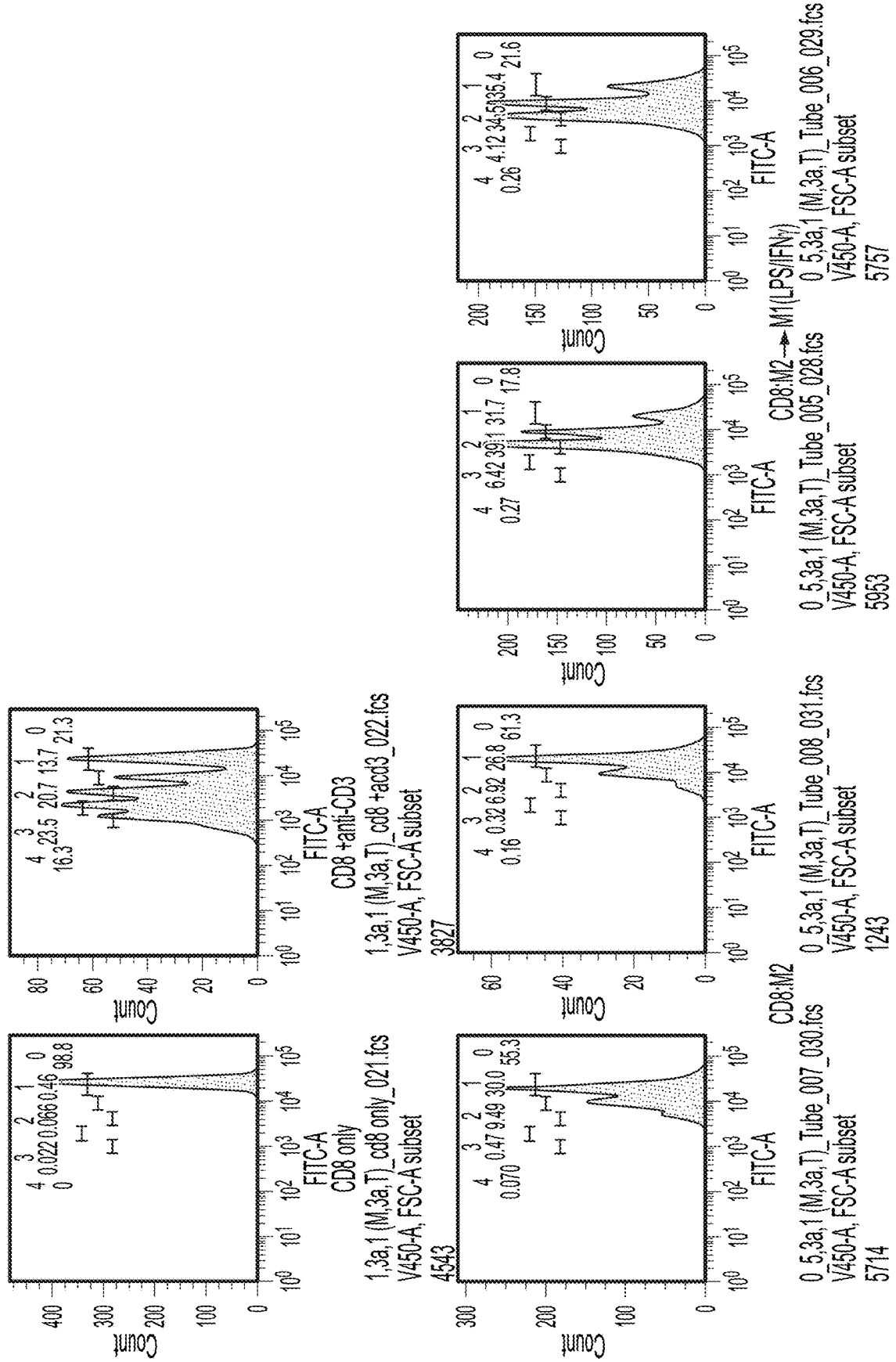
FIGS. 36A and 36B are set of data from a co-culture assay showing co-cultures of A1, A1.3, A2, and A2.3 antibodies and M2 macrophages showed increase of CD8+ T cell proliferation.

Next, the four anti-VSIG4 antibodies, A1, A1.3, A2, and A2.3 were evaluated for their effects on CD8$^+$ T cell proliferation. A1, A1.3, A2, and A2.3 antibodies were added to macrophages isolated from donors to convert M2 macrophages into M1 macrophages and co-cultured with CD8$^+$ T cells isolated from PBMCs from the same donor for a co-culture assay. The CD8$^+$ T cells were labeled with CFSE (Life technologies, Cat #V12883) and co-cultured in an anti-CD3 coated 96 well plate (BD Biocoat, Cat #354725) at a 2:1 ratio with the macrophages after conversion (CD8 T:Macrophage=$2 \times 10^5$ cells/well: $1 \times 10^5$ cells/well). After 5 days, the harvested cells were stained with hCD8-V450 and analyzed by FACs analysis. CD8$^+$ T cells proliferation was confirmed by the observation of decrease of CFSE levels. While M2 macrophages negatively regulated the CD8$^+$ T cell proliferation, the co-cultures of A1, A1.3, A2 and A2.3 antibodies resulted in conversion of M2 macrophages into M1 macrophages, and resulted in increased CD8$^+$ T cell proliferation, as shown in FIGS. 36A and 36B.

Figure 36A:
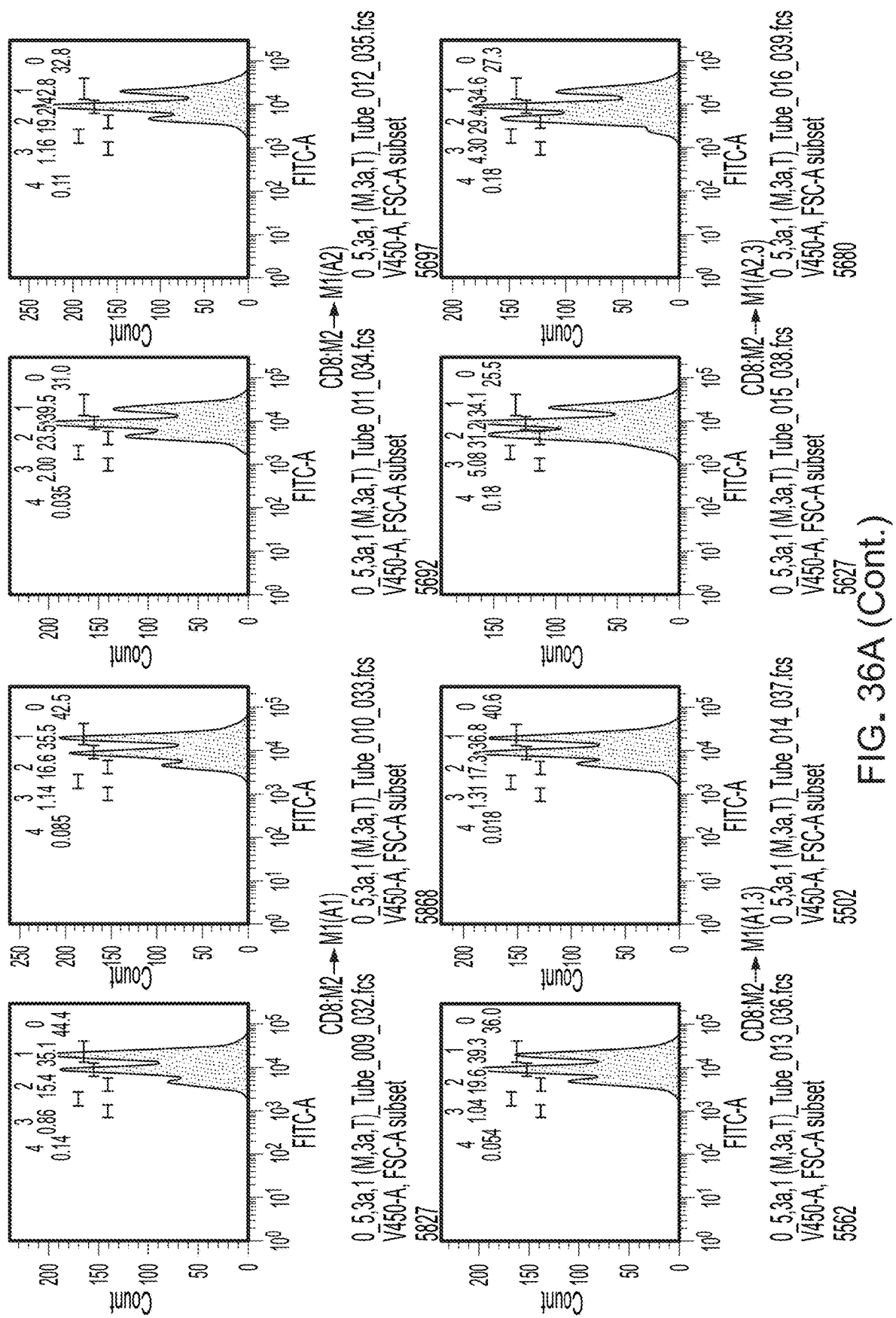
Figure 36B:
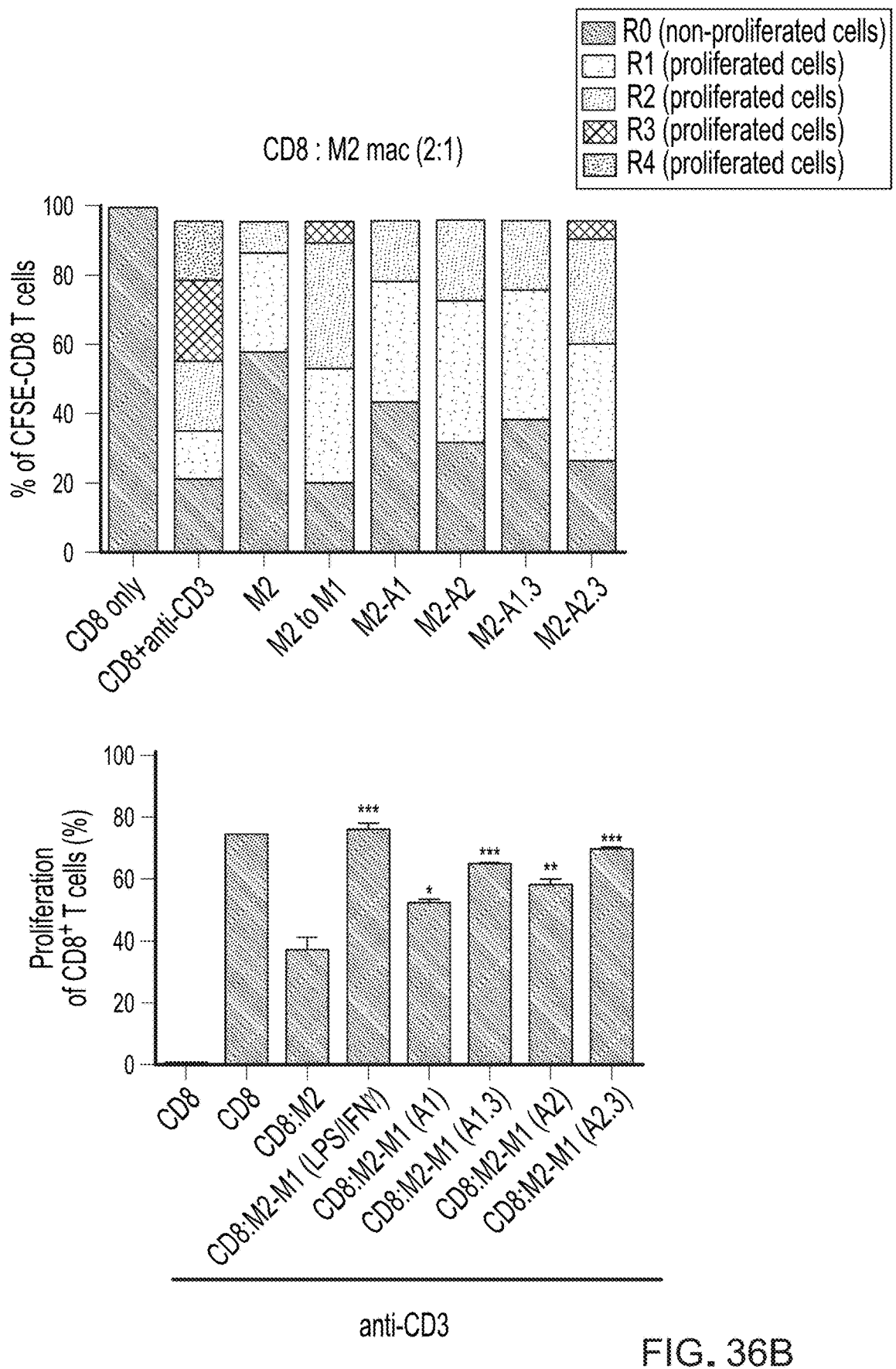
Figure 37:
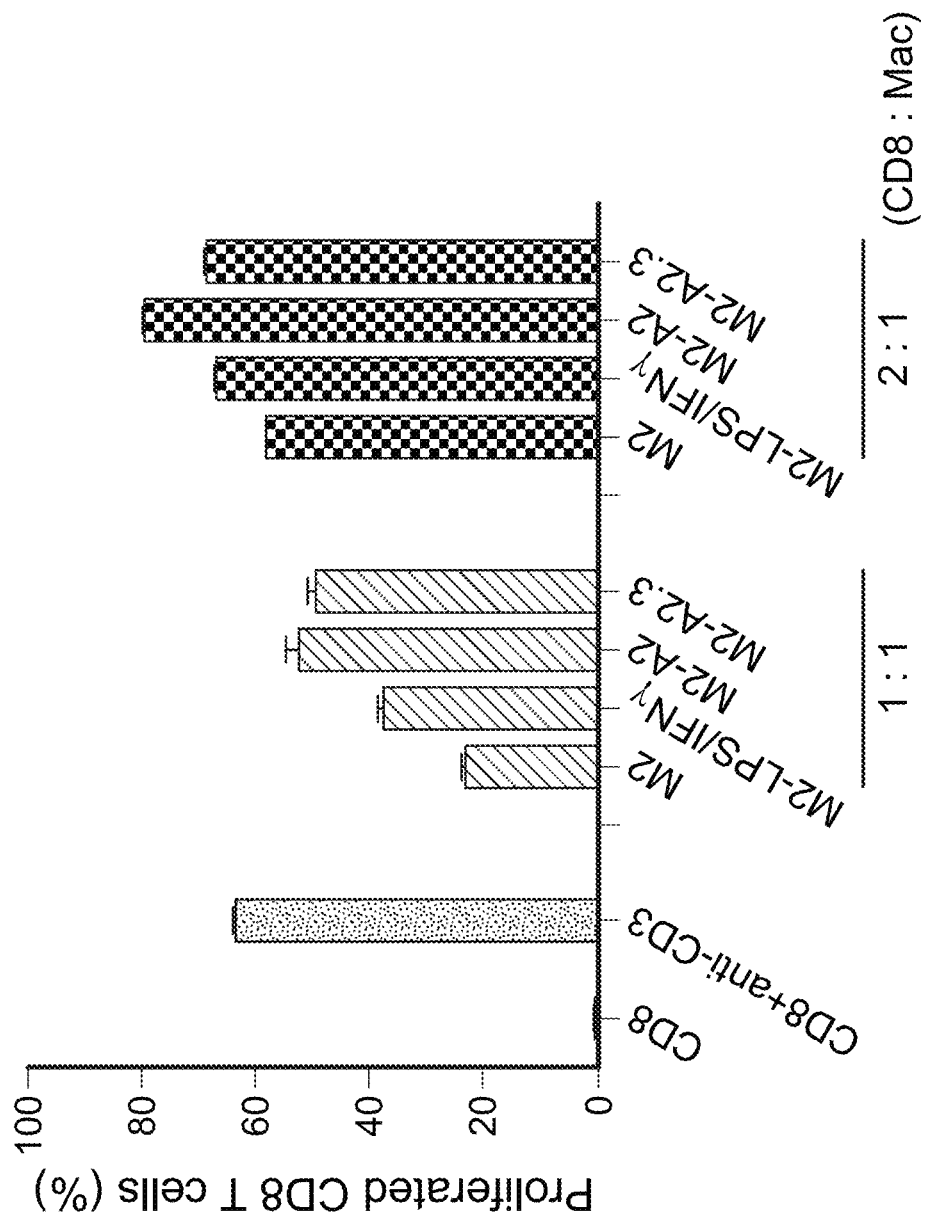
FIG. 37 is a graph showing data from a co-culture assay showing co-cultures of A2 and A2.3 antibodies with M2 macrophages showed increase of CD8+ T cell proliferation.

Similar experiments comparing the effects of A2 antibody and A2.3 antibodies were performed using macrophages and T cells isolated from different donors than in the above experiment (i.e., different from those donors in FIG. 36). A2 and A2.3 antibodies were applied to macrophages to convert M2 macrophages into M1 macrophages, and CD8$^+$ T cells were isolated from PBMCs from the same donor were used for a co-culture assay. The CD8 T cells were labeled CFSE (Life technologies, Cat #V12883) and co-cultured in a anti-CD3 coated 96 well plate (BD Biocoat, Cat #354725) at a 1:1 or 2:1 ratio with the macrophages after conversion (CD8$^+$ T: Macrophage=$2 \times 10^5$ cells/well: $2 \times 10^5$ cells/well or $2 \times 10^5$ cells/well: $1 \times 10^5$ cells/well). After 5 days, the harvested cells were stained with hCD8-V450 and analyzed by FACs analysis. CD8$^+$ T cells proliferation was confirmed by the observation of decrease of CFSE levels. While M2 macrophages negatively regulated the CD8$^+$ T cell proliferation, addition of A2 and A2.3 antibodies to convert M2 macrophages into M1 macrophages resulted in increased CD8$^+$ T cell proliferation.

Figures 38A, 38B:
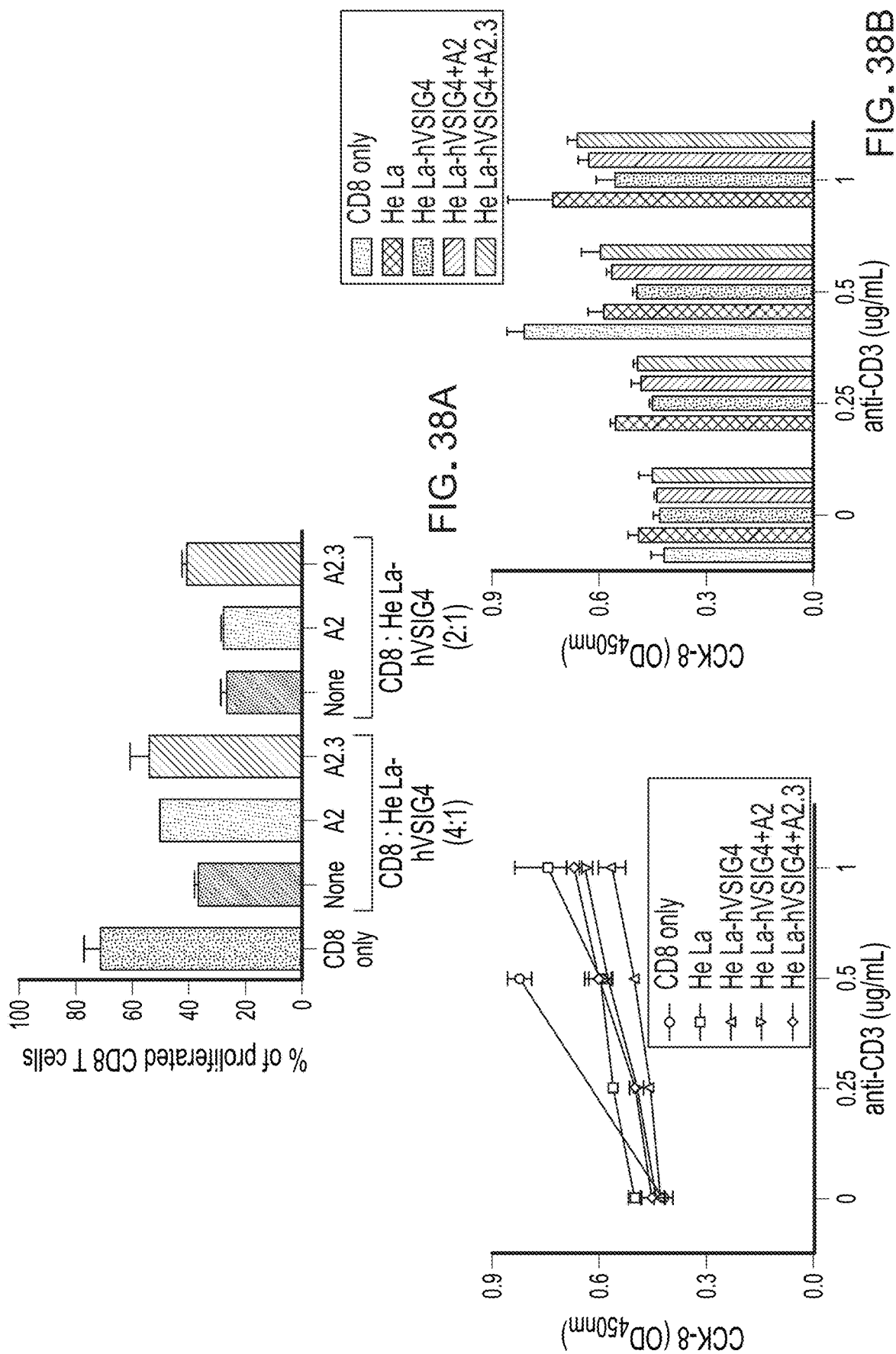
FIGS. 38A and 38B are set of graphs showing the use of hVSIG4 expressing HeLa-hVSIG4 cells to observe CD8+ T cell proliferation by A2 or A2.3 antibodies.

Next, the hVSIG4 expressing HeLa cells (HeLa-hVSIG4 cells) were used to confirm the role of VSIG4 signaling on A2 and A2.3 antibody-mediated induction of CD8$^+$ T cell proliferation. CD8$^+$ T cells were isolated from PBMCs from a healthy donor, labeled with CFSE and applied to a anti-CD3 coated plate ($2 \times 10^5$ cells/well). After 1 day, the HeLa or HeLa-hVSIG4 cells were added to the wells after 30 Gy irradiation (x-ray) ($1 \times 10^5$ or $0.5 \times 10^5$ cells/well). After 5 days, CD8$^+$ T cell proliferation was analyzed by measuring CFSE levels using FACs analysis. The CD8$^+$ T cells were also treated with anti-CD3 (Miltenyi Biotech, Cat #130-093-387) at different concentrations and after 1 day, the HeLa or HeLa-hVSIG4 cells were added to the wells after 30 Gy irradiation (x-ray)—($1 \times 10^5$ cells/well). After 5 days, 100 μl of the cultured cells was moved to a separate 96 well plate and CCK-8 was added to each well (10 ul/well). After 5 hours, the absorbance was measured at 450 nm confirming CD8$^+$ T cell proliferation. As shown in FIGS. 38A and 38B, HeLa-hVSIG4 negatively regulated CD8$^+$ T cell proliferation, while treatment with A2 or A2.3 induces T cell proliferation.

Figure 39:
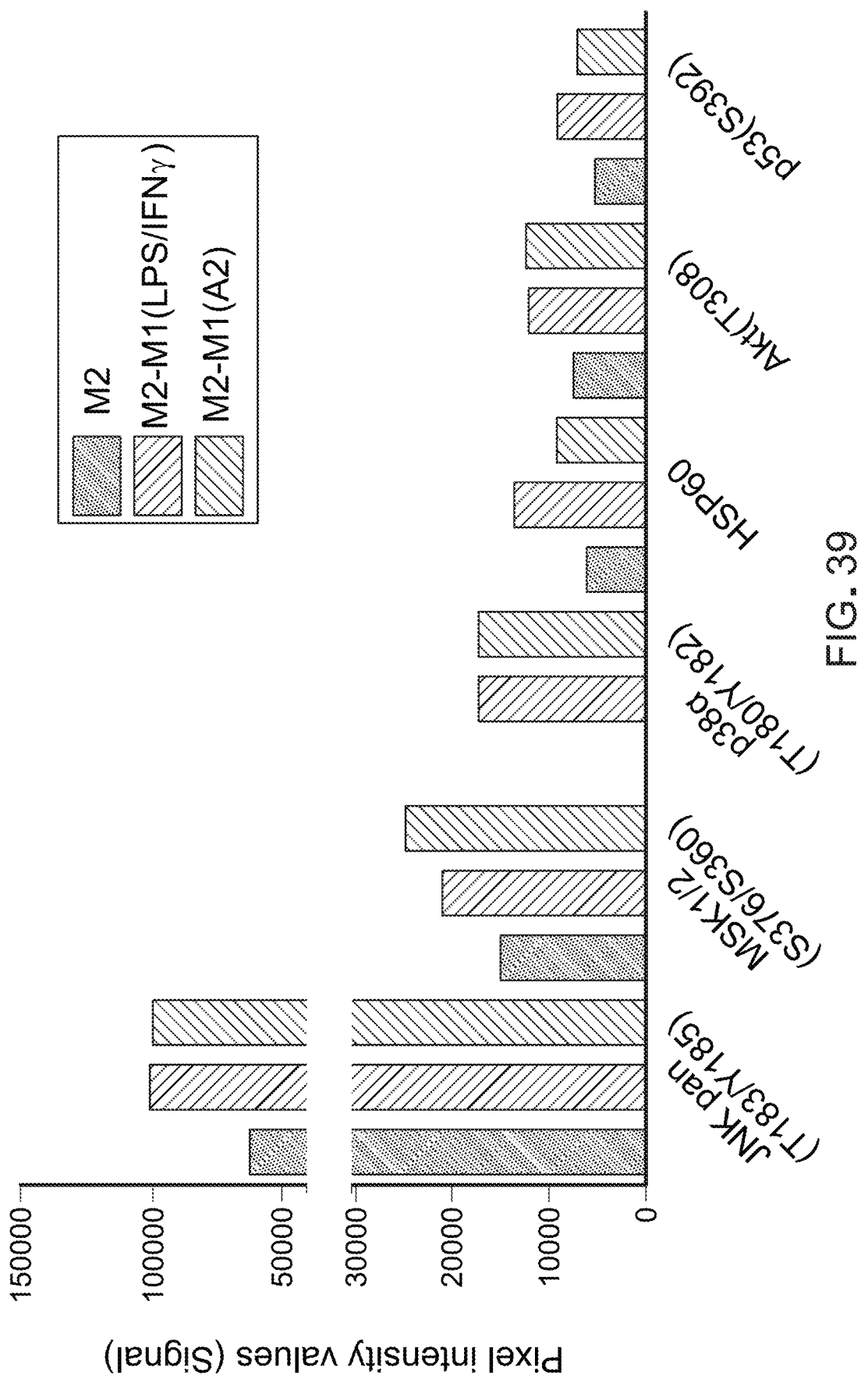
FIG. 39 is a graph showing the use of human phosphor-kinase array to observe the signal pathway of the macrophage conversion by A2 antibodies.

Human phosphor-kinase array was used to examine the signal pathway through which macrophage is repolarized by A2 antibody. As shown in FIG. 39, conversion of M2 macrophages into M1 macrophages by A2 antibody treatment resulted in significant increase in phosphorylation of JNK, MSK1/2, and p38a, as measured using Proteome Profiler™ Antibody Arrays (R&D Systems, Cat #ARY003B).

Antibody Sequence and Binding Affinity Information

Sequence information and binding affinity information for the various anti-VSIG4 antibodies described herein are provided in TABLES 5-12, below.

TABLE 5

| VH AND VL SEQUENCES OF EU103.2 ANTIBODY | |
|---|---|
| Ab name | Sequence |
| EU103.2_VH (amino acid) | QVQLQESGPGLVKPSQTLSLTCSFSGISLTTSGMG VGWIRQPPGKGLEWLADIFWDDNKYYNPSLKSRVT ISVDTSKNQFSLKLSSVTAADTAVYYCVRVYYKND GYFDVWGQGTLVTVSS (SEQ ID NO: 2) |
| EU103.2_VL (amino acid) | EIVMTQSPATLSVSPGERATLSCRASKSVTTSGYS FMHWYQQKPGQAPRLLIYLASNLEPGIPARFSGSG SGTEFTLTISSLQSEDFAVYYCQHSRELPYTFGQG TKLEIK (SEQ ID NO: 4) |

TABLE 6

| VH AND VL SEQUENCES OF EU103.3 ANTIBODY | |
|---|---|
| Ab name | Sequence |
| EU103.3_VH (hu6H8.3_VH) (amino acid) | QVTLKESGPTLVKPTQTLTLTCTFSGISLTTSGMG RQPPGKALEWLADIFWDDNKYYNPSLKVGWISRLT ITKDTSKNQVVLTMTNMDPVDTATYYCVRVYYKND GYFDVWGKGTTVTVSS (SEQ ID NO: 6) |

TABLE 6-continued

VH AND VL SEQUENCES OF EU103.3 ANTIBODY

| Ab name | Sequence |
|---|---|
| EU103.3_VL (hu6H8.3_VL) (amino acid) | DIVLTQSPLSLPVTLGQPASISCRASKSVTTSGYS FMHWYQQRPGQSPRLLIYLASNLEPGVPDRFSGSG SGTDFTLKISRVEAEDVGVYYCQHSRELPYTFGQG TKLEIK (SEQ ID NO: 8) |

TABLE 7

VH AND VL SEQUENCES OF A1 ANTIBODY

| Ab name | Sequence |
|---|---|
| A1_VH (amino acid) | QVTLKESGPTLVKPTQTLTLTCTFSGISLTTSGM GVGWIRQPPGKALEWLADIFWDDNKYYNPSLKSR LTITKDTSKNQVVLTMTNMDPVDTATYYCVRVYY KNDGYFDVWGKGTTVTVSS (SEQ ID NO: 6) |
| A1_VL (amino acid) | DIVLTQSPLSLPVTLGQPASISCRASKSVTTSGY SFMHWYQQRPGQSPRLLIYLASNLEPGVPDRFSG SGSGTDFTLKISRVEAEDVGVYYCQQSGELPYTF GQGTKLEIK (SEQ ID NO: 10) |

TABLE 8

VH AND VL SEQUENCES OF A2 ANTIBODY

| Ab name | Sequence |
|---|---|
| A2_VH (amino acid) | QVTLKESGPTLVKPTQTLTLTCTFSGISLTTSGM GVGWIRQPPGKALEWLADIFWDDNKYYNPSLKSR LTITKDTSKNQVVLTMTNMDPVDTATYYCVRVYY KNDGYFDVWGKGTTVTVSS (SEQ ID NO: 6) |

TABLE 8-continued

VH AND VL SEQUENCES OF A2 ANTIBODY

| Ab name | Sequence |
|---|---|
| A2_VL (amino acid) | DIVLTQSPLSLPVTLGQPASISCRASKSVTTSGY SFMHWYQQRPGQSPRLLIYLASNLEPGVPDRFSG SGSGTDFTLKIFRVEAEDVGVYYCQQSGELPYTF GQGTKLEIK (SEQ ID NO: 12) |

TABLE 9

VH AND VL SEQUENCES OF A1.3 ANTIBODY

| Ab name | Sequence |
|---|---|
| A1.3_VH (amino acid) | QVTLVESGPTLVKPGQTLTLTCTFSGISLTTSGMGV GWIRQPPGKALEWLADIFWDDNKYYNPSLKGRLTIT KDTSKNQVYLTMTNMDPVDTATYYCVRVYYKNDGYF DVWGKGTTVTVSS (SEQ ID NO: 14) |
| A1.3_VL (amino acid) | DIVLTQSPLSLPVTLGQPASISCRASKSVTTSGYSF MHWYQQRPGQSPRLLIYLASNLEPGVPDRFSGSGSG TDFTLKISRVEAEDVGVYYCQQSGELPYTFGQGTKL EIK (SEQ ID NO: 10) |

TABLE 10

VH AND VL SEQUENCES OF A2.3 ANTIBODY

| Ab name | Sequence |
|---|---|
| A2.3_VH (amino acid) | QVTLVESGPTLVKPGQTLTLTCTFSGISLTTSGMG VGWIRQPPGKALEWLADIFWDDNKYYNPSLKGRLT ITKDTSKNQVYLTMTNMDPVDTATYYCVRVYYKND GYFDVWGKGTTVTVSS (SEQ ID NO: 16) |
| A2.3_VL (amino acid) | DIVLTQSPLSLPVTLGQPASISCRASKSVTTSGYS FMHWYQQRPGQSPRLLIYLASNLEPGVPDRFSGSG SGTDFTLKIFRVEAEDVGVYYCQQSGELPYTFGQG TKLEIK (SEQ ID NO: 12) |

TABLE 11

CDR SEQUENCES OF EU103.2, EU103.3, A1, A2, A1.3, and A2.3 ANTIBODIES

| | VH CDR1 | VH CDR2 | VH CDR3 | VL CDR1 | VL CDR2 | VL CDR3 |
|---|---|---|---|---|---|---|
| EU103.2 | GISLTT (SEQ ID NO: 17) | IFWDDNK (SEQ ID NO: 18) | VRVYYKN DGYFDV (SEQ ID NO: 19) | KSVTTS (SEQ ID NO: 20) | LAS (SEQ ID NO: 21) | QHSRELPYT (SEQ ID NO: 22) |
| EU103.3 | GISLTT (SEQ ID NO: 17) | IFWDDNK (SEQ ID NO: 18) | VRVYYKN DGYFDV (SEQ ID NO: 19) | KSVTTS (SEQ ID NO: 20) | LAS (SEQ ID NO: 21) | QHSRELPYT (SEQ ID NO: 22) |
| A1 | GISLTT (SEQ ID NO: 17) | IFWDDNK (SEQ ID NO: 18) | VRVYYKN DGYFDV (SEQ ID NO: 19) | KSVTTS (SEQ ID NO: 20) | LAS (SEQ ID NO: 21) | QQSGELPYT (SEQ ID NO: 23) |
| A2 | GISLTT (SEQ ID NO: 17) | IFWDDNK (SEQ ID NO: 18) | VRVYYKN DGYFDV (SEQ ID NO 19) | KSVTTS (SEQ ID NO: 20) | LAS (SEQ ID NO: 21) | QQSGELPYT (SEQ ID NO: 23) |
| A1.3 | GISLTT (SEQ ID NO: 17) | IFWDDNK (SEQ ID NO: 18) | VRVYYKN DGYFDV (SEQ ID NO: 19) | KSVTTS (SEQ ID NO: 20) | LAS (SEQ ID NO: 21) | QQSGELPYT (SEQ ID NO: 23) |

TABLE 11-continued

CDR SEQUENCES OF EU103.2, EU103.3, A1, A2, A1.3, and A2.3 ANTIBODIES

| | VH CDR1 | VH CDR2 | VH CDR3 | VL CDR1 | VL CDR2 | VL CDR3 |
|---|---|---|---|---|---|---|
| A2.3 | GISLTT (SEQ ID NO: 17) | IFWDDNK (SEQ ID NO: 18) | VRVYYKN DGYFDV (SEQ ID NO: 19) | KSVTTS (SEQ ID NO: 20) | LAS (SEQ ID NO: 21) | QQSGELPYT (SEQ ID NO: 23) |

TABLE 12

BINDING AFFINITY ($K_D$) OF EU103.2, EU103.3, A1, A2, A1.3, and A2.3 ANTIBODIES FOR VSIG4

| Antibody | Ka(1/Ms) | Kd(1/s) | KD (M) |
|---|---|---|---|
| EU103.2 | 1.834E+5 | 0.01313 | 7.156E−8 |
| A1 | 3.779E+5 | 0.003283 | 8.688E−9 |
| A1.3 | 4.022E+5 | 0.003198 | 7.952E−9 |
| A2 | 3.604E+5 | 0.002964 | 8.226E−9 |
| A2.3 | 4.037E+5 | 0.003083 | 7.636E−9 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. An anti-V-Set and Immunoglobulin Domain Containing 4 (VSIG4) antibody or antigen-binding fragment thereof, comprising:
   a. a heavy chain CDR1 comprising the amino acid sequence of SEQ ID NO: 17, a heavy chain CDR2 comprising the amino acid sequence of SEQ ID NO: 18, a heavy chain CDR3 sequence comprising the amino acid sequence of SEQ ID NO: 19; and
   b. a light chain CDR1 comprising the amino acid sequence of SEQ ID NO: 20, a light chain CDR2 comprising the amino acid sequence of SEQ ID NO: 21, and a light chain CDR3 comprising the amino acid sequence of SEQ ID NO: 22 or SEQ ID NO: 23.

2. The anti-VSIG4 antibody or antigen-binding fragment of claim 1, wherein the antibody or antigen-binding fragment comprises any one of the following:
   a. a heavy chain variable domain comprising an amino acid sequence at least 80%, 90%, 95%, 96%, 97%, 98%, or 99% identical to the amino acid sequence of SEQ ID NO: 2, SEQ ID NO: 6, SEQ ID NO: 14, or SEQ ID NO: 16;
   b. a light chain variable domain comprising an amino acid sequence at least 80%, 90%, 95%, 96%, 97%, 98%, or 99% identical to the amino acid sequence of SEQ ID NO: 4, SEQ ID NO: 8, SEQ ID NO: 10, or SEQ ID NO: 12; or
   c. a heavy chain variable domain comprising an amino acid sequence at least 80%, 90%, 95%, 96%, 97%, 98%, or 99% identical to the amino acid sequence of SEQ ID NO: 2, SEQ ID NO: 6, SEQ ID NO: 14, or SEQ ID NO: 16, and a light chain variable domain comprising an amino acid sequence at least 80%, 90%, 95%, 96%, 97%, 98%, or 99% identical to the amino acid sequence of SEQ ID NO: 4, SEQ ID NO: 8, SEQ ID NO: 10, or SEQ ID NO: 12.

3. The anti-VSIG4 antibody or antigen-binding fragment of claim 2, wherein the antibody or antigen-binding fragment comprises any one of the following:
   a. a heavy chain variable domain comprising the amino acid sequence of SEQ ID NO: 2, SEQ ID NO: 6, SEQ ID NO: 14, or SEQ ID NO: 16;
   b. a light chain variable domain comprising the amino acid sequence of SEQ ID NO: 4, SEQ ID NO: 8, SEQ ID NO: 10, or SEQ ID NO: 12; or
   c. a heavy chain variable domain comprising the amino acid sequence of SEQ ID NO: 2, SEQ ID NO: 6, SEQ ID NO: 14, or SEQ ID NO: 16, and a light chain variable domain comprising the amino acid sequence of SEQ ID NO: 4, SEQ ID NO: 8, SEQ ID NO: 10, or SEQ ID NO: 12.

4. The anti-VSIG4 antibody or antigen-binding fragment of claim 1, wherein the antibody wherein light chain CDR3 comprising the amino acid sequence of SEQ ID NO: 23.

5. The anti-VSIG4 antibody or antigen-binding fragment of claim 2, wherein the antibody or antigen-binding fragment comprises a heavy chain variable domain comprising the amino acid sequence of SEQ ID NO: 2 and a light chain variable domain comprising the amino acid sequence of SEQ ID NO: 4.

6. The anti-VSIG4 antibody or antigen-binding fragment of claim 2, wherein the antibody or antigen-binding fragment comprises a heavy chain variable domain comprising the amino acid sequence of SEQ ID NO: 6 and a light chain variable domain comprising the amino acid sequence of SEQ ID NO: 8.

7. The anti-VSIG4 antibody or antigen-binding fragment of claim 2, wherein the antibody or antigen-binding fragment comprises a heavy chain variable domain comprising the amino acid sequence of SEQ ID NO: 6 and a light chain variable domain comprising the amino acid sequence of SEQ ID NO: 10.

8. The anti-VSIG4 antibody or antigen-binding fragment of claim 2, wherein the antibody or antigen-binding fragment comprises a heavy chain variable domain comprising the amino acid sequence of SEQ ID NO: 6 and a light chain variable domain comprising the amino acid sequence of SEQ ID NO: 12.

9. The anti-VSIG4 antibody or antigen-binding fragment of claim 2, wherein the antibody or antigen-binding fragment comprises a heavy chain variable domain comprising the amino acid sequence of SEQ ID NO: 14 and a light chain variable domain comprising the amino acid sequence of SEQ ID NO: 10.

10. The anti-VSIG4 antibody or antigen-binding fragment of claim 2, wherein the antibody or antigen-binding fragment comprises a heavy chain variable domain comprising the amino acid sequence of SEQ ID NO: 16 and a light chain variable domain comprising the amino acid sequence of SEQ ID NO: 12.

11. The anti-VSIG4 antibody or antigen-binding fragment of claim 1, wherein the antibody or antigen-binding fragment has a binding affinity ($K_D$) for a human V-Set and Immunoglobulin Domain Containing 4 (VSIG4) molecule of $1 \times 10^{-7}$ to $1 \times 10^{-9}$ M.

12. The anti-VSIG4 antibody or antigen-binding fragment of claim 1, wherein the antibody or antigen-binding fragment has a binding affinity ($K_D$) for a VSIG4 molecule of about $7.156 \times 10^{-8}$ to about $7.636 \times 10^{-9}$ M.

13. The anti-VSIG4 antibody or antigen-binding fragment of claim 1, wherein the antibody or antigen-binding fragment has a binding affinity ($K_D$) for a VSIG4 molecule of about $7.156 \times 10^{-8}$ M, about $7.636 \times 10^{-9}$ M, about $7.952 \times 10^{-9}$ M, about $8.226 \times 10^{-9}$ M, or about $8.688 \times 10^{-9}$ M.

14. A nucleic acid molecule encoding the anti-VSIG4 antibody or antigen-binding fragment of claim 1.

15. A recombinant vector comprising the nucleic acid molecule of claim 14.

16. The recombinant vector of claim 15, wherein the nucleic acid molecule is operatively linked to a promoter.

17. The recombinant vector of claim 16, wherein the vector comprises two separate vectors, each comprising the nucleic acid sequence encoding the heavy chain and the light chain of the antibody or antigen-binding fragment.

18. A host cell comprising the recombinant vector of claim 15.

19. The host cell of claim 18, wherein the host cell is a mammalian cell, a yeast cell, or a bacterial cell.

20. The host cell of claim 19, wherein the host cell is a cell selected from the group consisting of E. coli, P. pastoris, Sf9, COS, HEK293, CHO-K1, and a mammalian lymphocyte.

21. A pharmaceutical composition comprising:
the anti-VSIG4 antibody or antigen-binding fragment of claim 1; and
a pharmaceutically acceptable carrier.

22. A method of treating a subject having cancer, the method comprising administering to the subject a composition that comprises or delivers the anti-VSIG4 antibody or antigen-binding fragment of claim 1, thereby treating the cancer.

23. The method of claim 22, wherein the cancer is selected from a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, and prostate cancer.

24. The method of claim 22, wherein the subject is administered one or more additional anticancer therapies selected from ionizing radiation, a chemotherapeutic agent, an antibody agent, and a cell-based therapy.

25. The method of claim 24, wherein the one or more additional anticancer therapies comprise an immune checkpoint inhibitor, IL-12, GM-CSF, an anti-CD4 agent, cisplatin, fluorouracil, doxorubicin, irinotecan, paclitaxel, indoleamine 2,3-dioxygenase-1 (IDO1) inhibitor, or cyclophosphamide.

26. A method of increasing secretion of cytokines or chemokines in M2 macrophages comprising contacting the M2 macrophages with the antibody or antigen-binding fragment of claim 1.

27. A method of inducing $CD8^+$ T cell proliferation, the method comprising:
a. contacting an M2 macrophage with the anti-VSIG4 antibody or antigen-binding fragment of claim 1; and
b. co-incubating the M2 macrophage with a $CD8^+$ T cell.

28. A method of converting an M2 macrophage into an M1 macrophage, the method comprising contacting the M2 macrophage with the anti-VSIG4 antibody or antigen-binding fragment of claim 1.

* * * * *